US005715835A

United States Patent [19]
Lishko et al.

[11] Patent Number: 5,715,835
[45] Date of Patent: Feb. 10, 1998

[54] METHODS FOR TREATING AND REDUCING THE POTENTIAL FOR CARDIOVASCULAR DISEASE USING METHIONINASE COMPOSITIONS

[75] Inventors: Valeryi Lishko, Shaker Hts., Ohio; Yuying Tan, San Diego, Calif.

[73] Assignee: AntiCancer, Inc., San Diego, Calif.

[21] Appl. No.: 486,519

[22] Filed: Jun. 7, 1995

Related U.S. Application Data

[63] Continuation-in-part of PCT/US93/11311, Nov. 19, 1993 and a continuation-in-part of Ser. No. 979,165, Nov. 19, 1992, abandoned.

[51] Int. Cl.$^6$ .................................................. A61B 19/00
[52] U.S. Cl. ............................................................. 128/898
[58] Field of Search ................................... 128/630, 898

[56] References Cited

U.S. PATENT DOCUMENTS

| | | | |
|---|---|---|---|
| 4,071,405 | 1/1978 | Soda et al. | 195/29 |
| 4,298,590 | 11/1981 | Bogoch. | |
| 5,028,420 | 7/1991 | Masegi et al. | |
| 5,487,984 | 1/1996 | Allet et al. | |

OTHER PUBLICATIONS

*Biostatistical Analysis*, Prenctice Hall, New Jersey, pp. 292–297 (1984).
Breillout et al., "Methionine Dependency of Malignant Tumors: A Possible Approach for Therapy," *J. of National Cancer Institute* 82:1628–1632 (1990).
Chello et al., *Cancer Research* 33:1898–1904 (1973).
Cohen et al., "Nonchromosomal Antibiotic Resistance in Bacteria: Genetic Transformation of *Escherichia coli* by R–Factor DNA," *Proc. Natl. Acad. Sci. USA* 69:2110–2114 (1972).
Dethy et al., *J. Nuclear Med.* 35:1162–1166 (1994).
Eagle, *Science* 122:501 (1995).
Eagle, *Science* 130:432 (1959).

Freeman et al., *Proc. Natl. Acad. Sci. USA* 83:2694–2698 (1986).
Graham and Van Der EB, "A New Techniques for the Assay of Infectivity of Human Adenovirus 5 DNA," *Virology* 52:456–467 (1973).
Hernandez et al., *Cir. Farm.* 45:49–60 (1986–1987).
Hoffman et al., *Proc. Natl. Acad. Sci USA* 77:7306–7310 (1980).
Hoffman, *Anticancer Res.* 5:1–30 (1985).
Hoffman et al., *Proc. Natl. Acad. Sci. USA* 86:2013–2017 (1989).
Hoffman et al., "Altered Methionine Metabolism, DNA Methylation and Oncogene Expression in Carcinogenesis," *Biochem. Biophys. Acta* 738:49–87 (1984).
Huovinen et al., "Carbon–11–methionine and PET in evaluation of treatment response of breast cancer," *Br. J. Cancer* 67:787–791 (1993).
Ito et al., *Biochemistry* 79:1263–1272 (1976).
Kang, "Hyperhomocyst(e)inemia as a Risk Factor For Occlusive Vascular Disease," *Annu. Rev. Nutr.* 12:279–298 (1992).
Kreis and Hession, *Cancer Research* 33:1862–1865 (1973).
Kreis and Hession, "Biological Effects of Enzymatic Deprivation of L–Methionine in Cell Culture and Experimental Tumor," *Cancer Research* 33:1866–1869 (1973).
Kreis et al., "Effect of Nutrional and Enzymatic Methionine Deprivation upon Human Normal and Malignant Cells in Tissue Culture," *Cancer Research* 40:634–641 (1980).
Lapela et al., *J. Nucl. Med.* 35:1618–23 (1994).
Leighton, *J. Nat'l Cancer Institute* 12:545–561 (1951).
Leskinen-Kallio et al., *J. Nucl. Med.* 33:691–695 (1992).

(List continued on next page.)

*Primary Examiner*—Lee S. Cohen
*Assistant Examiner*—Samuel Gilbert
*Attorney, Agent, or Firm*—Morrison & Foerster LLP

[57] ABSTRACT

The present invention provides methods for treating and reducing the potential for cardiovascular disease using methioninase compositions having less than 10 ng endotoxin per mg methioninase.

13 Claims, 16 Drawing Sheets

OTHER PUBLICATIONS

Leskinen–Kallio et al., "Uptake of Carbon–11–Methionine and Fluorodeoxyglucose in Non–Hodgkin's Lymphoma: A PET Study," *J. of Nuclear Medicine* 32:1211–1218 (1991).

Lindholm et al., *J. Nucl. Med.* 34:1711–1716 (1993).

Lowry et al., "Protein Measurement with the Folin Phenol Reagent," *J. Biol. Chem.* 193:265 (1951).

Matteucci and Caruthers, "Synthesis of Deoxyoligonucleotides on a Polymer Support,"0 *J. Am. Chem. Soc.* 103:3185–3191 (1981).

McCully, "Vascular Pathology of Homocytseinemia: Implications for the Pathogenesis of Arteriosclerosis," *Am.J. Pathology* 56:111–128 (1969).

Mecham et al., *Biochem. Biophys. Res. Commun.* 117:432 (1983).

Mineura et al., "Innovative Approach in the Diagnosis of Gliomatosis Cerebri Using Carbon–11–L–Methionine Positron Emission Tomography," *J. of Nuclear Med.* 32:726–728 (1991).

Miyazawa et al., *J. Nucl. Med.* 34:1886–1891 (1993).

Nakayama et al., "Purification and Properties of L–Methionine Gamma–Lyase From Aeromonas SP," *Agric. Biol. Chem.* 48:2367–2369 (1984).

Nieto et al., "Cloning vectors, derived from a naturally occuring plasmid of *Pseudomonas savastanoi*, specifically tailored for genetic manipulations in Pseudomonas," *Gene* 87:145–149 (1990).

Sambrook et al., *Molecular Cloning: A Laboratory Manual*, Cold Spring Harbor Laboratory Press, pp. A.1–A.4 (1989).

Sambrook et al., *Molecular Cloning: A Laboratory Manual*, Cold Spring Harbor Laboratory Press, pp. 1.29–1.30 (1989).

Sambrook et al., *Molecular Cloning: A Laboratory Manual*, Cold Spring Harbor Laboratory Press, pp. 1.74–1.84 (1989).

Sambrook et al., *Molecular Cloning: A Laboratory Manual*, Cold Spring Harbor Laboratory Press, pp. 18.47–18.59 (1989).

Selhub et al., "Association Between Plasma Homocysteine Concentrations and Extracranial Carotid–Artery Stenosis," *New England J. of Medicine* 32:286–91 (1995).

Shields et al., *J. Nucl. Med.* 33:581–584 (1992).

Soda, "Microdetermination of D–Amino Acids and D–Amino Acid Oxidase Activitiy with 3–Methyl–2–benzothiazolone Hydrazone Hydrochloride," *Analytical Biochemistry* 25:228–235 (1968).

Southern, "Detection of Specific Sequences Among DNA Fragments Separated by Gel Electrophoresis," *J. Mol. Biol.* 98:503–517 (1975).

Southern et al., *J. Mol. Anyl. Genet.* 1:327–341 (1982).

Stampfer et al., "Can Lowering Homocysteine Levels Reduce Cardiovascular Risk?" *New England J. of Medicine* 332:326–329 (1995).

Stampfer et al., *JAMA* 268:877–881 (1992).

Stern et al., "Enhanced In Vitro Selective Toxicity of Chemotherapeutic Agents for Human Cancer Cells Based on a Metabolic Defect," *J. Nat'l Cancer Institute* 76:629–639 (1986).

Tanaka et al., *FEBS Letters* 66:307–311 (1976).

Tarcha in *Polymers for Controlled Drug Delivery*, CRC Press, Boca Raton (1990).

Ueland et al., *Cardiovascular Disease Hemostasis and Endothelial Function*, Marcel Dekler, New York, pp. 183–236 (1992).

Vesclo et al., *Proc. Natl. Acad. Sci. USA* 84:5029–5033 (187).

Wigler et al., "DNA–mediated transfer of the adenine phosphoribosyltransferase locus into mammalian cells," *Proc. Natl. Acad. Sci. USA* 76:1373–1376 (1979).

Young and Davis, "Efficient isolation of genes by using antibody probes," *Proc. Natl. Acad. Sci. USA* 80:1194–1198 (1983).

CH. 1  C.S  2.50  ATT  2  OFFS  0  00/06/00  00:46
A-Z  1-11
     1-10
1-11 1-10
7.90 ─────────────────────── 0.92
880

D-2500                                      00/06/00   00:46

METHOD: TEST        TAG:    43  CH: 1

FILE: 1    CALC-METHOD: AREA %    TABLE:  0  CONC: AREA
NO.      RT       AREA        CONC     OC
 1       7.90      1243        1.321    00
 2       8.92     92993       98.679    00

TOTAL            94230       100.000

PEAK REJ:         500

FIG. 1B

METHODS FOR TREATING AND REDUCING THE POTENTIAL FOR CARDIOVASCULAR DISEASE USING METHIONINASE COMPOSITIONS

RELATED APPLICATIONS

This application is a continuation-in-part of the pending International Application No. PCT/US93/11311 filed Nov. 19, 1993, designating the U.S., which entered the national phase in the U.S. by May 19, 1995, titled "Use of methioninase as an anti-tumor agent in anti-methionine chemotherapy," which is a continuation-in-part of the pending U.S. application Ser. No. 07/979,165, filed Nov. 19 1992, now abandoned, all of which are incorporated by reference (including drawings).

TECHNICAL FIELD

The present invention relates to methioninase compositions, methods of purification of methioninase, and methods of using methioninase in antimethionine and anti-homocysteine chemotherapy. More particularly, the methods of the invention include the use of methioninase in cancer therapy, cardiovascular therapy, and tumor imaging and diagnosis.

BACKGROUND

Therapeutic drug-based treatment of cancer is directed at the use of medicinals which selectively inhibit or kill the cancer cells while not harming normal tissue function beyond acceptable amounts. The difficulty with conventional chemotherapy has been the toxicity of therapeutic drugs for normal tissue.

Many tumors have been shown to have absolute requirement for methionine in a variety of cell types and evaluated tumor tissues, including tumors of the colon, breast prostate, ovary, kidney, larynx melanoma, sarcoma, lung, brain, stomach and bladder as well as leukemias and lymphomas. Methionine dependence has been defined as an inability of tumors to grow when methionine is replaced by homocysteine in the growth medium. See, for example, Chello et al., *Cancer Res.*, 33:1898–1904, 1973; and Hoffman, *Anticancer Res.*, 5:1–30, 1985.

Methionine depletion has been shown to selectively synchronize methionine-dependent tumor cells into late S/$G_2$ phase of the cell cycle. Hoffman et al, *Proc. Natl. Acad. Sci. USA*, 77:7306–7310, 1980. Using the combination of methionine deprivation, followed by repletion of methionine coupled with exposure to an antimitotic agent, termed antimethionine chemotherapy, tumor cells have been selectively eliminated from co-cultures of normal and tumor cells, resulting in cultures of normal cells proliferating vigorously. Stern et al., *J. Natl. Cancer Inst.*, 76:629–639, 1986.

However, in order for methionine-dependent chemotherapy to be conducted in vivo, it is necessary to have a means to effectively deplete serum of circulating methionine. Methionine depletion methods have not been described that reduce circulating methionine levels in vivo in a manner sufficient to be effective in anti-tumor therapies.

Methioninase, an enzyme which degrades methionine, has been purified from a variety of bacterial sources, and has been reported to slow the rate of tumor cell proliferation in vitro. Kreis et al., *Cancer Res.*, 33:1862–1865, and 1866–1869, 1973; Tanaka et al., *FEBS Letters*, 66:307–311 1976; Ito et al., *J. Biochem.* 79:1263–1272, 1976; and Nakayama et al., *Agric. Biol. Chem.* 48:2367–2369, 1984.

Kreis et al., *Cancer Res.* 33:1866–1869, 1973, have described the use of partially purified methioninase at 1150 units/kg/day to inhibit growth of carcinosarcoma cells implanted in a mouse model. Although the enzyme reduced primary tumor cell growth, it was not reported to reduce the T/C (treated versus control) ratio of tumor diameter below 50%, and was not reported to have any effect on metastasis. The authors also indicated that tumor specificity of the methioninase cannot be expected without other unspecified interventions, and further do not comment on the possible endotoxin content of a partially purified enzyme or its effect on mice. The only toxicity studies reported were absence of animal body weight loss after the duration of the treatment, and negative gross examination for toxicity. Further, the authors report that the enzyme had a serum half life of 4 hours.

Kreis et al., *Cancer Res.* 33:1866–1869, 1973, further reported the use of a methionine-free diet as a means to deplete methionine as an anti-tumor therapy. However, the authors reported that the diet did not slow tumor growth as effectively as the use of methioninase and resulted in the undesirable side effect of continuous loss of weight of the animal. The authors did not report the use of methionine deficient diets combined with methioninase treatment, and did not study cell synchronization.

There continues to be a need for an effective methionine-dependent chemotherapy of tumors directed at effectively reducing the amount of methionine as to provide a beneficial anti-tumor effect without deleterious injury.

BRIEF DESCRIPTION OF THE INVENTION

It has now been discovered that methioninase can deplete levels of methionine in mammals without harm, can be effectively used to selectively inhibit tumor growth, and further can be used to selectively arrest and thereby synchronize tumor cells for antimitotic chemotherapy.

It has also been discovered that methionine depletion is most effective when several different methods are used synergistically to substantially reduce effective methionine levels. These methods include methionine starvation using methionine-free diet, competitive inhibition of methionine by use of inhibitors that compete with methionine for methionine-utilizing enzymes, and combinations thereof.

Thus, the invention describes a method for inhibiting tumor cell growth comprising contacting a population of tumor cells with a therapeutically effective amount of methioninase for a time period sufficient to induce cell cycle stasis in cells of the population, and form static tumor cells. By "contacting" is meant that the therapeutic compositions of the present invention are placed in close enough proximity to the targeted tumor such that a tumor-inhibiting effect is observed, or that the therapeutic compositions are placed in a medium, such as a nutrient medium or blood, such that the level of methionine in the medium is decreased to a level where the growth of tumor cells in the medium are inhibited. By "static" tumor cells is meant tumor cells that are growth inhibited. The method can be practiced in vitro or in vivo. The contacting of the tumor cells does not need to be direct and may be executed by contacting the nutrient medium containing the tumor cells, either in vitro or in vivo. The contacting may also be accomplished by contacting circulating blood with methioninase. Such circulating blood may or may not contain tumor cells as the tumors may be solid tumors that do not circulate. By "inhibiting tumor cell growth" is meant that administration of the compound of the invention reduces the growth of a tumor, as measured by, for example, size, by 10% to 100%, more preferably by 34% to 79%, and more preferably by 55% to 68% when compared to a tumor that has not been treated with the compound.

The therapeutic compositions of the present invention are useful as reagents in anti-methionine and anti-homocysteine chemotherapy. Specifically, methioninase is used as an anti-tumor reagent to slow or stop cell division by depleting methionine. This effect can be enhanced with competitive inhibitors of methionine. In addition, methioininase can be used in combination with anti-mitotic and other cell-cycle specific cytotoxic agents to increase the therapeutic effectiveness of the antimitotic or other cell-cycle specific cytotoxic agents by inducing cell cycle synchronization. Methioninase is also used in homocysteine depletion chemotherapy to reduce the risk of and to treat cardiovascular disease. Methioninase is also used to deplete blood and tumor $[^{12}C]$ methionine prior to repletion with $[^{11}C]$ methionine to detect and diagnose tumors in the body at ultra-high resolution.

In one embodiment, the tumor cells are first subjected to a methionine-starvation step to first reduce the level of methionine. Optionally, the methionine starvation may be accompanied by homocysteine to reduce toxicity to normal cells, thereby increasing the specificity of the therapy.

Another related aspect of the present invention features the use of the present methionine-depletion methods to arrest tumor cells in late $S/G_2$ phase of the cell cycle, followed by treatment to synchronously initiate cell-cycling and the administration of a cell cycle-specific cytotoxic agent such as an antimitotic to selectively and effectively kill tumor cells. Those of ordinary skill in the art are familiar with cell cycle-specific cytotoxic agents that are toxic to cells of particular phases of the cell cycle. The method comprises the steps of:

(a) contacting the static tumor cells produced by the previous methionine-depletion step with a cell cycle-inducing amount of methionine to initiate cell-cycling of the static tumor cells forming cycling cells, and (b) contacting the cycling cells with a cell cycle-specific cytotoxic agent in an amount sufficient to inhibit mitosis of the mitotic cells, thereby inhibiting tumor cell growth.

In the preferred embodiment, the method comprises the steps of (a) contacting the static tumor cells produced by the previous methionine-depletion step with a cell cycle-inducing amount of methionine to initiate mitosis of the static tumor cells forming mitotic cells, and (b) contacting the mitotic cells with an anti-mitotic agent in an amount sufficient to inhibit mitosis of the mitotic cells, thereby inhibiting tumor cell growth.

The invention also features a histoculturing method for determining solid tumor cell responsiveness to methionine depletion therapy comprising:

(a) histoculturing a non-disaggregated solid tumor sample comprising organized tumor cells;

(b) contacting the solid tumor sample under histoculturing conditions with a preselected amount of a methionine-depleted medium for a time period sufficient to induce cell cycle stasis in cells of the sample, and form static tumor cells;

(c) determining the effect of the contacting upon the tumor cells, thereby determining solid tumor cell responsiveness.

In preferred embodiments, the histoculture method is used to assess responsiveness of a tumor to the combined therapy of methionine depletion and subsequent treatment with an antimitotic. Therefore, the method further comprises the steps of:

(i) contacting the static tumor cells under histoculturing conditions with a cell cycle-inducing amount of methionine to initiate mitosis of the static tumor cells forming mitotic cells, and (ii) contacting the mitotic cells under histoculturing conditions with an anti-mitotic agent in an amount sufficient to inhibit mitosis of the mitotic cells.

Also featured are therapeutic compositions for methionine depletion therapy comprising a therapeutically effective amount of substantially isolated methioninase having a specific activity of at least about 10 to 20 units methioninase activity per milligram (mg) protein and 1–100 ng of endotoxin per mg protein. In the preferred embodiment, the therapeutic composition contains less than 10 nanograms endotoxin per mg protein, together with a pharmaceutically acceptable carrier.

The therapeutic compositions of the present invention also include an endotoxin-free methioninase. In a preferred embodiment, the methioninase is prepared using a novel and efficient method from *Pseudomonas putida* grown under improved fermentation conditions. The present invention also provides a method of isolating an improved, high-methioninase-producing strain of *P. putida*.

The methioninase compositions of the present invention are also provided in a chemically modified form by coupling of the methioninase to polymers such as polyethylene glycol (PEG). The PEG-modified methioninase of the present invention exhibits high methionine depletion activity, an extended half-life, and low immunogenicity.

The invention also features the use of methioninase to lower homocysteine levels in patients to reduce the risk of, and to treat, cardiovascular diseases.

The invention provides a method of depleting methionine by administration of methioninase for tumor diagnosis and imaging.

Those of ordinary skill in the art will recognize that the uses of methioninase described herein are not limited to the use of a particular methioninase as purified herein. The compositions and methods of the present invention include within their scope methioninase that is purified from any source, including the bacterial source specifically used as an example herein. Therefore, "methioninase" as used herein includes methioninase purified from any source. Preferably, the source is *P. putida*, and the methioninase is purified according to the purification methods described herein. The use of methioninase in the methods of the present invention is also not limited to the preparation of methioninase that is specifically described. The examples of methioninase purification provided herein describe the preferred methioninase extraction methods and are not intended to limit in any way the scope of the present invention.

Other features, advantages and related embodiments of the present invention will be apparent based on the disclosures contained herein.

BRIEF DESCRIPTION OF THE DRAWINGS

FIG. 1 illustrates the results of methioninase purification. FIG. 1b illustrates the results of HPLC analysis of the pooled purified methioninase fractions eluted from the second anion exchange column.

Figure 1A:
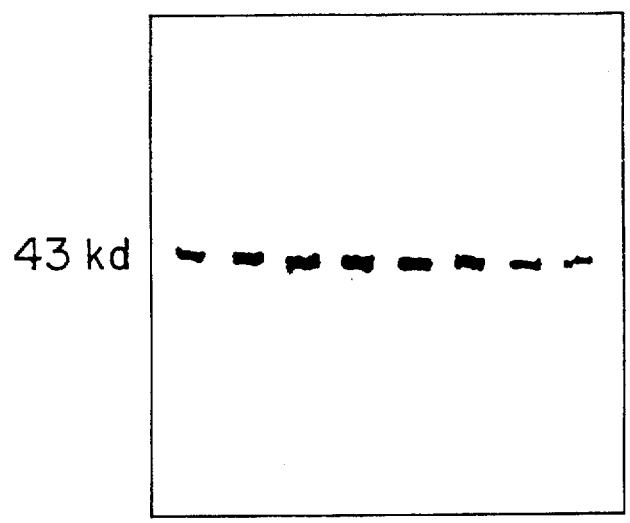
FIG. 1a picture of a SDS-PAGE gel depicting the purity of fractions eluted from the second anion exchange column of Method 3.

The drawings are not necessarily to scale, and certain features of the invention may be exaggerated in scale and shown in schematic form in the interest of clarity and conciseness.

DESCRIPTION OF THE INVENTION

A. Definitions

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.* 243:3552–59, 1969, and adopted at 37 C.F.R. 1.822(b)(2)), hereby incorporated by reference.

| TABLE OF CORRESPONDENCE | | |
|---|---|---|
| SYMBOL | AMINO ACID | |
| 1-Letter | 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

"Vector" refers to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors" Particularly important vectors allow convenient expression of a methioninase protein of this invention.

B. Methods For Using Methioninase as an Antitumor Agent

I. Methionine Depletion

Methioninase is used herein as an antitumor agent in a variety of modalities for substantially depleting methionine from a tumor cell, tumor tissue or the circulation of a mammal with cancer, or for depletion of methionine where its depletion is considered desirable, as described further herein.

Whereas prior methods can reduce the levels in vivo of methionine to no lower than about 35 micromolar (uM), no methods are known which can safely, easily and rapidly reduce methionine levels substantially below about 10 uM. By substantially is meant at least detectably below 10 uM, preferably less that 1 uM, more preferably less than 0.1 uM, and most preferably to non-detectable levels, using conventional methionine detection methods. Methionine can be measured in aqueous solutions, including body fluids such as blood, plasma and serum, by a variety of methods. An exemplary method is reverse-phase FPLC using methionine standards.

Depletion can be conducted in vivo, in the circulation of a mammal, in vitro in cases where methionine depletion in tissue culture or other biological mediums is desired, and in ex vivo procedures where biological fluids, cells or tissues are manipulated outside the body and subsequently returned to the body of the patient mammal.

Depletion of methionine from circulation, culture media, biological fluids or cells is conducted to reduce the amount of methionine accessible to the material being treated, and therefore comprises contacting the material to be depleted with a methionine-depleting amount of methioninase according to the present invention under methionine-depleting conditions as to degrade the ambient methionine in the material being contacted.

Because tumor cells are dependent upon their nutrient medium for methionine, the depletion may be directed to the nutrient source for the cells, and not necessarily the cells themselves. Therefore, in an in vivo application of the present invention, the methioninase can be contacted with the nutrient medium for a population of tumor cells. In this embodiment, the medium can be blood, lymphatic fluid, spinal fluid and the like bodily fluid where methionine depletion is desired.

A methionine-depleting amount can vary widely depending upon the application, and typically depends upon the amount of methionine present in the material, the desired rate of depletion, and the tolerance of the material for exposure to methioninase. Methionine levels in a material, and therefore rates of methionine depletion from the material, can readily be monitored by a variety of chemical and biochemical methods well known in the art. Exemplary methionine-depleting amounts are described further herein, and can range from 0.001 to 100 units (U) of methioninase, preferably about 0.01 to 10 U, and more preferably about 0.1 to 5 U methioninase per milliliter (ml) of material to be treated.

Methionine-depleting conditions are buffer and temperature conditions compatible with the biological activity of the methioninase enzyme, and include moderate temperature, salt and pH conditions compatible with the enzyme. Exemplary conditions include about 4–40 degrees Centigrade (°C.), ionic strength equivalent to about 0.05 to 0.2M NaCl, and a pH of about 5 to 9, although physiological conditions are preferred.

In a preferred embodiment, the invention contemplates methods of using methioninase as an antitumor agent, and therefore comprises contacting a population of tumor cells with a therapeutically effective amount of methioninase for a time period sufficient to induce cell cycle stasis in cells of the population, and form static tumor cells.

As described herein, the placement of tumor cells in cell cycle stasis is desirable for a variety of reasons, including but not limited to, selectively slowing tumor growth, killing tumor cells by maintaining the cells in stasis for such prolonged time periods as to produce cell death, and preparation of a population of tumor cells for cell cycle synchronization prior to a subsequent chemotherapeutic treatment, and the like.

The time period required to induce cell cycle stasis by contact with methioninase depends on several factors, such as the amount of methioninase contacted with the cells or the medium containing the cells, the amount of methionine, specific activity of the enzyme, temperature and other reaction conditions affecting reaction rate, and the like parameters readily controllable by the practitioner. Typical time periods are 10 minutes to about 30 days, preferably about 1 hour to 20 days, and more preferably about 1 to 10 days.

Cell cycle stasis is a condition in which the cell is not dividing nor cycling through the full cycle of events, the phases being individually referred to as $G_0$, $G_1$, $G_2$ and S phases. Upon methionine depletion, it is believed that the cell stops cycling in the late $S/G_2$ phase as evidenced by the accumulation of DNA relative to normal resting cells. Methods for identifying cell cycle stasis can be determined by a variety of histological methods, and can be evaluated by cell culture, and involve measuring DNA content of a population of cells as described in the Examples.

Tumors for which the present treatment methods are useful include any malignant cell type such as is found in a solid tumor or a hematological tumor. Exemplary solid tumors can include, but are not limited to a tumor of an organ selected from the group consisting of pancreas, colon, cecum, stomach, brain, head, neck, ovary, kidney, larynx, sarcoma, lung, bladder, melanoma, prostate and breast. Exemplary hematological tumors include tumors of the bone marrow, T or B cell malignancies, leukemias, lymphomas, blastomas, myelomas, and the like.

In one embodiment, the contacting in vivo is accomplished by administering, by intravenous or intraperitoneal injection, a therapeutically effective amount of a physiologically tolerable composition containing methioninase of this invention to a patient, thereby depleting the circulating methionine source of the tumor cells present in the patient. The contacting of methioninase can also be accomplished by administering the methioninase into the tissue containing the tumor cells.

A therapeutically effective amount of a methioninase is a predetermined amount calculated to achieve the desired effect, i.e., to deplete methionine in the tumor tissue or in a patient's circulation, and thereby cause the tumor cells to stop dividing.

Thus, the dosage ranges for the administration of methioninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of a methioninase of this invention is typically an amount such that when administered in a physiologically tolerable composition is sufficient to achieve a intravascular (plasma) or local concentration of from about 0.001 to about 100 units (U) per ml, preferably above about 0.1 U, and more preferably above 1 U methioninase per ml. Typical dosages can be administered based on body weight, and are in the range of about 5–1000 U/kilogram (kg)/day, preferably about 5–100 U/kg/day, more preferably about 10–50 U/kg/day, and more preferably about 20–40 U/kg/day.

In preferred methods, a methioninase used is substantially free of endotoxin, as discussed further herein. Particularly preferred is the use of methioninase produced herein that is substantially free of endotoxin.

The methioninase can be administered parenterally by injection or by gradual infusion over time. Methioninase can be administered intravenously, intraperitoneally, orally, intramuscularly, subcutaneously, intracavity, transdermally, dermally, can be delivered by peristaltic means, or can be injected directly into the tissue containing the tumor cells or can be administered by a pump connected to a catheter that may contain a potential biosensor or methionine.

The therapeutic compositions containing methioninase are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of methioninase and conversely low serum and tissue levels of methionine. Alternatively, continuous intravenous infusion sufficient to maintain concentrations in the blood in the ranges specified for in vivo therapies are contemplated.

II. Methionine Depletion Methods

In practicing the present methods, methionine depletion by contacting a methionine-containing material with methioninase as described earlier can be accompanied by one or more supplementary methionine depletion steps. Furthermore, the invention contemplates a variety of treatment procedures where the depletion of methionine is desirable, as described further herein.

a. Methionine Starvation

For example, a methionine starvation step may be used to first reduce the ambient levels of methionine, wherein the starvation step involves contacting the tumor cell(s) with methionine-free nutrients for a methionine starvation time period that is conducted prior to or during the methioninase contacting step. A methionine starvation step may comprise the use in vitro of methionine-deficient medium, i.e., medium with low levels or no methionine, or the use in vivo of a methionine-free diet. Methionine-free media are well known in the tissue culture arts. An exemplary medium is Eagle's minimal essential medium (lacking methionine and choline chloride) with nonessential amino acids, such as is available from GIBCO. Methionine deficient amino acid diet foods are also commercially available, including diet TD 92077 available from Teklad, Inc.

The time period for a methionine starvation step can vary widely depending on the particular application, and is a time period sufficient for cell culture, tissue or vascular concentrations of methionine to decrease to a lower level, and stop any further substantial decrease in level. Typical time periods can be from about 6 hours to about 2 months, preferably about 1 day to 2 weeks.

Because methionine is an essential amino acid, it is to be understood that many applications of the present methods can be somewhat toxic to normal cells. However, as described herein, normal and tumor cell metabolize the methionine precursor homocysteine differently, such that homocysteine can supplement methionine deficiencies in normal cells while not rescuing methionine dependencies of tumor cells.

Thus, in a related embodiment the invention contemplates a method using a methionine-deficient nutrient (medium or diet) which may be supplemented with a methionine precursor such as homocysteine, or an analog thereof, used by normal cells to provide necessary nutritional supplements. Homocysteine can be added to nutrient medium at a concentration of about 5 to about 200 micromolar (uM), preferably about 10 to about 100 uM.

Preferred methionine precursors useful in this embodiment include L-homocysteine-thiolactone, homocysteine, and 4-methylthio-2-oxobutanoic acid.

Thus, in one embodiment, the invention comprises the step of feeding a mammal with a methionine deficient diet for a time period to deplete the intravascular concentrations of methionine. The diet may optionally contain methionine precursors as a methionine supplement. Alternatively, the methionine precursor may be administered by injection or other routes as is well known. Preferred daily dosages of homocysteine as a dietary supplement are about 5 to about 1000 mg homocysteine per kilogram mammal body weight per day.

The routes of administration of the homocysteine are typically the same as the methioninase to be added, and depend on the target tissue for delivery of the supplement.

b. Competitive inhibitors of Methionine Utilizing Enzymes

Following the observations described in the Examples, it has been further discovered that competitive inhibitors of methionine-utilizing enzymes are useful to synergistically increase the effectiveness of methionine depletion methods described herein. Thus the invention contemplates the use of a methionine starvation step that further comprises contacting the tumor cells with an amount of a competitive inhibitor of methionine for a time period sufficient to inhibit methionine metabolism by a methionine-utilizing enzyme. Methionine-utilizing enzymes useful for directing competitive inhibitors include methionine decarboxylase and methionine adenosyltransferase.

Preferably, the time period required to inhibit methionine is the duration of the methionine starvation time period itself.

Competitive inhibitors of methionine compete with methionine as a substrate for methionine-utilizing enzymes, and therefor act to inhibit any normal metabolic effect that endogenous methionine might produce by direct competition, i.e., inhibits methionine metabolism. Where the cell requires methionine and the attendant metabolism of methionine, the competitive inhibitor acts to reduce the metabolism of methionine, necessitating higher methionine concentrations to yield the same effect observed where no inhibitor is present.

A competitive inhibitor of methionine can be any methionine derivative that functions as a classic competitive inhibitor. Typical competitive inhibitors include alkyl derivatives of methionine (i.e., alkylthionines), as where the methyl group of methionine is replaced with an ethyl group (ethionine), a propyl group (propthionine), a butyl group (buthionine), or a pentyl group (penthionine).

Also contemplated as useful methionine competitive inhibitors are cycloleucine and halogenated methionines. A typical halogenated methionine is selected from the group consisting of fluoromethionine, chloromethionine, bromomethionine and iodomethionine. Thus a contemplated competitive inhibitor of methionine is selected from the group consisting of alkylthionine, cycloleucine and a halogenated methionine, wherein said alkylthionine is not methionine.

An amount of a competitive inhibitor of methionine effective to competitively inhibit methionine is an amount to produce a reduction in the effective concentration of methionine. This amount is typically a molar excess relative to the methionine present, as shown in the Examples. Typically, this amount of inhibitor is in the range of a 10 to 1000 fold molar excess relative to the methionine concentration in the medium where methionine is to be competed, preferably at least a 20 fold molar excess, and more preferably at least a 50 fold molar excess. Where the inhibitor is to be used in vivo, the dosage is typically about 5–30 mg per kg of animal body weight, preferably about 25 mg/kg, as shown herein.

The amount of inhibitor required for effectiveness may vary depending upon the amount of endogenous methionine present at the time the inhibitor is administered. This relationship between concentration of methionine and effective concentration of inhibitor is demonstrated by the dosage titration results shown in the Examples, and is defined by classic reaction rate theory for competitive inhibitors. Typical amounts of inhibitor are from about 10 uM to about 1 mM.

Furthermore, the amount of effective inhibitor can be predetermined by the in vitro histoculture methods described herein, to first establish the effective conditions in a particular tumor tissue for methionine depletion by any of the methods described herein, followed by a determination of the effective concentration of the inhibitor.

The inhibition of methionine metabolism by use of a competitive inhibitor of methionine can be monitored by a variety of indicators, including the indicators described in the Examples. These indicators include histoculture of a tissue to measure DNA content as an indicator of cell cycle arrest, and increased inhibition of growth of tumor tissue in a mouse fed a methionine-free diet. Other indicators will be apparent to one skilled in the art.

c. Synergistic Effect of Using Multiple Methionine Depletion Methods—Anti-Methionine Chemotherapy In one embodiment, the present invention contemplates the use of multiple methods for methionine depletion, generally referred to as anti-methionine chemotherapy, to take advantage of the synergy that occurs when two or more different methods for methionine depletion are used.

Methionine depletion methods described herein include (1) methionine starvation using methionine-free medium (in vitro) or diet (in vivo), (2) exposure to methioninase to enzymatically deplete endogenous methionine levels, (3) competitive inhibitors of methionine to reduce the effective concentration of endogenous methionine, particularly in combination with methods (1) and (2) above, where methionine levels are already reduced, and (4) use of methionine precursors, such as homocysteine described herein, to increase the selectivity of any of the other three methionine depletion methods for tumor cells.

Thus, anti-methionine chemotherapy methods described herein for methionine depletion can be conducted by any of a variety of combinations of the above identified methods, including (1) plus (2), (1) plus (3), (2) plus (3), (1) plus (2) plus (3), and any of these four combinations plus (4).

Particularly preferred for maximum depletion of methionine and its resultant metabolites is the use of methionine-free diet but containing methionine precursors, plus the use of a competitive inhibitor of methionine and methioninase.

III. Enhancement of Anti-Mitotic Tumor Therapy

In another embodiment, the invention contemplates the use of methionine-depletion methods described herein in methods for increasing (enhancing) the potency and selectivity of conventional chemotherapies, and preferably the selectivity of antimitotic drugs used for cancer therapy.

The key purpose for use of methionine-depletion steps in combination with conventional antimitotic therapies is to take advantage of the fact that methionine depletion selectively and specifically stops tumor cell proliferation prior to mitosis, such that upon repleting the cell, tissue, medium or vasculature with methionine, the static cells synchronously begin cell cycling, into mitosis rendering the population of cells to be uniformly proliferating and susceptible to the effects of cell-cycle specific chemotherapy. To cause the tumor cells to enter cell stasis, any cell cycle cytotoxic agent may be used. Such agents are well known to those of ordinary skill in the art. In a preferred embodiment, the cell-cycle cytotoxic agent is an anti-mitotic agent.

Thus, in a preferred embodiment, the present invention contemplates an anti-tumor chemotherapeutic method comprising the methionine-depleting step described herein to form static tumor cells followed by the additional steps of:

(a) contacting the static tumor cells with a cell cycle-inducing amount of methionine to initiate mitosis of the static tumor cells, thereby forming mitotic cells, and (b) contacting the mitotic cells with an anti-mitotic agent in an amount sufficient to inhibit mitosis of the mitotic cells, thereby inhibiting tumor cell growth.

Methionine, methionine salts and functional equivalents thereof that function to initiate cell cycling of a static cell are referred to as cell cycle inducing agents, and can be used together or alternatively as the reagent for initiating cell cycling and mitosis in one or more static cells in the methionine-depleted tumor cell population.

A cell-cycle inducing amount of a cell cycle-inducing agent is an amount that initiates cell cycling in at least a few (10%), preferably a majority, and more preferably at least 90% of the static cells in the methionine-depleted tumor cell population. The initiation and extent of cell cycling can readily be measured by use of histological or metabolic markers. For methionine, a cell-cycle inducing amount is typically in the range of about 1 micromolar (uM) to about 2.5 millimolar (mM), and preferably about 10 to 250 uM. S-phase-specific drugs can similarly be used to attack any tumor cells still in S-phase when methionine is repleted.

Routes of contacting (administration) of the cell cycle inducing agent with the static tumor cells can vary but typically will be the same routes as used for administering methioninase or competitive inhibitors as described herein.

The timing and time periods for contacting the static tumor cells with a cell-cycle inducing agent can vary depending on the tumor, and other considerations that can be determined empirically, such as by the histoculture methods described herein. The cycle-inducing agent can be added prior to or substantially simultaneously with the antimitotic agent. It may be advantageous to add the inducer prior to the antimitotic agent where it has been determined that the particular antimitotic is fast acting, and cell cycle induction is slow. These parameters may depend upon the particular tumor type, tissue location, choice of antimitotic and the like. Furthermore, optimization of variables such as timing, dosage and drug choice can be readily carried out by a variety of methods prior to in vivo administration of the therapeutic methods. A preferred optimization procedure is to use the exemplary histoculture assay system described herein.

The timing for contacting an anti-mitotic agent depends upon the induction of cell cycling of the static tumor cells. Typically, anti-mitotic agents can be contacted with the mitotic cells at any time during cycling, and as soon as the cells became mitotic. For some tumor cell populations, this event may occur rapidly after addition of the inducer agent, allowing simultaneous or near simultaneous addition of both inducer and anti-mitotic agent to the static tumor cells. Alternatively, the anti-mitotic may be added about 1 hour to 30 days after inducer, but preferably within about one or two days of induction.

The anti-mitotic agent or other cell-cycle specific agent used herein can be any agent exhibiting cell toxicity based on mechanisms directed at cell proliferation, mitosis or cell cycling. Thus anti-mitotic agents can include any of a variety of compounds which are anti-metabolites or which otherwise exhibit toxicity for dividing (mitotic) cells. Preferred clinical pharmacology of a anti-mitotic agent for use in the present methods is inhibition of cell mitotic activity, inhibition of nucleic acid synthesis, alkylating agents, antibiotics, alkaloids, and the like antitumor agents. Insofar as the field of pharmacology is constantly advancing, it is to be understood that the invention is to not be limited to presently known anti-mitotic and other cell-cycle specific agents, but rather to include the use of equivalents of known compounds, newly discovered or developed compounds and the like agents exhibiting the requisite activity.

Exemplary alkylating agents include cyclophosphamide (CTX; cytoxan), chlorambucil (CHL; leukeran), cisplatin (CisP; platinol) busulfan (myleran), melphalan, carmustine (BCNU), streptozotocin, triethylenemelamine (TEM), mitomycin C, and the like alkylating agents.

Exemplary anti-metabolites include methotrexate (MTX), etoposide (VP16; vepesid) 6-mercaptopurine (6MP), 6-thiocguanine (6TG), cytarabine (Ara-C), 5-fluorouracil (5FU), dacarbazine (DTIC), and the like anti-metabolites.

Exemplary antibiotics include actinomycin D, doxorubicin (DXR; adriamycin), daunorubicin (daunomycin), bleomycin, mithramycin and the like antibiotics.

Exemplary alkaloids include vinca alkaloids such as vincristine (VCR), vinblastine, and the like.

Other antitumor agents include taxol and taxol derivatives, the cytostatic agents glucocorticoids such as dexamethasone (DEX; decadron) and corticosteroids such as prednisone, nucleoside enzyme inhibitors such as hydroxyurea, amino acid depleting enzymes such as asparaginase, and the like diverse antitumor agents.

The synthesis and formulation of the above anti-mitotic (cytotoxic) agents is well known, is described in a variety of sources, and therefore will not be repeated here. Exemplary sources for synthesis and formulations of the above agents include *Physician's Desk Reference*, Barnhart, eds., Medical Economics Company, Inc., Oradell, N.J., 1992; and *Merck index*, 11th Edition, Merck & Co., 1989.

The use of cytotoxic agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using the present histoculture methods. Generally, the dosage will be reduced compared to the amount used in the absence of synchronized cell cycling, as shown by the present disclosures.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgement of the physician, the condition of the patient, and the effectiveness of the therapeutic method based on the in vitro responsiveness of the primary cultured malignant cells or histocultured tissue sample, or the responses observed in the appropriate animal models.

IV. Gene Therapy

In another embodiment, the invention contemplates the use of a rDNA for expression of methioninase within the tissue or lymphocytes surrounding the tissue to be treated according to the methioninase contacting methods of the invention. To that end, it is contemplated that the methioninase enzyme is presented for the contacting step by the expression of a regulatable methioninase expressing gene, thereby producing the methioninase gene product.

As described earlier, there are a large variety of suitable expression vectors presently known for expressing methioninase which can be used. In preferred embodiments, the expression of the methioninase gene is regulatable. Thus an expression vector has a second nucleotide sequence operatively linked to the first methioninase encoding sequence which defines a means for regulating the expression of the methioninase gene. An exemplary means is an inducible promoter.

Preferred inducible promoters are responsive to a component that can be added to the culture medium, or readily penetrate into a host cell containing the gene for expressing the methioninase gene.

Thus, the invention also contemplates a methionine depleting method wherein the contacting of methioninase with a population of tumor cells comprises the steps of:
(i) introducing an expression vector into a sample of the said tumor cells or into tumor infiltrating lymphocytes or their bone marrow precursors, wherein the expression vector has a nucleotide sequence that encodes methioninase and is capable of regulated expression of methioninase, and has a nucleotide sequence that provides a means for regulating the expression of methioninase, to form methioninase gene transfected cells;
(ii) contacting the tumor cells in vivo with the methioninase gene transfected cells; and
(iii) expressing the methioninase-encoding nucleotide sequence in the transfected cells, thereby producing methioninase in the transfected cells and thereby contacting tumor cells with the produced methioninase. By "introducing" is meant any method known by those of ordinary skill in the art to insert the expression into the target cells in a manner wherein the gene contained within the expression vector may be expressed by the target cell. Such "introducing" may be accomplished by, for example, transfection, transformation, or viral infection.

Transfection of tumor cells, either adherent cells or cells in suspension, can be accomplished by a variety of known transfection methods. Thereafter, the transfected cell is reintroduced into the host and allowed to locate in the native, relevant, vicinity of tissue to be treated, thereby contacting the transfected cells with the tumor cells to be treated. Introduction of methioninase to transfected cells can be accomplished by a variety of means, but generally requires the presence of a selectable marker.

In preferred embodiments, the means for regulating the expression of the gene is an inducible promoter that is responsive to a reagent that can be added to the medium. Exemplary is the metallothionine promoter.

The cells to be transfected can be a sample of the tumor cells, or normal immune cells such as tumor infiltrating cells, such as tumor infiltrating lymphocytes or bone marrow precursors of the bone marrow, such as hematopoietic stem cells or progenitor cells.

C. Therapeutic Compositions

In another embodiment, the present invention contemplates therapeutic compositions comprising a therapeutically effective amount of substantially isolated methioninase, together with a pharmaceutically acceptable carrier.

L-Methioninase (L-methionine-alpha-deamino-gamma-mercaptomethane-lyase or methioninase) is an enzyme that degrades methionine by deamination and dethiomethylation. Methioninase activity can be measured at least by measuring the amount of alpha-ketobutyrate formed upon cleavage of methionine. One unit (U) of methioninase is defined as an amount of enzyme that produces 1 micromole of alpha-ketobutyrate per minute from methionine under the standard assay conditions described by Ito et al., *J. Biochem.*, 79:1263–1272, 1976; and Soda, *Analyt. Biochem.* 25:228–235, 1968.

Methioninase can be prepared from a variety of sources, including being isolated directly from bacteria cultures, or being expressed from a recombinant DNA molecule encoding a methioninase protein.

Bacterial sources of methioninase include *Pseudomonas putida*, *Pseudomonas ovalis*, *Aeromonas sp.*, and *Clostridium sporogenes* and any other potential sources of methioninase. *P. putida* and *C. sporonenes* are commercially available from the ATCC and have accession numbers ATCC 8209 and ATCC 7955, respectively. The other bacteria are generally available from the academic research community. Purification of methioninase has been described by a variety of methods. See, for example, Kreis et al., *Cancer Res.*, 33:1862–1865, 1973; Tanaka et al., *FEBS Letters* 66:307–311, 1976; Ito et al., *J. Biochem.* 79:1263–1272, 1976; Nakayama et al., *Agric. Biol. Chem.* 48:2367–2369, 1984; and Soda, *Analyt. Biochem.* 25:228–235, 1968. An exemplary purification procedure is described in the Examples.

A preferred methioninase has a specific activity of about 1–50 units (U) per mg protein. Typical preparations of purified methioninase are described herein having a specific activity of about 2–20 U/mg. The assay of methioninase to determine specific activity can be conducted by a variety of methods, such as is described in the Examples.

A preferred methioninase is preferably substantially isolated. By substantially isolated is meant that the enzyme is at least 50% pure by weight, preferably at least 90% pure, and more preferably at least 99% pure, or essentially homogeneous. A preferred protein is essentially homogeneous when analyzed on electrophoretic media such as polyacrylamide gel electrophoresis (PAGE). Homogeneous on PAGE means only a single detectable band.

A preferred methioninase is substantially free of endotoxins, such as bacterial lipopolysaccharides, due to the undesirable side effects associated with endotoxins when physiologically contacted in a mammal, as by i.v. or i.p. administration. By substantially free is meant less than about 10 nanograms (ng) endotoxin per milligram (mg) methioninase protein, preferably less than 1 ng endotoxin per mg methioninase, and more preferably less than 0.1 ng endotoxin per mg methioninase. The assay of endotoxin is well known in the therapeutic arts, and can be conducted by any of variety of methods. A preferred method is described in the Examples.

A preferred methioninase is heat stable, so as to increase its shelf life and effectiveness when utilized under conditions of elevated temperatures, such as in vivo in an animal body. By heat stable is meant that the enzyme can be exposed to 60 degrees Centigrade (60 C.) for 10 minutes and retain 80%, preferably retain 90%, and more preferably retain 95% of its specific activity.

A preferred methioninase exhibits a serum half-life of at least 5 hours, preferably 6 hours, and more preferably at least 7 hours.

Particularly preferred is methioninase prepared from *P. putida*, *P. putida* methioninase exhibits an apparent molecular weight when analyzed on PAGE-SDS under denaturing conditions of about 43 kilodaltons. A preferred method of purifying methioninase is described in the Examples.

Thus a therapeutic composition comprises a physiologically tolerable carrier together with substantially isolated methioninase, dissolved or dispersed therein as an active ingredient. In a preferred embodiment, the therapeutic composition is not immunogenic when administered to a human patient for therapeutic purposes. One embodiment of the present invention features a methioninase that is chemically modified comprising methioninase conjugated to a polymer. Preferably, the methioninase is substantially isolated and substantially endotoxin free. By "chemically modified" is meant any form of methioninase that is changed to a form that is different than the methioninase purified from nature. Preferably, the methioninase is chemically modified by linking the methioninase to a polymer.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal or human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Particularly preferred are phospholipid and liposome compositions as described herein. In addition, a therapeutic amount of methioninase can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of methioninase, typically an amount of at least 0.1 weight percent of active protein per weight of total therapeutic composition, and preferably is at least about 25 weight percent. A weight percent is a ratio by weight of methioninase protein to total composition. Thus, for example, 0.1 weight percent is 0.1 grams of methioninase per 100 grams of total composition.

Insofar as a methioninase composition can be used in vivo intravascularly, it is contemplated in one embodiment to formulate a therapeutic composition for controlled delivery of the methioninase, and optionally to shield the methioninase protein from degradation and other phenomenon which would reduce the serum half-life of therapeutically administered methioninase.

Thus, in one embodiment, the invention contemplates therapeutic compositions containing delivery vehicles such as polymers, polymeric vehicles, particulates, latexes, coacervates, ion-exchange resins, liposomes, enteric coatings, mediators, bioadhesives, microcapsules, hydrogels, and the like vehicles. Exemplary drug delivery vehicles including liposomes are described at least by Tarcha in "Polymers For Controlled Drug Delivery", CRC Press, Boca Raton, 1990.

Methioninase is preferably purified in a four step procedure described in the Examples. The method comprises the steps of:

a) heating a bacterial cell extract that contains methioninase in aqueous buffers with pyridoxal phosphate at 55–65 degrees Centigrade for 5 to 20 minutes;

b) subjecting the heated extract to DEAE ion exchange chromatography in low ionic strength (10–50 mM) KCl at pH 7.0–7.6, and collecting fractions containing methioninase eluted in a 40–300 mM KCL gradient;

c) subjecting said collected fractions to DEAE ion exchange chromatography in medium ionic strength (120–180 mM) KCl at pH 8.0–8.6, and collecting fractions containing methioninase eluted in a phosphate buffered 0.5M NaCl; and d) contacting said fractions collected in step (c) with a chromatography medium capable of adsorbing endotoxin, and collecting the eluant, thereby removing endotoxin from said eluant to form endotoxin-free methioninase having at least 2 units methioninase activity per milligram protein and from 1–100 ng of endotoxin per mg protein.

In the preferred embodiment, the endotoxin-free methioninase contains less than 10 nanograms (ng) endotoxin per milligram protein.

In preferred embodiments, the cell extract is prepared from a preferred bacterial source as recited herein, particularly P. putida. The extracts are generally prepared by harvesting and washing bacterial cell cultures to form a cell paste/pellet, depending upon whether harvesting is by centrifugation or by hollow fiber filtration, which methods are generally well known. The pellet is flooded with cold (−20 C.) acetone, filtered, and dried to form an acetone powder. The extract is prepared by suspending the powder in aqueous buffers containing pyridoxal phosphate (5–50 mM, preferably 10 mM) and other typical stabilizers, including but not limited to beta-mercaptoethanol, EDTA and protease inhibitors.

In further preferred embodiments after fermentation of the bacteria, the bacteria are collected by centrifugation and homogenized to form a suspension.

The resulting suspension is heated to precipitate selective proteins and other insoluble materials. Typical heating conditions are from about 55°–65° C. for 5–20 minutes. Preferred is a heating step of 60° C. for 10 minutes.

The heated extract is centrifuged to remove debris, and the supernatant is applied to DEAE ion-exchange chromatography medium in two steps as described above. Preferred adsorption and elution conditions are described in the Examples. Any of a variety of DEAE ion exchange column chromatography media can be used in these steps, and the choice of media is not to be construed as limiting. Commercial sources include Pharmacia Fine Chemicals, BioRad, and Sigma.

Thereafter, endotoxin is removed to produce a protein having acceptable levels of endotoxin as recited earlier. The endotoxin removal step can be carried out in any of a variety of means, as are well known, and typically involve contacting the protein in solution with a chromatography medium capable of adsorbing endotoxin, and yielding a chromatography medium eluant which contains endotoxin-free protein. Where polymyxin is used, however, a non-ionic detergent such as Triton-X-100 is used to desorb the endotoxin off of the protein so that it can more efficiently be removed by the polymyxin. Commercial reagents for use in removing endotoxin may also be used, such as Acticlean described herein.

D. Chemically Modified Methioninase

Methioninase may be conjugated to a polymer with the purpose of extending its half-life and decreasing its immunogenicity or antigenicity.

There is the possibility of an allergic response in oversensitive individuals. On the other hand, anti-methioninase antibodies may shorten the half-life of methioninase.

Various approaches have been taken in attempts to solve the problem of antigenicity of polypeptides and proteins. Coupling of polymers such as polyethylene glycol to proteins is one of the approaches to reducing protein antigenicity. The present invention relates to chemical modification of methioninase produced by a novel and effective method in which purified methioninase is coupled with polyethylene glycol (PEG) under conditions which maintain the activity of the enzyme. The PEG-methioninase of this invention has an extended half life and no apparent immunogenicity.

The novel methioninase conjugated to polyethylene glycol ("PEG-methioninase" or "PEGylated methioninase") exhibits a high methionine depletion activity, an extended half-life, and low immunogenicity. Thus PEG-methioninase provides a novel means of inhibiting tumor growth while maintaining stability, increasing its serum half-life, decreasing immunogenicity and decreasing toxicity.

The present invention of PEG-methioninase which is stable, effective in methionine depletion with a long half-life and is non-immunogenic, may be utilized as a safe and effective anti-tumor agent for multiple dosing. PEG-methioninase may be stored in a liquid formulation of 0.12M sodium chloride in 10 mM sodium phosphate (pH 7.2) at −70° C., 4° C. and at room temperature without loss of activity.

Importantly, the PEG-methioninase of this invention is non-immunogenic which renders it particularly desirable for the treatment of cancer patients who are sensitive to methioninase, and require repeated dosing. Those of ordinary skill in the art will recognize that as with methioninase, the PEG-methioninase may be provided in a variety of formulations.

A preferred formulation of the purified endotoxin-free methioninase is in 0.12M sodium chloride in 10 mM sodium phosphate buffer (pH 7.2) at a concentration between 0.06M and 0.2M. The activity is approximately 10 units/mg.

The PEGylated methioninase may be tested by means well known to those of ordinary skill in the art. For example, in vivo testing may be used to determine the pharmacology, safety and functional characteristics of PEG-methioninase produced by the method of the invention.

Such tests may include determination of acute toxicity, pharmacokinetics of PEG-methioninase, depletion of methionine in serum and evaluation of immunogenicity of PEG-methioninase.

Purified endotoxin-free PEG-methioninase is injected into the tail-vein of mice and the blood samples are collected every two hours. The levels of methioninase are measured by the activity assay. The levels of methionine are measured with HPLC after methionine derivitization.

Acute toxicity studies may be performed in any suitable experimental animals. In mice, 10–100 units/1–10 mg of PEG-methioninase are injected into the tail-vein. Vital signs and visual observations are recorded. The blood samples are collected before the injection and every two hours after injection. Both the activity of methioninase and the levels of methionine are measured. The functions of both kidney and liver function are also measured. The presence or absence of toxic effects on tissues such as lung, kidney, liver and brain are determined by standard techniques. The blood and bone marrow are analyzed as well.

In another embodiment, the methioninase is conjugated to a polymer resulting in a substantially nonimmunogenic composition and also resulting in an increase in the half-life of methioninase activity in vivo.

In one embodiment the methioninase is chemically modified by conjugation to a polymer.

In another embodiment the methioninase is chemically modified by conjugation to a polyalkylene oxide. Examples of polyalkylene oxides include, but are not limited to, polyethylene oxide, polypropylene oxide, copolymers of ethylene oxide, and copolymers of propylene oxide.

In a preferred embodiment the methioninase is chemically modified by conjugation to polyethylene gylcol.

In another preferred embodiment the methioninase conjugated to polyethylene glycol is substantially free of endotoxin.

The invention also provides a pharmaceutical composition comprising a therapeutically effective amount of methioninase conjugated to a polymer. The polymer may be a polyalkylene oxide, for example, but not limited to, polyethylene oxide, polypropylene oxide, copolymers of ethylene oxide, and copolymers of propylene oxide.

In a preferred embodiment is provided a pharmaceutical composition comprising a therapeutically effective amount of methioninase conjugated to polyethylene glycol. In another preferred embodiment the pharmaceutical composition comprises a therapeutically effective amount of methioninase that is substantially free of endotoxin and is conjugated to polyethylene glycol.

Also provided is a method for producing endotoxin free methioninase which is conjugated to a polymer by coupling endotoxin-free methioninase which is conjugated to a polymer by coupling endotoxin-free methioninase with a polymer to form a substantially nonimmunogenic chemically modified endotoxin free methioninase.

In a preferred embodiment the method includes coupling the methioninase to polyethylene glycol.

In a further preferred embodiment the coupling is performed by reacting endotoxin-free methioninase with methoxy polyethylene glycol succinimidyl carbonate.

Also provided is a method of treating a patient having a tumor comprising administering a therapeutically effective amount of methioninase.

In a preferred embodiment the methioninase is substantially free of endotoxin.

In a further preferred embodiment the methioninase is conjugated to a polymer.

In a further embodiment the poly is a polyalkylene oxide.

In a further preferred embodiment the methioninase is conjugated to polyethylene glycol.

E. DNA Segments and Vectors

I. Methioninase-Coding DNA Molecules

Methioninase can also be produced by recombinant DNA (rDNA) techniques, as the gene encoding the enzyme can be cloned from the genomic DNA or CDNA of *Pseudomonas putida* bacterial source described earlier as a source for purifying methioninase. Thus, the present invention also contemplates a DNA segment consisting essentially of a sequence of nucleotide base sequence encoding methioninase.

The isolated gene can be operably linked to an expression system to form an rDNA capable of expressing, in a compatible host, methioninase.

Of course, modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

The DNA segments of the present invention are characterized as including a DNA sequence that encodes a methioninase. That is, the DNA segments of the present invention are characterized by the presence of a methioninase structural gene. Preferably the gene is present as an uninterrupted linear series of codons where each codon codes for an amino acid residue found in the methioninase protein, i.e., a gene free of introns.

Homologous DNA and RNA sequences that encode the above methioninase are also contemplated.

DNA segments (i.e., synthetic oligonucleotides) that are used as probes or specific primers for the polymerase chain reaction (PCR), and to synthesis gene sequences encoding methioninase can easily be synthesized by chemical techniques, for example, the phosphotriester method of Matteucci, et al., (*J. Am. Chem. Soc.* 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

In addition, the invention contemplates a recombinant DNA molecule (rDNA) containing a DNA segment of this invention. A rDNA can be produced by operatively linking a vector to a DNA segment of the present invention.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the methioninase structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the methioninase gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Anyl. Genet.* 1:327–341, 1982. Alternatively, the selectable marker can be present on a separate plasmid, and the two vectors are introduced by co-transfection of the host cell, and selected by culturing in the appropriate drug for the selectable marker.

The invention also contemplates a host cell transformed with a recombinant DNA molecule of the present invention. The host cell can be either procaryotic or eucaryotic, although eucaryotic cells are preferred. Eucaryotic cells useful for expression of a methioninase protein are not limited, so long as the cell line is compatible with cell culture methods and compatible with the propagation of the expression vector and expression of the methioninase gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the CHO-K1 cell line described herein.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA* 69:2110, 1972; and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al., *Virol.* 52:456, 1973; Wigler et al., *Proc. Natl. Acad. Sci. USA* 76:1373–76, 1979, and the teachings herein.

Successfully transformed cells, i.e., cells that contain a rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.*, 98:503, 1975, or Berent et al., *Biotech.* 3:208, 1985.

Nutrient media useful for culturing transformed host cells are well known in the art and can be obtained from several commercial sources. In embodiments wherein the host cell is mammalian, a "serum-free" medium can be used. Preferred is the culturing conditions described herein.

II. Cloning a Methioninase-Coding DNA Molecule

Polyclonal antiserum from rabbits immunized with the purified methioninase as described in the Examples can be used to probe a *Pseudomonas putida* partial genomic expression library such as lambda gt11 to obtain the appropriate coding sequence for methioninase. The cloned CDNA sequence can be expressed as a fusion protein, expressed directly using its own control sequences, or expressed by constructions using control sequences appropriate to the particular host used for expression of the enzyme.

Thus, the complete coding sequence for methioninase can be obtained from which expression vectors applicable to a variety of host systems can be constructed and the coding sequence expressed.

Alternatively in one embodiment, portions of the DNA encoding at least six contiguous amino acids can be synthesized and used as probes to retrieve DNA encoding methioninase from the nucleic acids of *Pseudomonas putida*. Oligomers containing approximately 18–20 nucleotides (encoding about a 6–7 amino acid stretch) are prepared and used against genomic DNA libraries to obtain hybridization under conditions of sufficient stringency to eliminate false positives. The sequences encoding six amino acids would supply information sufficient for such probes.

The partial amino acid residue sequence of methioninase purified from *Pseudomonas putida* was determined for three peptide fragments of methioninase by amino acid microsequencing, and are as follows:

(1) Amino terminus of Methioninase:

NH2-Met-His-Gly-Ser-Asn-Lys-Leu-Pro-Gly-Phe-Ala-Thr-Arg-
Ala-Ile-His-His-Gly-Tyr-Asp- (SEQ ID NO 1)

(2) CBR1 fragment:

-Gly-Ala-Ile-Thr-Ser-Thr-Leu-Trp-Thr-Leu-Leu-Arg-Pro-Gly -Asp-
Glu-Val-Leu-Leu-Gly-Asn-Thr-Leu-Tyr-Gly-Cys-Thr-Phe -Ala-
Phe-Leu-His-His-Gly-Ile-Gly-Glu-Phe-Gly-Val-Lys-Leu -Arg-
His-Val-Asp-. (SEQ ID NO 2)

(3) CBP fragment:

-Ala-Asp-Ile-Ala-Gly-Val-Ala-Lys-Ile-Ala-Arg-Lys-His-Gly -Ala-
Thr-Val-Val-Val-Asp-Asn-Thr-Tyr-Gln-Thr-Pro-Tyr-Leu -Gln-
Arg-Pro-Leu-Glu-Leu-Gly-Ala-Asp-Leu-Val-Val-Xaa-Ser -Ala-
Thr-Lys-Tyr- (SEQ ID NO 3).

From the above sequences, stretches of at least six amino acid residues are available for preparing a probe for use to isolate genomic DNA that encodes methioninase using standard methods.

Alternatively, one can prepare oligonucleotide primers in pairs for use in a polymerase chain reaction (PCR), as is well known, to selectively clone a methioninase gene specific-probe from methionine-expressing cells. A preferred cell for cloning with PCR primers is *Pseudomonas putida*, and preferred PCR primer pairs based on the above-identified amino acid residue sequences (SEQ ID NOs 1–3) are (1) 5'-GCNATHCAYCAYGGNTA-3' (SEQ ID NO 4), (sense)

(2) 5'-TTNACNCCRAAYTCNCC-3' (SEQ ID NO 5), (antisense) and (3) 5'-TAYGGNTGYACNTTYGC-3' (SEQ ID NO 6), (sense)

(4) 5'-GTYTGRTANGTRTTRTC-3' (SEQ ID NO 7) (antisense).

In the oligonucleotides, A, T, G, and C designate the normal four nucleotide bases of DNA, N designates all four bases, Y designates C and T, and R designates A and G.

A preferred PCR denature/anneal/extend cycle for using the above PCR primers is as follows: denature the template DNA at 100 degrees Centigrade (100 C.) for 5 min, then conduct Step A: maintain at 94 C. for 5 min; then conduct Step B: cycle 30 times from 94 C., 1 min (denature), to 48 C. for 1.5 min (anneal), to 70 C. for 1.5 min (extend); then conduct Step C: maintain at 70 C. for 10 min; then repeat steps A, B and C to amplify a methioninase gene-specific probe. The resulting probes are used to probe genomic libraries for the cloning of a recombinant methioninase DNA sequences.

In general terms, the production of a recombinant form of methioninase typically involves the following:

First, a DNA is obtained that encodes the mature enzyme. If the sequence is uninterrupted by introns, as expected from a bacterial source, it is suitable for expression in any host. This sequence should be in an excisable and recoverable form.

The excised or recovered coding sequence is then preferably placed in operable linkage with suitable control sequences in a replicable expression vector. The vector is used to transform a suitable host and the transformed host cultured under favorable conditions to effect the production of the recombinant methioninase. Optionally the methioninase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene and were discussed in detail earlier.

The strategy for isolating DNA encoding the desired methioninase encoding DNA, using the bacteriophage vector lambda gt11, is as follows. A library can be constructed of EcoRI-flanked AluI fragments, generated by complete digestion of *Pseudomonas putida* DNA, inserted at the EcoRI site in the lambda gt11 phage (Young and Davis, *Proc. Natl. Acad. Sci. (USA)* 80:1194–1198, 1983). Because the unique EcoRI site in this bacteriophage is located in the carboxyl-terminus of the B-galactosidase gene, inserted DNA (in the appropriate frame and orientation) is expressed as protein fused with B-galactosidase under the control of the lactose operon prompter/operator.

Genomic expression libraries are then screened using the antibody plaque hybridization procedure. A modification of this procedure, referred to as "epitope selection," uses antiserum against the fusion protein sequence encoded by the phage, to confirm the identification of hybridized plaques. Thus, this library of recombinant phages could be screened with antibodies that recognize the methioninase protein in order to identify phage that carry DNA segments encoding the antigenic determinants of the methioninase protein.

Approximately $2 \times 10^5$ recombinant phage are screened using rabbit anti-methioninase antiserum. In this primary screen, positive signals are detected and one or more of these plaques are purified from candidate plaques which failed to react with preimmune serum and reacted with immune serum and analyzed in some detail. Anti-methioninase antibodies can be prepared by a number of known methods, see, for example, U.S. Pat. Nos. 4,082,735, 4,082,736, and 4,493,795.

To examine the fusion proteins produced by the recombinant phage, lysogens of the phage in the host Y1089 are produced. Upon induction of the lysogens and gel electrophoresis of the resulting proteins, each lysogen may be observed to produce a new protein, not found in the other lysogens, or duplicate sequences may result. Phage containing positive signals are picked. Typically, one positive plaque is picked for further identification and replated at lower densities to purify recombinants and the purified clones are analyzed by size class via digestion with EcoRI restriction enzyme. Probes can then be made of the isolated DNA insert sequences and labeled appropriately and these probes can be used in conventional colony or plaque hybridization assays described in Maniatis et al., *Molecular Cloning: A Laboratory Manual*, (1982), the disclosure of which is incorporated herein by reference.

Insofar as a rDNA molecule can be used to express methioninase, one embodiment contemplates a DNA molecule capable of expressing methioninase, and therefore that encodes methioninase.

In another embodiment, insofar as a rDNA molecule is used to express methioninase under controlled circumstances, such as in a transfected cell, a rDNAS is contemplated that contains a first nucleotide sequence that encodes methioninase and is capable of expressing the methioninase, which first sequence is operatively linked to a second nucleotide sequence defining means for regulating the expression of the first sequence.

Means for regulation of a gene include inducible promoters, and other regulatory elements. Preferably, the inducible promoter is easily controlled, such as being responsive to a nutrient in the medium. A preferred responsive element is the metallothionine promoter.

In another embodiment, it is considered useful if the methioninase encoding gene can be irreversibly inactivated or removed from the tissue to be treated. Thus the invention contemplates a further (third) element which defines a means for inactivating the expression of the first sequence. An example is a suicide gene or other genetic marker that allows the selection of cells lacking the inactivating gene.

Other genetic configurations will be apparent to one skilled in the art.

F. Native-State Histoculturing Method for Determining Tumor Cell Responsiveness to Methioninase and Other Methionine Depletion Reagents In one embodiment, the invention contemplates a screening procedure for determining the effectiveness of a methioninase tumor treatment method of the present invention, providing the ability to test various anti-mitotic agents, drug dosages and administration variables for optimum effectiveness when treating a particular tumor. Briefly, the invention involves culturing an explant of the tumor to be treated in histoculture, as described herein, and exposing the cultured sample to various treatment regimens to identify the most effective treatment for inhibiting or killing the tumor.

Histoculturing involves the culturing of a explanted (i.e., surgically excised) tissue sample on a support matrix such that the native three dimensional architecture of the explanted tissue remains relatively intact. The cells in the explanted (histocultured) tissue sample are not disaggregated from their native tissue arrangement, thus the original architecture is preserved, rendering the sample to a more representative environment for assay. Histoculture methods have been described by Vescio et al., *Proc. Natl. Acad. Sci. USA* 84:5029–5033, 1987; and Hoffman et al., *Proc. Natl. Acad. Sci. USA* 86:2013–2017, 1989.

Typically, the tissue whose drug responsiveness characteristics are to be determined is explanted by an aseptic surgical procedure and a portion thereof is divided into sections having a volume of about 0.5 to about 10, preferably a volume of about 1.0 to about 8.0, more preferably 1.0 to 2.0 cubic millimeters.

When tumors are being assayed, it is important to examine multiple portions of the tumor in separate assays because tumors are very heterogeneous.

After cubing, the explanted tissue is divided into aliquots, typically at least about six, one of which is typically designated a control that receives no exposure or contact(s) with the compounds being examined. The aliquots are then histocultured on a support matrix so that the three-dimensional integrity of the tissue is maintained.

A support matrix of this invention provides a trabecular structure with interstices suited for capillary action to deliver aqueous nutrients from the medium to the base of the internal surface of the histocultured sample. Thus, any support having this capacity is contemplated including synthetic meshes such as nylon, borosilicate glass fiber, or polypropylene or organic meshes such as cellulose or collagen. Preferably, the support matrix is a hydrated extracellular support matrix.

As used herein, the phrase "extracellular support matrix" means a semi-solid, such as a gel or sponge, comprising one or more organic molecules or molecular aggregates, which molecules or aggregates are those produced and secreted by cells into the extracellular space and which serve, in vivo, as a support, adhesive and framework for maintaining three-dimensional tissue organization and function. Exemplary of such molecules are high-molecular weight proteins and glycoproteins such as collagen, laminin, fibronectin and the like, complex polysaccharides and the like molecules.

In a preferred embodiment, the extracellular support matrix is a collagen-containing gel. Exemplary collagen-containing gels are gelatinized pig skin such as GEL-FOAM™ (The Upjohn Company, Kalamazoo, Mich.) and a composition comprising laminin, collagen, proteoglycan and entactin such as MATRIGEL™ (Collaborative Research, Inc., Bedford, Mass.). GELFOAM™ is a patented product described in U.S. Pat. No. 2,465,357, and described in U.S. Pat. No. 4,060,081 to Yannas et al., the disclosures of which are incorporated herein by reference.

In another preferred embodiment, the extracellular support matrix is a homopolysaccharide sponge. Leighton, J., *J. Nat'l. Cancer Instit.* 12:545–561, 1951. A preferred homopolysaccharide is cellulose. Homopolysaccharide sponges contemplated by the present invention are not limited as to weave or net size.

In still another preferred embodiment, the extracellular support matrix comprises a combination of a collagen-containing gel and a homopolysaccharide sponge. Preferably, such a combination comprises a top layer of a collagen-containing gel and a bottom layer of a homopolysaccharide sponge. The collagen-containing gel is preferably gelatinized pig skin and the homopolysaccharide is preferably cellulose. In a particularly preferred embodiment, the support matrix comprises a combination of a top layer of GELFOAM™ and a bottom layer of a cellulose sponge.

Various liquid tissue culture nutrient media capable of supporting tissue cell growth are known in the art. The medium used can either be serum-containing or serum-free with additives such as insulin, transferrin, selenium, estradiol and the like. A culture medium found to be particularly suitable in the present invention in Eagle's minimal essential medium (MEM) Eagle, *Science*, 122:501 (1955) and Eagle, *Science* 130:432, 1959).

The tissues are typically histocultured in a humidified atmosphere at a temperature corresponding to that of the body temperature of the animal from which the tissue sample came, e.g. 37° C. for human tissue samples.

The histoculture method involves exposing (contacting) the non-disaggregated tissue sample under histoculturing conditions with a predetermined amount (determinate concentration) of a methionine-depleting medium for a predetermined period of time (determinate time period) and thereafter determining the effectiveness in inducing cell stasis.

Thus, the invention contemplates a histoculturing method for determining solid tumor cell responsiveness to methionine depletion therapy comprising:

(a) histoculturing a non-disaggregated solid tumor sample comprising organized tumor cells;

(b) contacting said solid tumor sample under histo- culturing conditions with a preselected amount of a methionine-depleting medium for a time period sufficient to induce cell cycle stasis in cells of said sample, and form static tumor cells;

(c) determining the effect of said contacting upon said tumor cells, thereby determining said solid tumor cell responsiveness.

Preferably, the determining of step (c) comprises determining the extent of cell stasis in said solid tumor sample by evaluating the tissue architecture as described earlier.

A methionine-depleting medium, as used herein, is any of a number of culture media which, upon histoculture, reduce methionine concentrations. As described herein, a number of approaches to methionine depletion are contemplated herein, and can be used in the present histoculture methods. In fact, insofar as optimization of therapeutic treatment methods is the objective, it is preferable to test the effectiveness of several methionine-depleting media. These media can be methionine free, can be methionine free and supplemented with homocysteine, can be methionine free and contain methioninase, or can be methionine free and contain both homocysteine and methioninase according to the present invention.

In preferred embodiments, the histoculture method can further include screening for the histocultured sample's responsiveness to the anti-mitotic or other cell-cycle agent according to the present invention.

Thus, a preferred method is contemplated in which step (b) above further comprises the steps of:

(i) contacting the static tumor cells under histoculturing conditions with a cell cycle-inducing amount of methionine to initiate mitosis of the static tumor cells forming mitotic cells, and (ii) contacting the mitotic cells under histoculturing conditions with an anti-mitotic or other cell-cycle agent in an amount sufficient to inhibit mitosis of the mitotic cells.

The amounts of reagent in the contacting steps using either the methionine or the anti-mitotic agent, and the time periods for the contacting, can readily be varied to determine the optimum conditions for responsiveness to the treatment regimen. Thus, the optimum drug exposure dose level can be determined for the particular tumor tissue being tested for responsiveness.

The phrase "drug exposure dose level", as used herein, refers to the quantitative product of the drug concentration (e.g. in µl) and the time of the exposure period (e.g., in hours or minutes). The drug concentrations and exposure times are typically calculated from pharmacological data to simulate in vitro the drug exposure dose level achieved in vivo. Typically, it has been found that the drug exposure dose level required in carrying out the drug sensitivity measurements in accordance with the assay of the present invention.

The drug sensitivity measurements as described above can be carried out in a manner which enables the determination, for any given drug, of a "drug sensitivity index", which is indicative of the antineoplastic activity of the given drug against the specific human tumor from which the explanted cells were obtained. This procedure involves carrying out the drug sensitivity measurements of a plurality of dose levels extending over a multi-log range, and then using the results of these measurements to plot a curve of percent survival (the percentage of the assay count resulting from drug exposure versus the assay count of the control in the absence of drug exposure) versus drug exposure dose level. The "drug sensitivity index" of the given drug is then quantitated by measuring the area under such curve out to a defined upper limit which is correlated to the clinically achievable peak drug exposure dose level for that drug.

The sensitivity index obtained in the above-described manner is highly indicative of the antineoplastic activity of the drug against the specific tumor from which the explanted cells were obtained, with a low sensitivity index indicating high antineoplastic activity.

After histoculturing the cells in the presence of the agent being examined the samples are treated (cultured in the presence of) with a reagent that renders the cells of the histocultured sample suitable for determining the extent of drug responsiveness of the cells of the histoculture. Drug responsiveness can be assessed by determining the number, distribution and extent of viable cells or dead cells in the histocultured sample. In the case of determining drug responsiveness producing arrest of cells in a late phase of the cell cycle, a variety of methods can be used, most notably the measure of DNA content among populations of cells as described in detail in the Examples.

In addition, viability is assessed by measuring the incorporation into cells of the sample of an indicator specific for viable cells. As used herein, the phrase "specific for viable cells" means that the indicator is taken up or incorporated into living, but not dead, cells.

The indicator specific for viable cells may be a metabolic precursor or a non-metabolite that gains access to living cells. Exemplary metabolic precursors are ribo- or deoxyribonucleic acid precursors such as purines, pyrimidines, nucleosides and nucleotides. Preferably, the metabolic precursor is operatively linked to an indicating means to facilitate detection. A preferred indicating means for a metabolic-precursor indicator is a radiolabel such as $^{35}S$, $^{32}P$, $^{125}I$, $^{3}H$ and the like. A particularly preferred radiolabeled metabolic-precursor indicator is $^{3}H$-thymidine.

A preferred non-metabolite indicator specific for viable cells is a dye that is capable of optical detection. Any dye recognized in the art as being specific for viable cells can be used in this invention. See, e.g., Handbook of Fluorescent Probes and Research Chemicals, ed. by R. P. Haugland, Molecular Probes, publisher, Eugene, Oreg. (1989–1991).

In a preferred embodiment, the dye is a fluorescent dye. Exemplary viable-cell-specific fluorescent dyes are BCECF-AM (B-1150), Calcein-AM (C-1430), CFDA (carboxyfluorescein diacetate; C-195) Acridine orange (A-1301), Calcein blue (H-1426), Fura-2AM (F-1201), Fluorescein diacetate (F-1303) or Carboxy analog (C-1431) and the like. Such dyes are well known in the art and are commercially available (Molecular Probes, Eugene Oreg.). Particularly preferred are the dyes BCECF-AM or Calcein-AM. The numerals in the parenthesis indicates the product number for the listed fluorescent dyes that are available from Molecular Probes.

In one embodiment, the incorporation or uptake of fluorescent dyes specific for viable cells depends upon metabolic activity of the viable cell. In accordance with this embodiment, non-fluorescing dyes are taken up by viable cells and converted to a fluorescing product by an intracellular enzyme such as an esterase. The presence of intracellular fluorescence indicates viability.

In another embodiment, viability is assessed by measuring the uptake or incorporation into cells of the sample of an indicator specific for dead cells. As used herein, the phrase "specific for dead cells" means that the indicator is taken up or incorporated only into dead, non-viable cells.

Typically, dyes specific for dead cells are compounds with a high ionic charge and low permeability such that the dyes cannot permeate intact cellular membranes. When cells die, the membrane is structurally or functionally ruptured such that dyes specific for dead cells gain access to the intracellular space where they bind to intracellular components such as nuclear membranes.

A preferred dead-cell-specific indicator is a dye capable of optical detection. A preferred dead-cell-specific dye is a fluorescent dye such as propidium iodide, ethidium bromide, ethidium homodimer [(5,5'-diazadecamethylene)bis(3,8-diamino-6-phenylphenanthridium)dichloride, dihydrochloride] and the like. Most preferred is propidium iodide. Propidium iodide (PI) and other dyes specific for dead cells are well known in the art and commercially available (Molecular Probes, Eugene, Oreg.).

In still another preferred embodiment, assessing viability is accomplished by simultaneously measuring the uptake or incorporation of both an indicator specific for viable cells and an indicator specific for dead cells. Viability is assessed as the ratio of viable to dead cells. Where both the indicator specific for viable cells and the indicator specific for dead cells are fluorescent dyes, such dyes should have different emission spectra so as to facilitate discrimination between viable and dead cells. Compositions and methods for determining cell viability by the differential uptake of indicators specific for viable and dead cells and tissue culture samples are well known in the art. Haughland, Supra.

In a preferred-embodiment, the drug responsiveness assay further comprises assessing the viability of the sample prior to contacting the sample with the treatment regimen and comparing the assessed viability before and after treatment and thereby determining the responsiveness of the tissue sample to the treatment regimen.

Means for detecting the uptake or incorporation of indicators specific for viable cells are dependent upon the particular indicator used and are well known to those of skill in the art. A preferred means for detecting radiolabeled metabolic-precursors is autoradiography of histological sections of the samples that have taken up the precursor.

A preferred means for detecting dyes is microscopic examination. Microscopic examination can involve the use of any microscope that allows one to selectively and reproducible evaluate indicator incorporation into specific cells of the sample at varying locations within the three-dimensional, native-state histoculture.

Typically, the microscopic examination requires the capability of optical sectioning. Optical sectioning is the ability to view preselected depths within the three-dimensional structure of the sample in the absence of optical interference provided by the presence in the sample of microsomes, air bubbles, fat globules and other tissue components, which provide reflection of light and optical interference.

In addition, optical sectioning allows for viewing a variety of planes within the three dimensional tissue histoculture. By sequentially sectioning serial layers of the sample, one can produce a total picture of the tissue or, alternatively, a picture of a region of the sample where a particular cell type of interest is located. Thus, comparative studies of a plurality of depths or regions of the tissue sample can be made. In this way, viability and drug responsiveness can be assessed differentially in surface cells, at cells underneath the surface, and in cells buried deeper inside the tissue sample.

The optical section thickness can be varied to accommodate the cell size or tissue to be observed and can range from about 0.1 to 1000 microns. Preferred sections are in the range of 0.5 to 10 microns, preferably about 2 to 6 microns.

A preferred microscope that is capable of performing optical sectioning is a confocal scanning laser microscope such as the MRC-600 CONFOCAL IMAGING SYSTEM (Bio-Rad, Richmond, Calif.), mounted on a Nikon Optiphot using a 10× PlanApo plan objective. Other available methods for optically scanning or sectioning planes of the tissue sample are also contemplated by the present invention.

Viability is assessed at any particular location within the sample as a ratio of viable or dead cells to total cells or as a ratio of live to dead cells on the basis of the uptake of indicators specific for viable and dead cells respectively. When viability is assessed both before and after the treatment regiment, comparing the ratio of live to dead cells as assessed before and after treatment provides an indication of the effectiveness of the treatment regimen.

The procedure for applying indicators to the histocultured sample varies with the particular indicator used. Typically, indicators are added to the histoculture medium from about 1 to 24 hours after the treatment regimen. Following addition of the indicator to the medium, the culture is maintained under culturing conditions for a period of time sufficient to allow the indicator to enter and label the cells of the tissue sample. Preferably, the culture is maintained in the presence of the indicator for about 5 minutes to about 2 hours and, more preferably for about 10 to 20 minutes.

The concentration of indicator added to the medium varies with the particular indicator used. Where the fluorescent dyes PI and BCECF-AM are used, the dye concentration is from about 1 to about 100 micromolar, preferably from about 2 to about 50 micromolar, and more preferably about 5 micromolar each.

The use of the present histoculture method of the present invention has utility for the in vitro prediction of clinical responsiveness of a tumor to cancer chemotherapy according to the present methods, as well as the screening of new anticancer drugs for clinical trial involving the use of methioninase. For example, in treating a specific patient for a specific tumor, the explanted cells obtained from a biopsy of such specific tumor can be assayed in accordance with the present technique, and drug sensitivity measurements can be carried out for a plurality of different antimitotic drugs which are potentially clinically effective for the chemotherapeutic treatment of the specific tumor. After determining the relative drug sensitivity indices for each of the various drugs tested, these sensitivity indices may be used for predictably selecting the most promising (effective) of the drugs to be used for the chemotherapeutic treatment.

G. Use of Methioninase for Prevention of Hyperhomocysteinemia-associated Cardiovascular Disease Another aspect of the invention is the use of methioninase for homocysteine depletion therapy.

Figure 14:
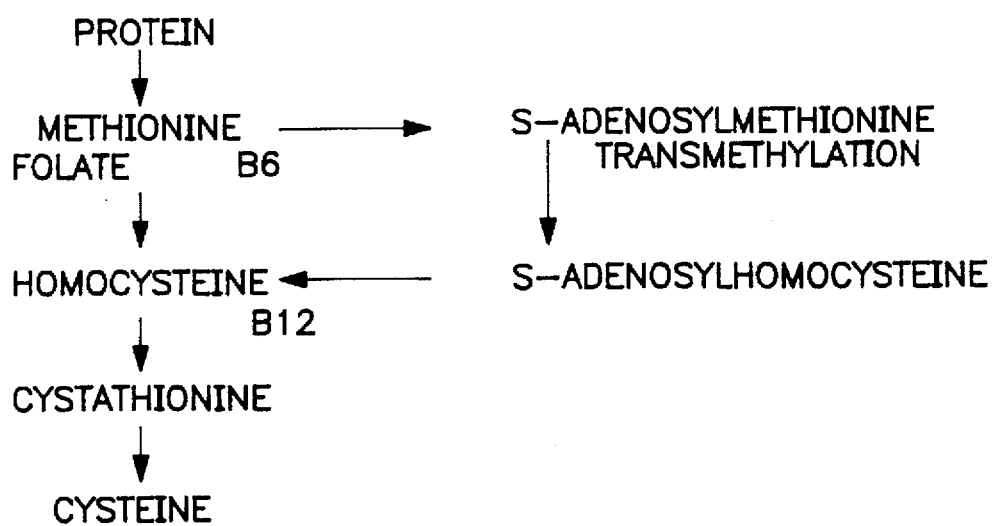
FIG. 14 is an illustration of the methioninase-homocysteine metabolic cycle.

Hyperhomocysteinemia has been associated with various types of cardiovascular diseases. The first association of these diseases with homocysteine was made by McCully in 1969. (McCully, K. S., Am. J. Pathol. 56: 111–28, 1969) McCully found a link between elevated plasma homocysteine concentrations and arteriosclerotic diseases. A recently concluded study of 1,041 people from the Framingham Heart Study found that elevated plasma levels of homocysteine leads to an increased risk of arteriosclerosis (Selhub, J. et al., *N. Engl. J. Med.* 32:286–91, 1995). Other studies have linked even moderate hyperhomocysteinemia to peripheral vascular, cerebrovascular and coronary heart disease. (Kang, S. et al., *Annu. Rev. Nutr.* 12:279–98, 1992). For example, fasting homocysteine concentrations in patients with vascular disease are 31% higher than in normal subjects. Plasma homocysteine concentrations 12% above the upper limit of normal were associated with the 3.4-fold increase in risk for myocardial infarction. (Stampfer, M. et al., *JAMA* 268:877–81, 1992). Studies of homocysteine metabolism have found that in 20 case control and cross-sectional studies of over 2000 subjects, show that patients with stroke and other cardiovascular blood diseases have higher blood levels of homocysteine than subjects with no cardiovascular diseases. This is in contrast with the fact that most patients with myocardial infarction have normal cholesterol levels. A striking result was found in the Physicians Health Study, where it was shown prospectively that where blood was drawn before cardiovascular disease was diagnosed 271 men who later had myocardial infarctions had significantly higher mean base line levels of homocysteine than matched controls who did not have myocardial infarctions (Ueland, P. et al., *Cardiovascular Disease Hemostasis and Endothelial Function*, New York: Marcel Dekler; 183–236, 1992). Although a variety of conditions can lead to elevated homocysteine levels, the relation between high levels of homocysteine and vascular disease is present regardless of the underlying metabolic cause. In a direct study, vascular lesions were induced in baboons and the baboons were infused with homocysteine for three months (Ueland, P., et al, supra). Hyperhomocysteinemia may be diagnosed by oral administration of methionine followed by the measurement of the levels of homocysteine in the patients. Abnormal homocysteine plasma concentrations after this oral methionine challenge is twelve times more present in patients with arteriosclerotic disease than in normal subjects (Ueland, et al., supra). Plasma homocysteine levels can be easily and rapidly measured by HPLC assays. Studies suggest that 40% of the population may have elevated homocysteine levels and be at risk for cardiovascular disease (Stampfer, M. and Malinow, M., *New Engl. J. Med.* 332:326–329 1995). Hyperhomocysteinemia can have acute effects in inducing arteriosclerotic disease and putting individuals at risk for myocardial infarction and cerebrovascular disease. Acute medical intervention is thus indicated for a large fraction of individuals at risk for cardiovascular disease. The methioninase of the present invention may be used as the therapy of choice for acute intervention to immediately lower homocysteine levels in individuals at risk. Methioninase catalizes two reactions, the cleavage of both the nitrogen-carbon bond and gamma-carbon-sulfar bond not only in methionine but also in homocysteine (Hoffman, *Bioch. et Biophys. Acta, Reviews on Cancer*, 738:49–87, 1984). Methioninase has significant activity for homocysteine as shown in Table 19, and observed in Soda, *Analyt. Biochem.* 25:228–235, 1968). FIG. 14 illustrates the metabolic cycle of homocysteine and methionine metabolism. The vitamins B-12, B-6, and folate influence the "left" side of the cycle illustrated in the figure and will be helpful in the maintenance of normal homocysteine levels in some individuals after methioninase treatments. However, the "right" side of the cycle is independent of the levels of these vitamins. In the right side of the cycle the presence of methionine can lead to excess homocysteine levels via elevated transmethylation reactions which may lead to cancer as well as to arteriosclerotic disease. For individuals with abnormalities in the right side of the cycle, maintenance as well as acute use of methioninase may be necessary to maintain normal levels of homocysteine. For cardiovascular disease, the substrate specificity of methioninase for both methionine and homocysteine is critical: methioninase will lower both the methionine level which is a precursor of homocysteine and will also lower the homocysteine level directly. Previous work in the area has only suggested the use of vitamins B-12, B-6 and folate as therapy to lower hyperhomocysteinemia. As shown in FIG. 14, merely providing these vitamins will not rectify any abnormalities in the right side of the cycle and may not decrease homocysteine in individuals with abnormalities in the right side of the cycle. The present invention includes a method of treating patients having such cardiovascular diseases with methioninase.

In one aspect, a method is provided of treating a patient having a cardiovascular disease comprising administering to the patient a therapeutically effective amount of methioninase.

A therapeutically effective amount of methioninase for homocysteine depletion is a predetermined amount calculated to achieve the desired level of homocysteine depletion so as to, for example, reduce the risk of arteriosclerosis.

Thus, the dosage ranges for the administration of methioninase of the invention are those large enough to produce the desired effect in which, for example, the risk of, or level of, arteriosclerosis, are reduced. The dosage should not be so large as to cause adverse side effects, such as hyperviscosity, syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of a methioninase of this invention is typically an amount such that when administered in a physiologically tolerable composition is sufficient to achieve a intravascular (plasma) or local concentration of from about 0.001 to about 100 U per ml, preferably above about 0.1 U, and more preferably above 1 U methioninase per ml. Typical dosages can be administered based on body weight, and are in the range of about 5–1000 U/kilogram (kg)/day, preferably about 10–50 U/kg/day, and more preferably about 20–40 U/kg/day.

In preferred methods, a methioninase used is substantially free of endotoxin, as discussed further herein. Particularly preferred is the use of methioninase produced herein that is substantially free of endotoxin.

Methods of administration known to those of ordinary skill in the art may be employed, and are described herein.

In another aspect the patient is treated with a therapeutically effective amount of methioninase which is substantially free of endotoxin.

In another aspect of the invention a patient with a cardiovascular disease is treated by administration of a therapeutically effective amount of a methioninase which is substantially free of endotoxins and is conjugated to a polymer. In a preferred aspect, the polymer is polyethylene glycol. In another preferred aspect of the invention the cardiovascular disease is arteriosclerosis.

In another aspect of the invention methioninase is administered to patients with extracranial carotid artery stenosis, peripheral vascular, cerebrovascular, coronary heart disease, and occlusive vascular disease.

In another aspect of the invention is provided a method of treating a patient having hyperhomocysteinemia by administering to the patient a therapeutically effective amount of methioninase. The methioninase may be substantially free of endotoxins and the methioninase may be conjugated through a polymer such as polyethylene glycol.

The invention also provides a method of lowering homocysteine levels in a patient comprising the step of administering to the patient a therapeutically effective amount of methioninase wherein the methioninase is substantially free of endotoxins. In another aspect of the invention a method is provided of preventing cardiovascular disease in a patient comprising the step of administering to the patient a therapeutically effective amount of methioninase. In a preferred aspect the methioninase administered to the patient is substantially free of endotoxin. In another preferred aspect the methioninase is conjugated to a polymer. In yet another preferred aspect a method is provided at preventing cardiovascular disease in a patient comprising the step of administering to the patient a therapeutically effective amount of a methioninase that is substantially free of endotoxin wherein the methioninase is also conjugated to polyethylene glycol. Example 10, herein, provides one example of in vivo homocysteine depletion.

H. Use of Methioninase for Tumor Imaging

In another aspect of the invention a method is provided of diagnosing a tumor in a patient comprising the steps of depleting $^{12}$C methionine in a patient by administering methioninase to the patient followed by repleting the methionine in the patient by administering $^{11}$C methionine to the patient and finally detecting the presence of $^{11}$C methionine in the tumor cells of the patient. The $^{11}$C methylation may be detected by means of, for example, but not limited to, positron emission tomography (PET) scanning. Those of ordinary skill in the art are familiar with other methods of detecting $^{11}$C uptake by cancerous cells. Such methods are described in, for example, Lapela et al., *J. Nucl. Med.* 35:1618–23, 1994; Miyazawa et al., *J. Nucl. Med.* 34:1886–91, 1993; Leskinen-Kallio et al., *J. Nucl. Med.* 33:691–95, 1992; Shields et al., *J. Nucl. Med.* 33:581–84, 1992; Huovinen et al., *Brit J. Cancer* 67:787–91, 1993; Dethy et al., *J. Nucl. Med.* 35:1162–66, 1994; Lindholm et al., *J. Nucl. Med.* 34:1711–16, 1993; Leskinen-Kallio et al., *J. Nucl. Med.* 32:1211–18, 1991; and Mineura et al., *J. Nucl. Med.* 32:726–28, 1991, all hereby incorporated by reference herein.

In a preferred aspect of the invention, the methioninase provided is substantially free of endotoxin.

In another preferred aspect of the invention the methioninase was conjugated to a polymer.

In a most preferred aspect the polymer conjugated to the methioninase is polyethylene glycol.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Methionine Dependence of Human Tumors in Histoculture

Various human tumor tissue samples were explanted from human patients as described by Freeman et al., *Proc. Natl. Acad. Sci. USA* 83:2694–98, 1986; and by Vescio et al., *Proc. Natl. Acad. Sci. USA* 84:5029–33, 1987. (The teachings of all of the references cited herein are hereby incorporated by reference).

Briefly, after tissues were surgically removed, they were divided into 1- to 2-mm diameter pieces and placed on top of previously hydrated extracellular-matrix-containing flexible gels derived from pigskin (Gelfoam, Upjohn) to form a three-dimensional culture. Eagle's minimal essential medium (MEM) from GIBCO containing Earle's salts, glutamine, nonessential amino acids lacking methionine and choline chloride, and containing 200 uM homocysteine thiolactone, and the antibiotics garamycin and claforan. The medium was added to the cultures such that the upper part of the gel was not covered, and cultures were maintained at 37 degrees C. in a carbon dioxide incubator to allow the explanted tissue specimens to grow.

Under the methionine starvation conditions, the tumor cells are observed to become enlarged and stop dividing, indicative of cell stasis.

For detailed analysis of cell growth, and cell cycle stasis, histocultured tumor tissue was digested with collagenase to release single cells, and cell suspensions were treated for DNA staining with Feulgen and the DNA content of the cell nuclei were measured by computer assisted image analysis using a Cambridge Instruments Quantimet-520 system.

Methionine-dependent cell cycle block (MDCCB) occurs where cells replicate their DNA but do not complete mitosis and re-enter the $G_1$ phase of their cell cycle. MDCCB is measured by determining the DNA content of about five hundred cells from a sample, and calculating the ratio of cell numbers as follows: MDCCB=(cells in $G_1$/total cells in MET−culture)/(cells in $G_1$/total cells in MET+ culture). Dependence on methionine was scored where MDCCB was less than 0.65.

Eight of 25 human patient tumors were observed to be methionine dependent (mean value MDCCB=0.44) and were able to have their cells blocked in the cell cycle. These tumor types include colon, melanoma, ovarian, prostate, pancreatic and breast cancer. When a methionine-dependent tumor was shifted in histoculture to a methionine-containing diet, the normal cell cycle distribution resumed, indicating that the cell cycle block is reversible.

By the above criteria, human tumors shown to be methionine dependent in histoculture include tissue samples from pancreatic cancer, cecum cancer, melanoma, prostate cancer, and breast cancer. This list of methionine-dependent cancers is not to be considered as complete, but rather is indicative that all types of cancers which are methionine dependent. Other related or similar tumor tissue types are expected to also be methionine dependent, and such dependence can be readily determined by the above method.

For example, although not tested in histoculture, numerous tumor cell lines have been shown to exhibit methionine dependence in disaggregated cell (monolayer) cultures, as described by Mecham et al., *Biochem. Biophys. Res. Comm.* 117:432, 1983, and are all considered to be candidates for methionine dependent therapy as described herein. These tumor cell lines include lung carcinoma (A2182), primary transitional cell carcinoma of bladder (J82), prostate adenocarcinoma metastasis to bone marrow (PC3), adenocarcinoma of the lung (SK-LU), adenocarcinoma of breast-pleural effusion (MCF-7), carcinoma of kidney (A498), fibrosarcoma (8387 and HT-1080), osteogenic sarcoma (HOS), rhabdomyosarcoma (A673), and neuroblastomametastasis to bone marrow (SK-N-SH).

Of particular importance is the ability to demonstrate by the present method that a patient's tumor can be analyzed in histoculture for methionine dependence. Furthermore, a significant number of tumors tested exhibit methionine dependence, indicating that the assay is a valuable screen because it produces a positive result in a large number of patient tumors. Finally, the results show that the cells of the tumor can be "phased" or synchronized in their cycle such that the cells of the tumor can be induced to enter cell cycle stasis, and subsequently be returned at a preselected time to normal cell cycle by replenishing the supply of methionine. This ability to phase cells of a tumor is particularly important, particularly for use in methods using anti-mitotic and other cell-cycle-specific therapy, described further herein.

Furthermore, because normal cells are not methionine dependent, the ability to synchronize tumor cell growth is important because it is selective for tumor cells, thereby reducing the toxicity of subsequent anti-tumor chemotherapy based on cell synchronization of normal cells.

2. Homocysteine Selectively Rescues Normal Tissues From Methionine Depletion Therapy Homocysteine (Hcy) is a biochemical precursor to methionine, and is most often equivalently converted to methionine in both normal and tumor cells. However, tumor cells have a much greater requirement for methionine, possibly due to elevated transmethylation reactions. Thus, it is observed that normal cells are methionine starvation independent when cultured in the presence of homocysteine, whereas tumor cells are generally sensitive to methionine starvation even in the presence of homocysteine.

Normal human FS-3 foreskin cells were cultured in methionine-free medium described in Example 1 containing as a supplement methionine (250 uM) or homocysteine thiolactone (100 uM) for 21 days, and the cells were analyzed for DNA content to determine the effect of the culture conditions upon cell cycle arrest. When cell count was compared to DNA content, an increase of DNA content in a population of cells is indicative of arrest in the late-S/$G_2$ phase. Under these conditions, the FS-3 normal foreskin cells were not detectably affected by the homocysteine, indicating methionine independence when cultured in the presence of homocysteine.

In contrast, cell cycle arrest, as measured by an increase of DNA content, was observed when the following human patient tumors were cultured in the above homocysteine-supplemented methionine-free medium: prostate, pancreas, renal, breast, colon, melanoma and ovarian cancer.

Thus, methionine starvation can be used to effectively and specifically block the cell cycle of tumor cells. In particular, the data show that the combined use of methionine starvation together with homocysteine supplement preferentially stops cell cycling of tumor cells over normal cells. Thus, the present conditions allow for the selective cell arrest of tumor cells over normal cells.

3. Cell Synchronization Enhances Anti-Mitotic Drug Therapy

Synchronization of the cell cycle was produced by the arrest of cells using methionine starvation as described in Example 2, followed by initiation of the cell cycle by the addition of methionine to the culture. The result is to systematically first arrest the tumor cells late in the cell cycle prior to division, thereby synchronizing mitosis, and then synchronously initiating growth of the cells in the tissue. Furthermore, using the methods of Example 2 combining methionine depletion and homocysteine supplementation, together with the synchronized initiation of the cell cycle, one can selectively synchronize the tumor cells in a tissue.

The synchronization of tumor cells was evaluated for use in combination with anti-mitotic agents to determine the most effective anti-tumor therapy.

Human ovarian tumor tissue samples were explanted from a human patient, and cultured in histoculture as described in Example 1. Multiple ovarian tumor tissue histocultures were set up. One set of histocultures were maintained under histoculture conditions for 20 days in methionine deficient homocysteine medium (Met$^-$Hcy$^+$) as described in Example 2, and the other set of histocultures were maintained in methionine containing medium (Met$^+$Hcy$^-$) as described in Example 2 for 20 days. Thereafter, Met$^-$Hcy$^+$ treated cells were shifted to Met$^+$Hcy$^-$ medium, and both cultures were exposed to vincristine at 23 nanograms (ng) per milliliter (ml) for 5 days. The inhibition rate (IR) for the histocultured tissue sample was determined in both cases, and is expressed as the percent of inhibition of growth as measured by the change in incorporation of tritiated thymidine. Whereas the growth of the vincristine-treated histoculture maintained in methionine was inhibited by about 19 percent, the growth of the vincristine-treated histoculture maintained in methionine-free medium was inhibited by about 50 percent. Thus, methionine dependent tumor tissues respond significantly well to anti-mitotic agents when the tissue is first subjected to methionine starvation.

In a similar experiment, human cancer cells, sarcoma cells, were co-cultured with normal human fibroblasts in monolayer culture format using methionine deficient (Met$^-$Hcy$^+$) medium or using methionine containing medium (Met$^+$Hcy). Cells co-cultured with methionine exhibited tumor cell overgrowth, whereas cells co-cultured with Met$^-$Hcy$^+$ medium first for methionine depletion, and then shifted to Met$^+$Hcy$^-$ medium containing vincristine exhibited substantial cell killing such that all tumor cells were killed, and the normal cells grew into a healthy monolayer.

The results of this study are severalfold. First, vincristine alone was ineffective as an anti-tumor agent. Second, tumor cells are preferentially killed or inhibited by the use of methionine starvation to synchronously cycle the cells when combined with anti-mitotic agent treatment.

4. Purification of Methioninase

Methioninase was purified from *Pseudomonas putida* as follows. *Pseudomonas putida* cultures were obtained from the American Type Culture Collection (Rockville, Md.) as the strain designated ATCC 8209, and were cultured according to the ATCC instructions to form a pellet of bacterial cells (i.e., a cell paste). The growth medium consists per liter of methionine, 3.0 gm; urea, 1.0 gm; glycerol, 1.0 gm; $MgSO_4$—$7H_2O_1$ 0.1 gm; yeast extract, 0.25 gm; potassium phosphate buffer to a final concentration of 10 mM, pH 7.2. The bacteria were cultured for 2–3 days until an optical density of 0.8–1.0 at 540 nm was reached. The cells were then harvested by centrifugation of the culture medium at 6000 rpm for 20 min in a Sorval Model RC2-B centrifuge with a GSA rotor. The resulting pellet was washed with 5 volumes of normal saline and recentrifuged to form a cell paste.

The cell paste pellet of the bacteria culture was flooded with acetone with 10 volumes of acetone precooled to −20 C., suspended with occasional mixing for 10 minutes, and then filtered through Whatman Filter paper, Qualitative N1. The resulting precipitate was collected from the filter, resuspended in the same volume of acetone, refiltered as above, washed in ether, dried under vacuum to form an acetone powder. The acetone powder was stored at −20 C. for up to 4–5 months without loss of activity. Thereafter, all steps were conducted at 4° C. unless otherwise stated.

A. Extraction Method 1

The acetone powder was then extracted with 10 mM potassium phosphate, pH 7.2, containing 10 uM pyridoxal phosphate, 0.01% beta-mercaptoethanol, 1 mM EDTA and 0.01 uM PMSF. The resulting suspension was centrifuged at 20,000×g for 40 min to form a pellet, the supernatant collected and heated to 60° C. for 5 min, and the resulting precipitate was removed by centrifugation at 10,000×g for 5 min to form a supernate. The supernate was recovered and about 600 ml was applied to a DEAE Toyopearl (Japan) column (50×5 cm) equilibrated with 40 mM potassium chloride in 20 mM potassium phosphate buffer, pH 7.4, (loading buffer), followed by elution with a linear gradient of KCl at a concentration of from 40 to 200 mM in loading buffer. Elution fractions were collected, assayed for methioninase activity, and the active fractions were pooled.

Methioninase was assayed by following the conversion of methionine to alpha-ketobutyrate. To that end, varying amounts of enzyme were added to a 1 ml reaction volume having 50 mM phosphate buffer, pH 8.0, containing 10 uM pyridoxal phosphate and 10 mM methionine, and the reaction mixture was maintained at 37° C. for 10 minutes. Thereafter, the reaction was stopped by adding 0.5 ml of 4.5% TCA, the reaction admixture was centrifuged at 15,000×g for 3 minutes, and the resulting supernatant was collected and assayed for alpha-ketobutyrate as is well known, and described by Tanaka et al., *FEBS Letts.* 66:307–311, 1976. The amount of protein was also determined as described by Lowry et al., *J. Biol. Chem.* 193:265 (1951) for specific activity calculations, or was more roughly estimated measuring optical density at 280 nm.

The elution profile off of the DEAE-Toyopearl column showed a single sharp peak of methioninase activity eluting at between fractions 10 and 20.

The pool of methioninase-containing fractions was then adjusted to pH 8.3 and about 200 ml applied to a DEAE Sephadex-A50 column (40×3 cm) equilibrated with 20 mM potassium pyrophosphate buffer, pH 8.3, (Sephadex loading buffer) containing 120 mM potassium chloride, and eluted with a linear gradient of 120 mM KCl to 500 mM NaCl in Sephadex loading buffer. Elution fractions of 15 ml each were collected, assayed for methioninase activity, concentrated by ultrafiltration, dialyzed against 10 mM potassium phosphate buffer, pH 7.4, containing 140 mM KCl, to form purified methioninase, and stored at −15° C.

The elution profile off of the DEAE-Sephadex column showed a single sharp peak of methioninase activity eluting at between fractions 90 and 105.

The purified methioninase was analyzed on 7.5% PAGE nondenaturing gels, and shown to be a single homogeneous band of approximately 150,000 to 180,000 daltons. When analyzed on a 10% PAGE-SDS denaturing gel containing beta-mercaptoethanol, the purified protein contained two bands of approximately 40,000 and 43,000 daltons. The proteins on the PAGE gels were visualized by protein stain, and the observed single band on the nondenaturing gel was considered to be homogeneous because no other bands of significant intensity (i.e., less than 1% the intensity of the primary band) were detected on the gel. Protein concentration of the purified methioninase composition was determined using standard protein assays.

The purified methioninase was assayed for methioninase activity using the production of alphaketobutyrate as described earlier. Although production lots varied in specific activity, the above purification protocol typically yielded methioninase having from about 2 to 20 U/mg specific activity.

B. Extraction Method 2

The acetone powder (30 cjms) was then resuspended in 900 ml of extraction solution consisting of 20 mM potassium phosphate, pH 7.2, 20 um pyridoxal phosphate, 1.5 mM beta-mercaptoethanol, 1 mM EDTA, 50 uM TPCK and 5 uM PMSF. The resulting suspension was sonicated for approximately 3 min in a Branson Sonifier 450, and the sonicated suspension was left for 1 hr at 4 C. with mixing. Thereafter, the suspension was centrifuged at 13,000 rpm in a Sorval Model RC2-B centrifuge with a GSA rotor for 30 min. The resulting pellet was resuspended in 300 ml of extraction buffer and centrifuged as before to form a pellet. The supernatants from both centrifugations were collected and combined, and 25% (w/v) streptomycin sulfate was added dropwise to a final concentration of 1.0%. The precipitate was removed by recentrifugation as before, and the supernatant was collected to form a methioninase enzyme extract.

The methioninase enzyme extract was heated to 60' C. for 10 min in 300 ml aliquots, and cooled on ice to allow denatured proteins to precipitate. The resulting precipitate was removed by centrifugation at 13,000 rpm for 10 min as before, and the resulting supernatant was collected and dialyzed overnight against 10 liters of 10 mM potassium phosphate buffer, pH 7.2, containing 10 uM pyridoxal phosphate and 1.5 mM B-mercaptoethanol to form heat-treated methioninase enzyme dialysate.

The heat-treated dialysate (1200 ml) was applied to a Toyopearl-DEAE-650 (Japan) column (30×5 cm), pre-equilibrated with 10 mM potassium phosphate buffer, pH 7.2, containing 1.5 mM B-mercaptoethanol and 10 uM pyridoxal phosphate. The column was washed with 2.5 liters of 40 mM potassium chloride in 10 mM potassium phosphate buffer, pH 7.2, (wash buffer) until the optical density at 280 nm of the eluate was approximately 0.100. Thereafter, the chromatography was continued by an elution with a linear gradient of KCl at a concentration of from 40 to 300 mM in wash buffer. Elution fractions of 10 ml each were collected, assayed for methioninase activity as described earlier, and the active fractions were pooled.

A pool of methioninase-containing fractions (800 ml) was then adjusted to pH 8.3 and applied to a DEAE Sephadex-A50 column (30×3 cm) pre-equilibrated with 10 mM potassium pyrophosphate buffer, pH 8.3, (Sephadex loading buffer) containing 150 mM potassium chloride, 1.5 mM B-mercaptoethanol and 10 mM pyridoxal phosphate. The enzyme was then eluted with a linear gradient of 150 mM KCl to 500 mM KCl in Sephadex loading buffer. Elution fractions of 10 ml each were collected, assayed for methioninase activity, combined, the combined eluant fractions dialyzed overnight against 10 mM potassium phosphate buffer, pH 8.3, and then concentrated by adsorption on a 2×4 cm DEAE Sephadex column, pre-equilibrated with the same buffer. Thereafter, the enzyme was eluted with 10 mM potassium phosphate buffer containing 0.5 NaCl, and eluant fractions containing active enzyme were collected.

The degree of purification of methioninase is reported in Table 1.

TABLE 1

Table of Purification of Methioninase*

| Step | Volume (ml) | Protein (mg/ml) | Total Protein (mg) | Total Activity (units) | Yield (%) | Sp. Act. (U/mg) |
|---|---|---|---|---|---|---|
| 1 | 1200 | 5.0 | 6000 | 1005 | 100 | 0.16 |
| 2 | 1200 | 2.2 | 2640 | 1005 | 100 | 0.38 |
| 3 | 510 | 0.6 | 306 | 918 | 91 | 3.0 |
| 4 | 320 | 0.13 | 42 | 819 | 81 | 19.5 |

*Purification and yields of enzyme activity are shown for 30 gm of starting acetone powder obtained from 160 gms of crude cells. One unit of activity is an amount of enzyme that produces 1 μmole of alpha-ketobutyrate per 1 min, and specific activity is expressed as units (μmoles/min) per mg.

The yield of methioninase was 81%, as shown in Table 1. The specific activity increased from 0.16 U/mg to 19.5 U/mg, and the product is obtained using only three purification steps. The enzyme was analyzed on denaturing SDS-PAGE gels and shown to be a single homogeneous band of approximately 43 kilodaltons.

The purified enzyme prepared by Method 1 yielded an enzyme having a Km of $0.8 \times 10^{-3}$ M. Furthermore, at this stage of purification, the enzyme exhibited a strong endotoxin reaction when 1 unit of enzyme was administered in vivo to mice, indicating the necessity for removal of endotoxin even for this highly purified preparation of endotoxin.

The enzyme obtained at this stage of purification is different from the methioninase product isolated from *Pseudomonas ovalis* described by Tanaka et al, *FEBS Letts.*, 66:307–311 (1976), where a protein having two subunits were described. Methioninase protein was also isolated from *Pseudomonas ovalis* as described by ito et al., *Biochem.*, 79:1263–1272, (1976). However, the reported protocols of Tanaka et al. and of Ito et al. involve six purification steps. Furthermore, the methioninase isolated by Tanaka or by Ito did not exhibit a substantial yield, and the protein was of relatively low specific activity and unacceptably high endotoxin content for in vivo use.

Kreis et al., *Cancer Res.*, 33:1862–1865 (1973), isolated a methioninase from *Clostridium sporogenes* which exhibited a molecular weight of about 150 kilodaltons. However, the enzyme isolated exhibited a relatively low specific activity, and in particular had a serum half life of about four hours and an unacceptably high content of endotoxin. In addition, the purification procedure described by Kreis et al. produced a low yield of only about 1% and the enzyme was relatively unstable.

In view of the unacceptable levels of endotoxin observed in the purified enzyme, the resulting eluant fractions were further purified by removal of endotoxin as described below by either of two procedures.

(1) Endotoxin Removal Using Polymyxin

Solutions containing purified methioninase were further processed to remove endotoxin by adding 40 ul of 10% Triton-X-100 to 400 ul of enzyme solution containing approximately 1.5 mg of enzyme protein, 20 mM potassium phosphate, pH 7.4, 200 mM NaCl, 10 uM pyridoxal phosphate and 1.5 mM B-mercaptoethanol. The admixture was maintained for 10 min at 37 C. and then transferred to room temperature and applied to a 1 ml polymyxin agarose column (Sigma Chemical Co., St. Louis, Mo.). The enzyme was then eluted with 20 mM potassium phosphate buffer, pH 7.5, containing 200 mM NaCl and 1.0% Triton-X-100. Fractions containing methioninase activity were collected, and the amount of endotoxin was then determined on the eluate fractions.

Endotoxin was measured by a colorimetric limulus procedure following the manufacturer's specifications (Whittaker Bioproducts, Walkersville, Md.). Fifty ul of purified enzyme having a known amount of protein was added to 50 ul of Limulus solution, and the mixture was maintained for 10 minutes at 37° C. Thereafter, 100 ul of chromogenic substrate (Ac-Ile-Glu-Ala-Azg-pNA) was added and the mixture was incubated for an additional 6 min at 37 ° C. The reaction was then stopped by addition of 100 ul of 25% acetic acid, and the optical density at 410 nm of the reaction admixture was determined using *E. coli* endotoxin as a standard.

In initial studies, polymyxin was used without detergent in the adsorption and elution buffers. It was seen that pre-incubation of the enzyme with detergent prior to application to the polymyxin was required to separate the endotoxin from the enzyme.

(2) Endotoxin Removal Using Acticlean

Solutions containing purified methioninase were further processed to remove endotoxin by adding 200 ul of enzyme solution containing 500 ug of protein, 20 mM potassium pyrophosphate, pH 6.8, 250 mM KCl, 10 uM pyridoxal phosphate and 1.5 mM B-nercaptoethanol to a 1 ml column of Acticlean Etox (Sterogen Bioseparations, Arcadia, Calif.). The enzyme was then eluted from the column using the same buffer, and eluant fractions containing methioninase activity were collected, and the amount of endotoxin was then determined on the eluate fractions.

The endotoxin levels obtained after removal of endotoxin from the purified methioninase produced by Method 1 are shown in Table 2.

TABLE 2

| Endotoxin Removal Procedure | Protein (ug) | Endotoxin (ng/mg) | Total Activity |
|---|---|---|---|
| 1 | 500 | 44,000.0 | 9.0 U |
| 2 | 450 | 8.8 | 8.1 U |
| 3 | 100 | 40,000.0 | 1.7 U |
| 4 | 90 | 5.5 | 1.5 U |

The protein content, endotoxin concentration and total activity (expressed in units) was determined in Table 2 as described in Example 4. Samples obtained by procedures 1 and 2 were produced before (1) and after (2) chromatography using polymyxin, and samples obtained by procedures 3 and 4 were produced before (3) and after (4) chromatography using Acticlean as described in Example 4B.

The results shown in Table 2 indicate that the Acticlean chromatography method produced a substantial degree of removal of endotoxin, yielding approximately a ratio of protein to endotoxin of about $10^5$. The protein contained approximately 45 ug endotoxin per mg protein prior to the Acticlean step, and yielded a protein having about 8.8 ng endotoxin per mg of protein after the Acticlean step. This preparation of methioninase was tested for use in mice as described in Example 5, and shown to not exhibit significant endotoxin-mediated side effects in the mice.

To characterize serum half-life of methioninase purified by Method 2, four units of methioninase were injected i.p. into nude mice, and the blood levels of the methioninase and methionine were monitored. Methionine levels rapidly dropped from about 62 uM to below 20 um within one hour, reduced to as low as about 5 uM prior to 4 hours, and increased to 28 uM at about 7 hours. In the same study, methioninase serum levels increased uniformly to peak at about 2–3 hours, and gradually decrease to 50% levels at 7.5 hours. The serum levels of methioninase are therefore seen to persist for extended periods. In a similar study, 2 units of methioninase were injected i.v. and monitored. Serum levels decreased to about 50% after 100 minutes.

Therefore, the use of Method 2, combined with an endotoxin removal chromatography step provides a simplified and effective method to produce endotoxin-free methioninase in high yield suitable for use in in vivo therapeutic methods.

C. Extraction Method 3: Scaled Up Production of Methioninase

A strain of *Pseudomonas putida* was modified and selected for kanamycin resistance and for high levels of methioninase expression as follows:

ATCC 8209 *Pseudomonas putida* and ATCC 77100 *E. coli* were purchased from the ATCC in October 1993. ATCC 77100 was grown in LB (Sambrook et al., *Molecular Cloning: A laboratory manual* A.1, 1989) with 50 µg/ml kanamycin. Plasmid pCN 51, a shuttle vector containing a kanamycin resistance gene that is able to replicate in both *P. putida* and *E. coli* (Nieco et al., *Gene* 87:145–149, 1990, hereby incorporated by reference herein was isolated from ATCC 77100 and purified using the Triton-lysozyme method (Sambrook et al., *Molecular Cloning: A laboratory manual* 1.29–1.30, 1989). ATCC 8209 was grown in LB medium and transformed with pCN 51 using standard transformation procedures such as those described in, for example, Sambrook et al., *Molecular Cloning: a laboratory manual*. 1.74–1.84, 1989. The Kanamycin-resistant strain was selected with kanamycin (100 µg/ml) in LB medium and further grown in LB plates (Sambrook et al., *Molecular Cloning: A laboratory manual* A.1–A.4, 1989) in 100 µg/ml kanamycin. A single colony was grown in 100 µg/ml kanamycin in LB overnight and then put under high-methioninase-expression conditions: 10% LB, 0.1% potassium phosphate buffer pH 7.2, 0.1% urea, 0.025% yeast extract, 0.01% magnesium sulfate and 0.25% methionine with 50 µg/ml kanamycin for 24 hours. The expression of methioninase was measured with the standard methioninase assay as described herein. The methioninase over-producing strain of *Pseudomonas putida* was selected and named as AC-1.

A scaled up fermentation process for AC-1 *Pseudomonas putida* was then employed. An AC-1 single colony was grown in an LB plate containing 50 µg/ml kanamycin. The selected colony was incubated in 5 ml LB containing 50 µg/ml kanamycin at 26° C. with shaking at 250 rpm/min for 18 hours. Two ml of bacteria were amplified in 600 ml LB containing 50 µg/ml kanamycin at 26° C., with shaking at 200 rpm/min for 6 hours. Then 50 ml of bacteria were incubated in 2 liters LB containing 50 µg/ml kanamycin at 26° C. with shaking at 100 rpm/min overnight (18 hours). Two liters of bacteria ($OD_{600}$ 1.2–1.6) were then grown in a 40-liter tank in a special medium which contained 10% LB, 0.1% potassium phosphate buffer pH 7.2, 0.1% glycerol, 0.1% urea, 0.025% yeast extract, 0.01% magnesium sulfate and 0.25% methionine under high aeration conditions at 26° C. for 24 hours. The $OD_{600}$ reached 1.2–1.8 and the activity reached 20–30 units/liter. The optimal cell density for harvesting is an $OD_{600}$ of 1.5–1.8, with 2–3 mg/l of methioninase. This is equivalent to 1 kg of wet cells/400 liters. Preferably, a fully-equipped fermenter would be used with an approximate yield of 1 kg wet cells/10–20 liters. The cells were harvested with an AGT column (Model UFP-500-E-55 cartridge, A/G Technology Corporation) keeping the temperature at 4° C. then centrifuged using an automatic refrigerated centrifuge (Sorvall superspeed RC2-B) at 4° C., at 9 krpm for 10 minutes. The cell pellet was then collected.

The cells were then suspended in extraction solution (20 mM potassium phosphate, pH 9.0) at a density of 500 g wet cells/liter, and disrupted using three passages with a cavitator homogenizer (Microfluidics Corp. Model #HC 8000). The homogenate was stored at −80° C. immediately after cell breakage. The specific activity of methioninase in the homogenate was 0.08–0.1 units/mg protein.

The AC-1 homogenate was suspended in extraction buffer (10 mM potassium phosphate pH 7.2, 10 uM pyridoxal phosphate, 0.01% beta-mercaptoethanol, 1 mM EDTA and 20% ethanol and was heated at 50° C. for 2 minutes. The heating step may be performed for any length of time sufficient to precipitate heat-sensitive contaminating proteins while maintaining methioninase activity. The suspension was centrifuged at 12 krpm at 4° C. for 30 minutes. The supernatant was collected and ultrafiltered with a Millipore Prep/Scale-TFF PLHK 100k2.5 ft2 cartridge. The pH was then adjusted to 7.2.

A sample of about 25–35 g of total protein in 10 L extraction buffer (10 mM potassium phosphate buffer pH 7.2 10 µM pyridoxal phosphate and 0.01% β-mercaptoethanol) was applied to a Toyopearl DEAE-650M column 10 cm×50 cm which was pre-equilibrated with 10 mM potassium phosphate buffer (pH 7.2). The column was pre-washed with 20–30 L of 40 mM potassium chloride in 10 mM potassium phosphate buffer, pH 7.2 containing 10 µM pyridoxal phosphate and 0.01% beta-mercaptoethanol, until the $OD_{280}$ dropped below 0.1. The column was then eluted with a linear gradient of potassium chloride at concentrations starting at 40 mM, increasing up to 300 mM in extraction buffer. Elution fractions of 400 ml were collected. The fractions containing methioninase were determined by methioninase activity assay as described herein and were pooled. The pooled fractions were pre-equilibrated with 10 mM potassium phosphate buffer, pH 8.3, containing the same concentration of pyridoxal phosphate and beta-mercaptoethanol, and 150 mM potassium chloride.

A sample of about 1–2 g of total protein obtained from the methioninase peak of the DEAE-650M (5 cm×20 cm) column in buffer containing 10 mM potassium phosphate pH 8.3, 150 mM potassium chloride, 10 µM pyridoxal phosphate and 0.01% β-mercaptoethanol was applied to a DEAE-Sephadex A50-column. The column was eluted with a 150–500 mM Kcl linear gradient in 10 mM potassium phosphate buffer, pH 8.3 containing 10 µM pyridoxal phosphate and 0.01% beta-mercaptoethanol. Elution fractions of 150 ml were collected. The fractions containing methioninase determined by activity assay as described herein were pooled. The pooled methioninase was then further purified to remove endotoxin. The sample was pre-equilibrated by dialysis in 0.12M sodium chloride and 10 mM sodium phosphate buffer, pH 7.1. The sample was applied to a 5 cm×15 cm Acticlean Etox resin column (Sterogen Bioseparations, Arcadia, Calif.). The enzyme was then eluted from the column using the same buffer, eluant fractions containing methioninase activity were collected, and the amount of endotoxin was then determined on the eluted fractions. Table 3 shows the results of this purification method.

TABLE 3

SCALE UP OF METHIONINASE MANUFACTURING PROCESS

| Step | Volume (ml) | Activity units/ml | Activity total | Protein mg/ml | Protein total (g) | Specific Activity (units/mg) | Yield PH (%) |
|---|---|---|---|---|---|---|---|
| Homogenate | 3850 | 1.05 | 5200 | 11.5 | 44.3 | 0.1 | 6.7 | 100 |
| Heat | 3130 | 1.43 | 4472 | 4.4 | 13.8 | 0.33 | 6.9 | 86 |
| Ultra-filtration | 2950 | 1.41 | 4160 | 4.25 | 12.5 | 0.33 | 7.2 | 80 |
| First Column | 850 | 4.42 | 3744 | 1.64 | 1.39 | 2.6 | 7.2 | 72 |
| Second Column | 1000 | 3.22 | 3220 | 0.22 | 0.22 | 14.6 | 8.3 | 62 |
| Third Column | 540 | 4.8 | 2620 | 0.34 | 0.18 | 14.3 | 7.1 | 52 |
| Concentration | 16.5 | 153 | 2529 | 10.5 | 0.173 | 14.8 | 7.1 | 48 |

FIG. 1a shows the result of the analysis of the purified methioninase on a 7.5% SDS-PAGE gel. A single band of protein of 43 kd, representing one subunit of the 172 kd protein was observed when the active fractions from the second column were analyzed by SDS-PAGE. The purity of the methioninase isolated by this method was 98.7% as shown in FIG. 1b by HPLC analysis, which demonstrated only one peak of protein.

The use of Method 3, also provided an endotoxin-free methioninase and is a preferred method of isolating larger amounts of endotoxin-free methioninase. Those of ordinary skill in the art will recognize that modifications may be made to the extraction methods described in and are included within the scope of the invention.

The extraction methods described herein resulted in a preparation of substantially isolated methioninase that was substantially free of endotoxin.

5. Depletion of Methionine in Mice Using Methioninase

The in vivo effectiveness, and physiological tolerance, of methioninase for use according to the present invention was demonstrated by administration of the enzyme to mice as follows.

In one study, mice were fed normal chow (containing methionine) ad libidum. About 1.5 U of methioninase produced according to Method 1 in Example 4 was injected intravenously three times at three hour intervals. About one hour after the last injection, the blood concentration of methionine was assayed. The above treatment produced serum methionine levels of from about 3 to 5 uM, depending on the animal. Methionine was assayed by subjecting 50 ul of serum from the mouse to derivitization with PITC which was then analyzed by reverse phase FPLC, and comparing the chromatographic profile to internal methionine standards. The sensitivity of the assay was about 0.5 uM methionine.

None of the mice exhibited any observable deleterious responses to the injections.

In another experiment, mice were fed a methionine-free diet of chow (TD 92077, from Teklad, Inc., Madison, Wis.) for about 2 months. Thereafter, the serum concentrations of methionine were measured and were observed to vary broadly. However, no mouse exhibited serum levels below about 5 uM methionine when the treatment consisted of a methionine-free diet. The methionine starved mice were then injected intravenously with about 1.5 U methioninase three times every three hours, and the serum methionine concentrations assayed about one hour after the last injection as described above. The serum levels in mice so treated were consistently below detectable levels. Thus, the combined use of methionine depletion and methioninase administration under the above conditions substantially reduced circulating methionine levels to at least below 0.5 uM methionine.

Figure 2:
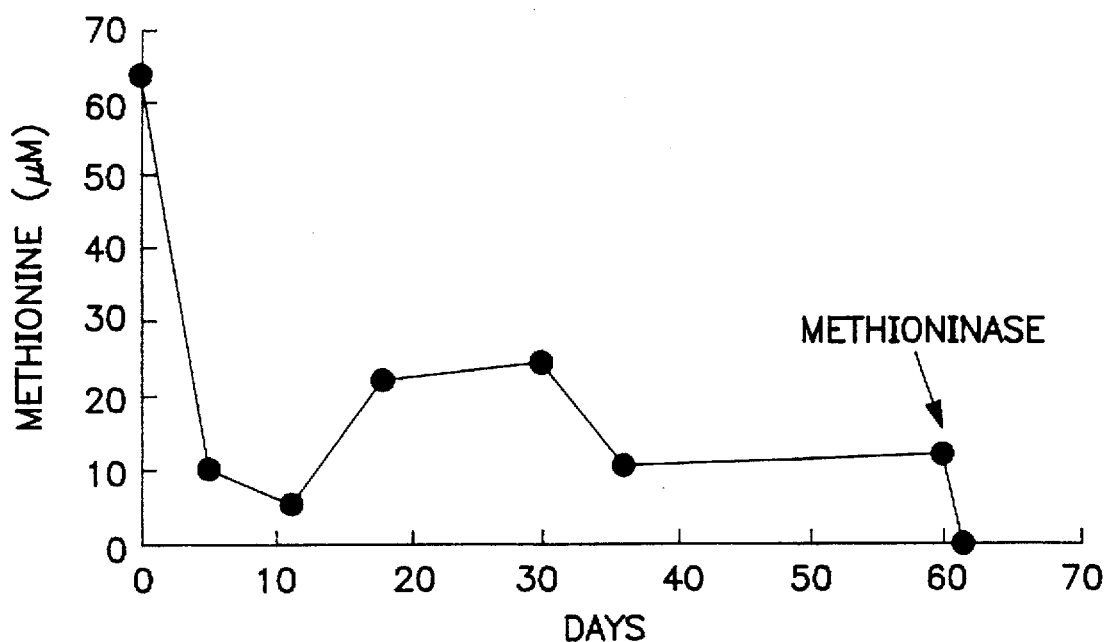
FIG. 2 is a graph that illustrates the in vivo depletion of methionine during administration of a methionine-free diet and upon intravenous addition of methoninase as described in Example 5. Methionine (METH) is measured and expressed in micromolar (uM) concentrations of from 0 to 65 uM over about 65 days.

The results of methionine starvation and methioninase addition is represented over a sixty day period in FIG. 2.

Figure 3:
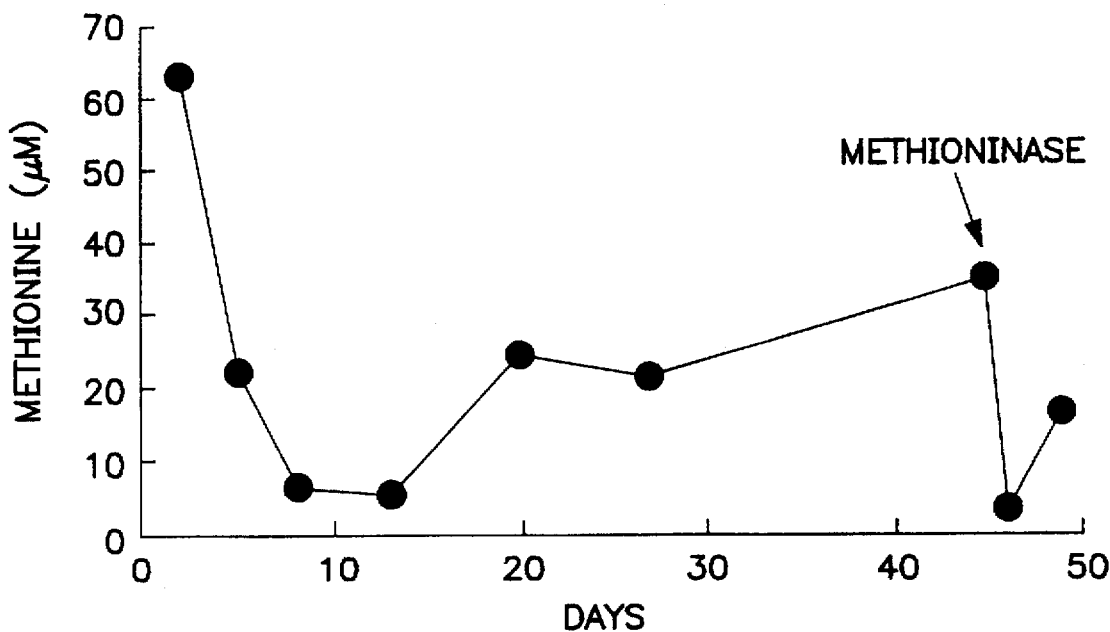
FIG. 3 is a graph that illustrates the in vivo depletion of methionine during administration of a methionine-free diet in which homocysteine is added at day 14 (open arrow) and upon intravenous addition of methoninase as described in Example 5. Methionine (METH) is measured and expressed in micromolar (uM) concentrations of from 0 to 65 uM over about 50 days.

In a related experiment, mice were similarly starved for methionine, except that homocysteine was added to their diet at about day 14, as indicated by the open arrow shown in FIG. 3, and homocysteine supplement continued thereafter, all at an amount of 8.25 gm homocysteine per kg of chow. The levels of serum methionine were observed to rise consistently above 20 mM until methioninase prepared according to Method 1 in Example 4 was added at about day 45, whereupon the serum level of methioninase dropped dramatically and rapidly to about 3.5 uM. Thus, the presence of homocysteine does not limit the effectiveness of the present starvation and methioninase treatment methods.

Further studies were conducted using methioninase at higher levels, where endotoxin contamination could produce toxic side effects. Therefore, the endotoxin-free methioninase prepared as described in Method 2 of Example 4 was used in in vivo studies.

Outbred nude mice nu+/nu+ (4–5 weeks old) were divided randomly into 3 groups, and bred and housed in a HEPA filtered barrier room under NIH guidelines. A fresh culture of Yoshida sarcoma cells, grown in suspension culture using Eagle's medium and 10% fetal calf serum (FCS), were injected ($7.3\times10^5$ cells) into each mouse at the axillary site. Mice in Group One were the control group mice, and were fed a methionine-containing diet (MET$^+$). Mice in Group Two were fed a methionine-free diet (MET$^-$). Mice in Group Three were fed a (MET$^-$) diet and were treated with methioninase.

Diets were premeasured and defined as diets with (MET$^+$) or without (MET$^-$) methionine (#TD939030 and #TD939077, respectively), and were obtained from Teklad (Madison, Wis.).

In a preliminary experiment, methioninase produced by Method 2 was given by intraperitoneal injection (I.P.) to Group Three mice in increasing amounts until the growth of the tumors was arrested, typically at about 40 units/day. In two subsequent experiments, 4 units of methioninase was injected i.p. into each Group Three mouse every 2 hours for 7 and 10 days, respectively. In the first experiment, methioninase treatments were started on day 2, and in the second experiment, treatment was started on day 0.

Tumor weight and mouse body weight was monitored. The length of the minor and major axis of the Yoshida sarcoma growing in each nude mouse was measured with calipers each day of the experiment. Tumor weight was calculated as estimated tumor weight (ETW), using the equation of Goseki et al., Cancer, 69:1865–1872 (1992). Body weight was calculated as measured total body weight minus ETW. Data for tumor growth rates were analyzed by comparisons of slopes of a Student's t-Test of the population regression coefficients as described by Zar, J. H., in "Biostatistical Analysis", Prentice Hall, N.J., 1984, pp. 292–297, modified by using linear regression for each mouse and then comparing the mean coefficient for each group as described by Zar. This analysis allows for the change in the number of mice due to death before the end of the experiment. Percent inhibition is expressed relative to the control Group One, and is calculated as $100\times[1-(\text{mean of ETW for treated group/mean of ETW for control group})]$.

In the preliminary experiment using escalating doses of Method 2 methioninase, doses at 13 and at 24 units a day still allowed slight tumor growth, although substantial inhibition of tumor growth was observed. Dosages were then raised to 40 units per day which greatly slowed tumor growth.

Figure 4:
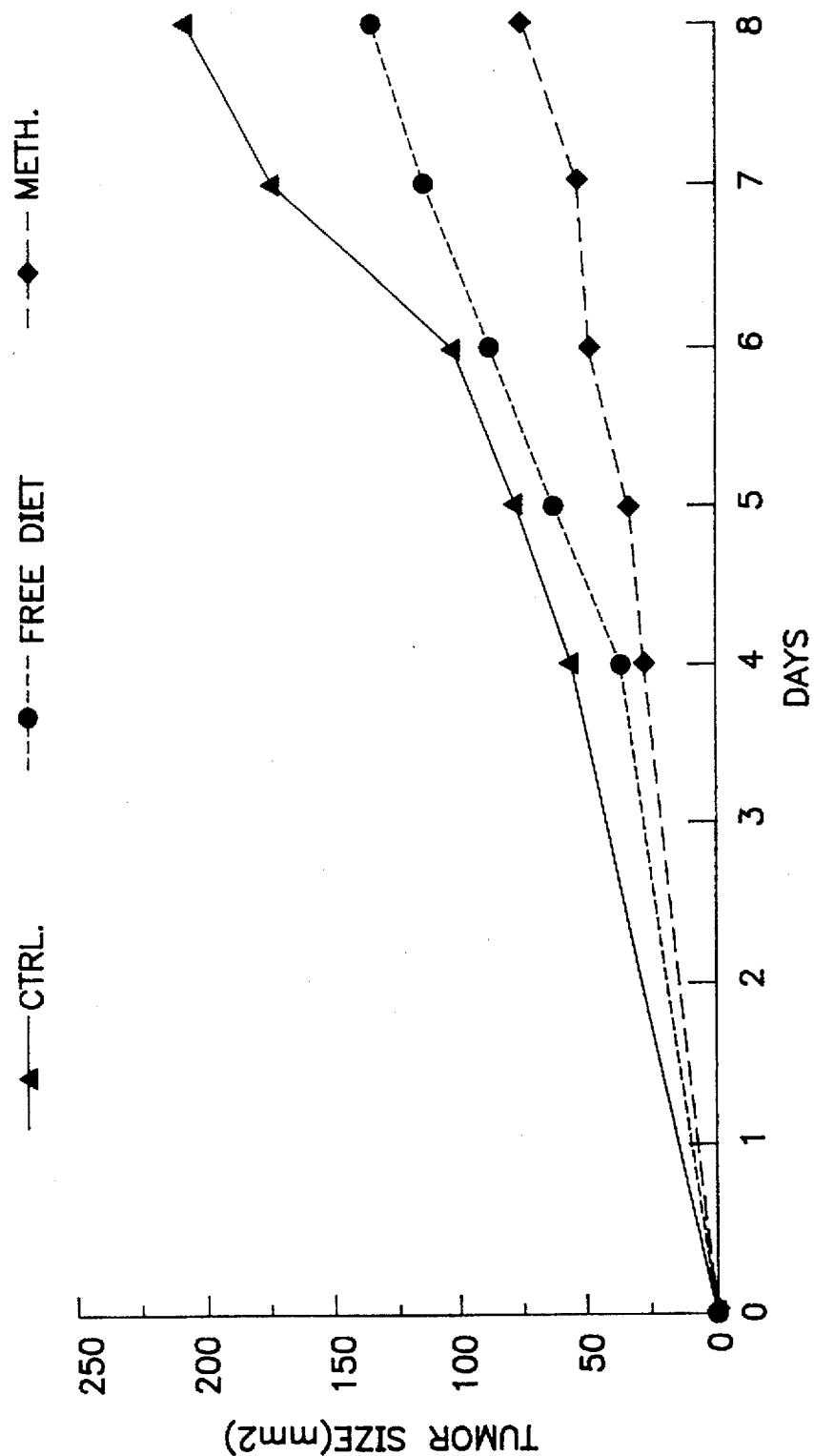
FIG. 4 is a graph that illustrates the efficacy of methioninase in reducing Yoshida Sarcoma growth in mice. Tumor size is plotted as a function of the number of days of treatment.
Figure 5A:
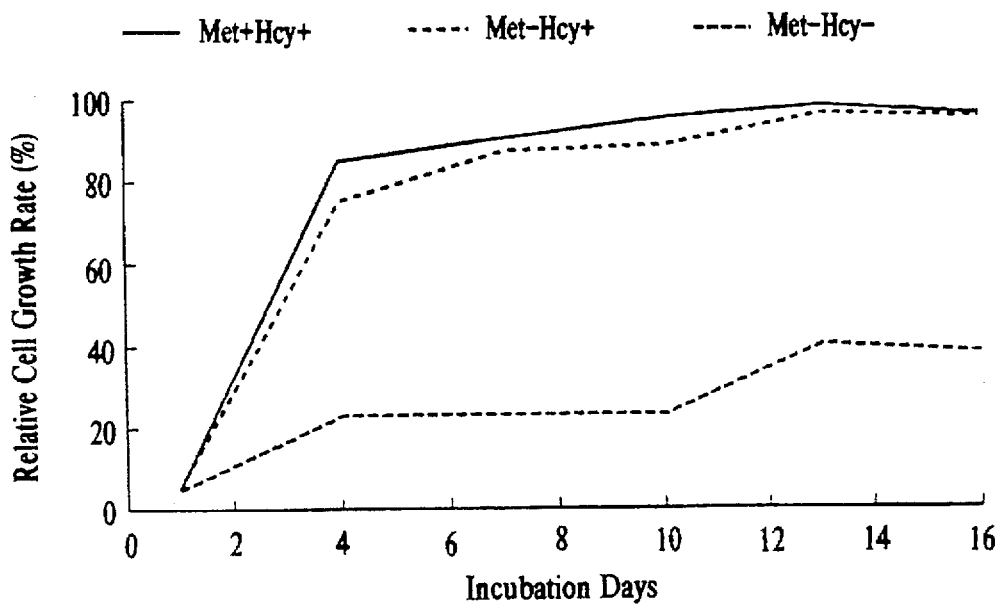
FIG. 5 is a compilation of 6 graphs illustrating the growth of tumor cell lines in methioninase-free, homocysteine-free, or methioninase and homocysteine-free media.
Figure 5B:
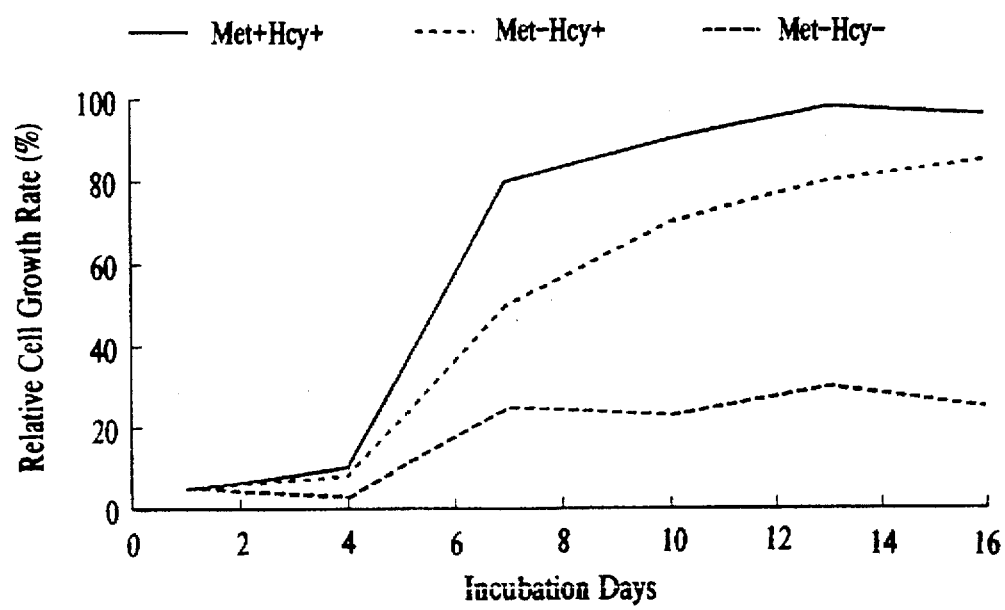
Figure 5C:
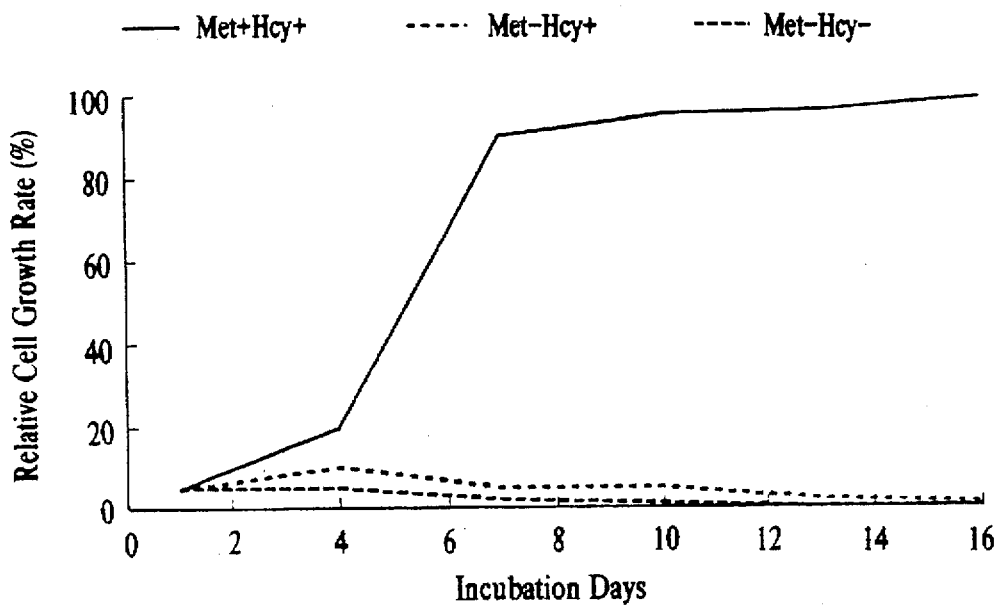
Figure 5D:
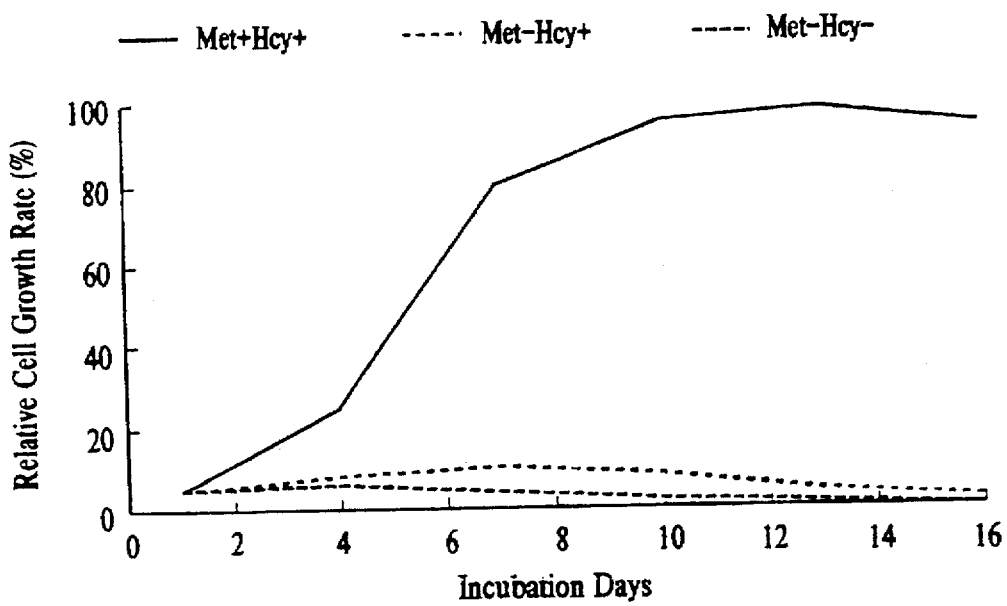
Figure 5E:
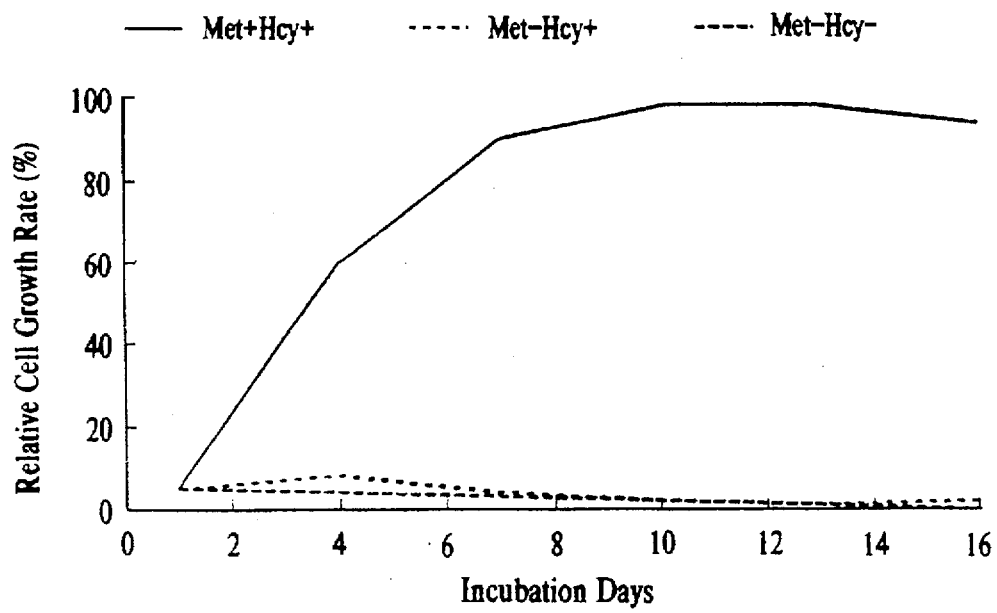
Figure 5F:
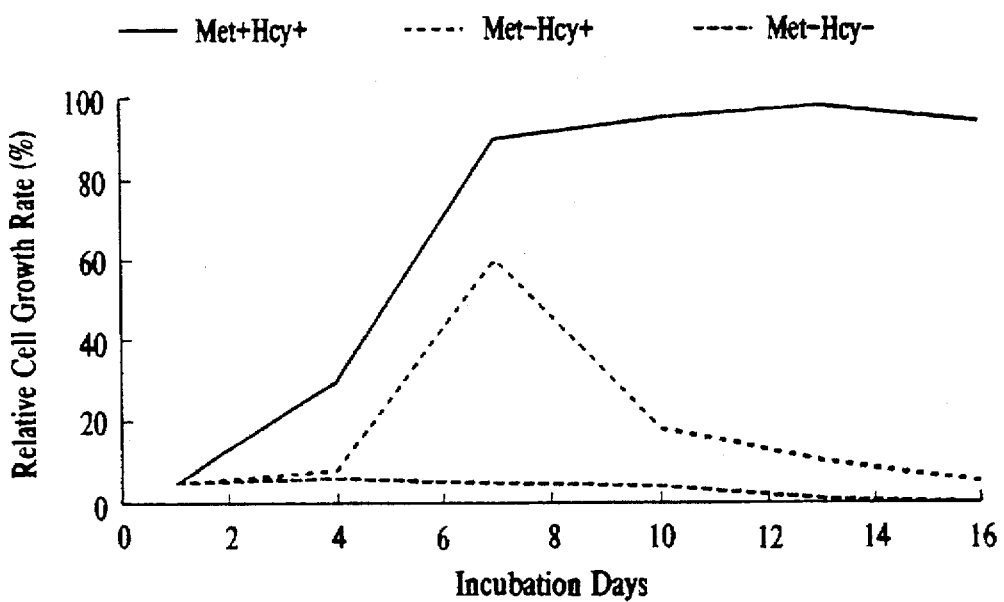

Table 4 and FIG. 4 show the results obtained in the two experiments in which 40 units of methioninase were used daily.

TABLE 4

Effectiveness of Methioninase at Inhibiting Yoshida Sarcoma Growth in Mice[a]

| Group | Estimated Tumor Weight | Inhibition (percent) | Growth Rate |
|---|---|---|---|
| EXPERIMENT I | | | |
| 1 | 233.64 | — | 39.04 |
| 2 | 189 | 19% | 25.2 |
| 3 | 48 | 79% | 8.72 |
| EXPERIMENT II | | | |
| 1 | 813.18 | — | 35.78 |
| 2 | 674.18 | 17% | 25.4 |
| 3 | 258.0 | 68% | 18.21 |

[a]Group One mice are the control, fed a MET$^+$ diet; Group Two mice are fed a MET$^-$ diet; and Group Three mice are fed a MET$^-$ diet plus received 40 units/day of methioninase as described in Example 5. Estimated Tumor Weight (ETW) is expressed in milligrams as a mean weight on the last day of the experiment. Percent Inhibiton was calculated as described in the text. Growth Rate is expressed as the slope of tumor growth curve calculated as the regression coefficient.

As can be seen in Table 4, 40 units/day of methioninase were effective in preventing significant tumor growth in comparison to untreated animals on a normal or methionine-depleted diet. In particular, whereas a methionine-depleted diet in Group Two mice reduced tumor growth rates in comparison to Group One mice, methioninase treatment (Group Three) substantially increased the effectiveness of the therapy at inhibiting tumor growth rates.

In the first experiment, Yoshida sarcoma-bearing mice receiving 40 units/day of methoninase caused a 79% inhibition of tumor growth. In the second experiment, the same treatment caused a 68% inhibition of tumor growth. In contrast, Group Two mice on a MET⁻ diet without methioninase treatments exhibited tumor growth inhibition of only 19% and 17% in these two experiment, respectively. Furthermore, the growth rate data indicates that the Yoshida sarcoma was essentially arrested in growth rate by the combined methoninase treatment and methionine-free diet compared to the control growth rate.

These data show that the combined use of methionine-free diet with methoninase administration is very effective at inhibiting tumor growth in vivo. In particular, it is noted that the methods demonstrated here were effective at inhibiting the growth of a Yoshida sarcoma, which is a very malignant tumor type.

Mice in Group Three given methoninase produced by Method 2 did not exhibit signs of pyrogenic reactions typically indicative of unacceptable levels of endotoxin.

Cells from the implanted sarcoma of mice in Group One, Two and Three were analyzed for DNA content as described in Example 1 to determine whether the tumor cells exhibited methionine dependence when treated in vivo with the methionine-depletion methods of a methionine-free diet combined with administration of methoninase. Mice containing Yoshida sarcoma tumors are arrested in the cell cycle by methoninase, as evidenced by an MDCCB value of 0.52 obtained from the tumors analyzed in the second experiment, indicating methionine dependence of Yoshida sarcoma in vivo.

Normal colon tissue analyzed similarly exhibited a MDCCB value of 0.98, indicating methionine independence.

Earlier studies with methoninase by us and others did not demonstrate the present effectiveness for several reasons. The quality of the methoninase enzyme used previously was very low, and the endotoxin levels prevented use of the required dosages of methoninase for effective inhibition. Therefore, earlier studies did not show that methoninase therapies could be significant at inhibiting tumor cell growth. In addition, earlier studies did not demonstrate the ability to specifically synchronize tumor cells useful in the anti-mitotic therapies described herein.

6. Synergy Using Competitive Inhibitors of Methionine

To increase the metabolic effectiveness of methionine depletion, the use of competitive inhibitors of methionine-utilizing enzymes reduces the utilization of any methionine available under depletion conditions, and therefore (1) further reduces the normal bioconversion of methionine into its essential metabolic pathways and (2) would increase availability of methionine for conversion by methoninase.

A. In Vitro Efficacy of Ethionine

Cells of the Yoshida sarcoma cell line were inoculated at $5 \times 10^3$ cells per 5 ml. The cells were then cultured in Earle's MEM media with 10% FCS containing methionine at 5, 10 or 100 uM, and further containing ethionine at 5, 50, 100, 500 or 1000 uM in varying combinations with the methionine. Cells were counted daily.

Ethionine at 50–100 uM had no effect on the growth of Yoshida sarcoma in vitro when methionine was present at 10 uM. When methionine was at 5 uM, 50 uM of ethionine had no effect whereas 500 uM ethionine completely inhibited cell growth. Thus, the ethionine was effective at inhibiting methionine dependent Yoshida sarcoma cells under conditions of limiting methionine. Particularly, the ethionine was effective when present at a ratio of methionine/ethionine of 1:20 or lower relative amounts of ethionine.

B. In Vivo Efficacy of Ethionine

Four groups of nude mice were selected randomly as in Example 5, each consisting of three mice. $8 \times 10^5$ Yoshida sarcoma cells were injected at an axillary site in each mouse. Group I and III mice were fed the methionine-containing diet, and Group II and IV mice were fed the methionine-free diet. Group III mice were given ethionine i.p. twice daily at 25 mg/kg, and Group IV mice given ethionine i.p. twice daily at 25 mg/kg. Other Group IV mice were given 7.5–30 mg/kg to see the effects of other dosages.

Tumor size, body weight and DNA content were measured and analyzed as described in Example 5. In addition, mouse tissues were analyzed histologically for metastases. To that end, liver, lung, kidney and colon of the mice were fixed in 10 formalin after the mice died. The tissues were dehydrated, embedded in paraffin and sectioned. Slides were stained with hematoxylin and eosin, and analyzed by light microscopy.

Table 5 shows the results of the treatment on Groups I–IV mice.

TABLE 5

Effect of Ethionine and Methionine on Tumor Growth*

| Condition | Inhibition Rate |
|---|---|
| Group I Met⁺ | 0.0 |
| Group II Met⁻ | 64.3% |
| Group III Met⁺ + Ethionine | 7.5% |
| Group IV Met⁻ + Ethionine | 87.1% |

*Treatment was conducted as described in Example 6. Inhibition Rate was calculated as of day 9 by the equation [tumor size (control) − tumor size (treated)]/tumor size (control).

The data in Table 5 shows that ethionine in the presence of methionine was ineffective (Group III), whereas ethionine at 25 mg/kg increased the effectiveness of the methionine starvation diet at inhibiting tumor cell growth (Group IV compared to Group II). Ethionine used at 7.5 mg/kg or 15 mg/kg exhibited a lesser but measurable effect on the growth of the tumor cells under methionine starvation conditions.

The body weight of the animals receiving ethionine an a methionine-free diet was essentially the same as the body weight of Group II mice over the course of the treatment, indicating that ethionine does not produce any unacceptable side effects to body weight.

The metastases of Yoshida sarcoma normally observed under normal conditions (without treatment) was completely inhibited by the ethionine treatment. Whereas 75% of organs from Group I (Met⁺) exhibited metastases and 42.8% of organs from Group II (Met⁻) exhibited metastases, a striking 0.0% of organs from Group IV (Met⁻ plus 25 mg/kg ethionine) exhibited metastases. Thus, the use of competitive inhibitors of methionine in combination with methionine depletion completely blocked metastasis formation. This is particularly noteworthy because the Yoshida sarcoma is highly metastatic.

The use of ethionine as a competitive inhibitor of methionine during methionine starvation also produced enhancement of the synchronization of tumor cells previously observed using other methionine depletion methods (e.g., methionine-free diets and/or methoninase treatment). For example, following the above methionine treatments, the DNA contents analyzed in Groups I–IV mice revealed that the methionine administration in vivo increased the DNA content of the cells in the Yoshida sarcoma of mice fed the MET⁻ diet compared to mice on the MET⁻ diet without methionine supplements, indicating that methionine synergistically improves the ability of methionine starvation to arrest tumor cells in a late phase of the cell cycle. Furthermore, normal cells of the mouse colon were evaluated for DNA content, and were unaffected by any of the treatments (Group II–IV), indicating that the methionine/ MET⁻ treatment selectively arrests the tumor cells, and not normal cells, in the late S/G$_2$ phase of the cell cycle. The arrest was reversible upon cessation of the methionine treatment and particularly upon administration of excess methionine, allowing a wave of tumor cells to enter mitosis synchronously.

7. Dependence of Human Tumors on Elevated Levels of Methionine

Methionine dependence occurs frequently in human cancer. Twenty NCI human tumor cell lines from all major organ systems were tested for methionine dependence. All twenty cell lines were found to be methionine dependent. In addition, fresh human tumor specimens were tested and found to be methionine dependent. Normal human cell lines were not methionine dependent.

FIG. 5 shows the results of one such test. In FIG. 5, normal cell strains and tumor cell lines were grown in Eagle's MEM with 10% dialyzed serum that was either: methionine-containing homocysteine-free (MET⁺HCY⁻); methionine-free, homocysteine-containing (MET⁻HCY⁺) or methionine-free, homocysteine-free (MET⁻HCY⁻). Kidney, colon, lung and prostate cancer cell lines and melanoma and normal fibroblast strains were screened in methionine (MET)-containing medium, MET-free medium, homocysteine (HCY)-containing medium and in MET-free medium, homocysteine (HCY)-containing medium and in MET-free, HCY-free medium. The cells were grown in Eagle's Minimum Essential medium (MEM medium) supplemented with 10% dialyzed fetal bovine serum, 10 µM hydroxocobalamin and 100 uM folic acid. The medium was supplemented with or without methionine in the following way: MET+HCY: The medium was supplemented with 100 µM L-methionine without homocysteine. METHCY+: The medium was supplemented with 200 µM D,L-homocysteine without methionine. METHCY: The medium was methionine-free and homocysteine-free. The fetal bovine serum was dialyzed against phosphate buffered saline (PBS) (serum:PBS of 1:12) 10 times.

Cell proliferation was determined by metabolic reduction of the dye XTT as measured by absorption at 450 nm. Cells were grown on 48-well dishes by inoculation of between 5×10³ and 2×10⁴ cells per well. XTT (2,3-bis(2-methoxy-4-Nitro-5-sulfophenyl)-5-[(phenylamino)carbonyl]-2H-tetrazolium hydroxide), which is metabolically reduced in viable cells to a water soluble formazan product was used to determine cell proliferation. The absorbance of the reduced product was measured at 450 nm. XTT was prepared at 1 mg/ml in pre-warmed (37° C.) PBS. Phenazine methosulfate (PMS) was prepared at 5 mM in PBS. Fresh XTT solution was mixed with PMS stock solution at a ratio of 5 µl PMS per 1 ml XTT. Each well was filled with 1 ml medium. 0.25 mL of mixed XTT were added to each well. The absorbance of reduced XTT was read at 450 nm with a Hitachi U-2000 spectrophotometer after 3 hours of incubation. The OD of XTT was measured every 3 days after the cells were cultured for an initial 24 hours. Foreskin fibroblast strains FS-3 and HS-68 proliferated essentially equally in MET⁺HCY⁻ or MET⁻HCY⁺. However, a new observation is reported here in that both fibroblast strains could proliferate to some degree and then maintain themselves for at least 16 days in MET HCY medium.

Table 6 illustrates the results of a cell proliferation assay of 20 tumor cell lines. In the assay, 5×10³–2×10⁴ cells/well of cell suspension were cultured in 48-well plates in MEM with 10% fetal bovine serum for 24 hours. Cells were washed with Hanks basic salt solution (HBSS) twice and then were divided into 3 groups. Group I: Cells cultured in MET⁺HCY⁻ medium; Group II: Cells cultured in MET⁻HCY⁻ medium; Group III: Cells cultured in MET⁻HCY⁻ medium. Cells were cultured in a gassed incubator with 95% air/5% CO$_2$. The media were changed every 2–3 days. In Table 6, strong growth of the cell lines is indicated with a +++, some growth with a ++, slight growth with a + and no growth with a –. Approximately one-half of the tumor cell lines could not grow in the MET-free HCY-containing medium with the rest growing to varying degrees whereas the same medium allowed the normal cells to grow as well as in MET-containing medium. Although the normal cell strains could grow to some extent and then maintain themselves for two weeks or more in MET-free, HCY-free medium, all 20 tumor cell lines tested died in this medium suggesting that potentially all cancers can be selectively killed by MET deprivation. This example provides more evidence that methionine dependence may be a universal and selective target for cancer therapy, especially with methioninase as the therapeutic.

TABLE 6

| CELL LINES | TYPE OF CANCER CELL | PROLIFERATION | | |
|---|---|---|---|---|
| | | MET⁺HCY⁻ | MET⁻HCY⁻ | MET⁻HCY⁻ |
| Tumor | | | | |
| A498 | Renal | +++ | – | – |
| CAKI | Renal | +++ | ++ | – |
| SN12C | Renal | +++ | + | – |
| RXF-393 | Renal | ++ | + | – |
| DU-145-1 | Prostate | +++ | – | – |
| PC-3 | Prostate | +++ | – | – |
| H322M | Lung | +++ | – | – |
| H23 | Lung | +++ | +++ | – |
| SNB-75 | CNS | +++ | ++ | – |
| SF-295 | CNS | +++ | ++ | – |
| H460 | CNS | +++ | – | – |
| H522 | CNS | +++ | ++ | – |
| HCT-15 | colon | +++ | – | – |
| Colo 205 | Colon | +++ | +++ | – |
| SW-620 | Colon | +++ | – | – |
| HT29 | Colon | ++ | + | – |
| UACC-257 | Melanoma | +++ | +++ | – |
| UACC-62 | Melanoma | +++ | +++ | – |
| SK-MEL-5 | Melanoma | ++ | + | – |
| Lox | Melanoma | ++ | – | – |
| Normal Cells | | | | |
| FS-3 | Foreskin | +++ | +++ | + |
| HS-68 | Foreskin | +++ | +++ | + |

8. Inhibition of Human Tumor Growth by Methioninase in Mouse Xenograft Models

Figure 6:
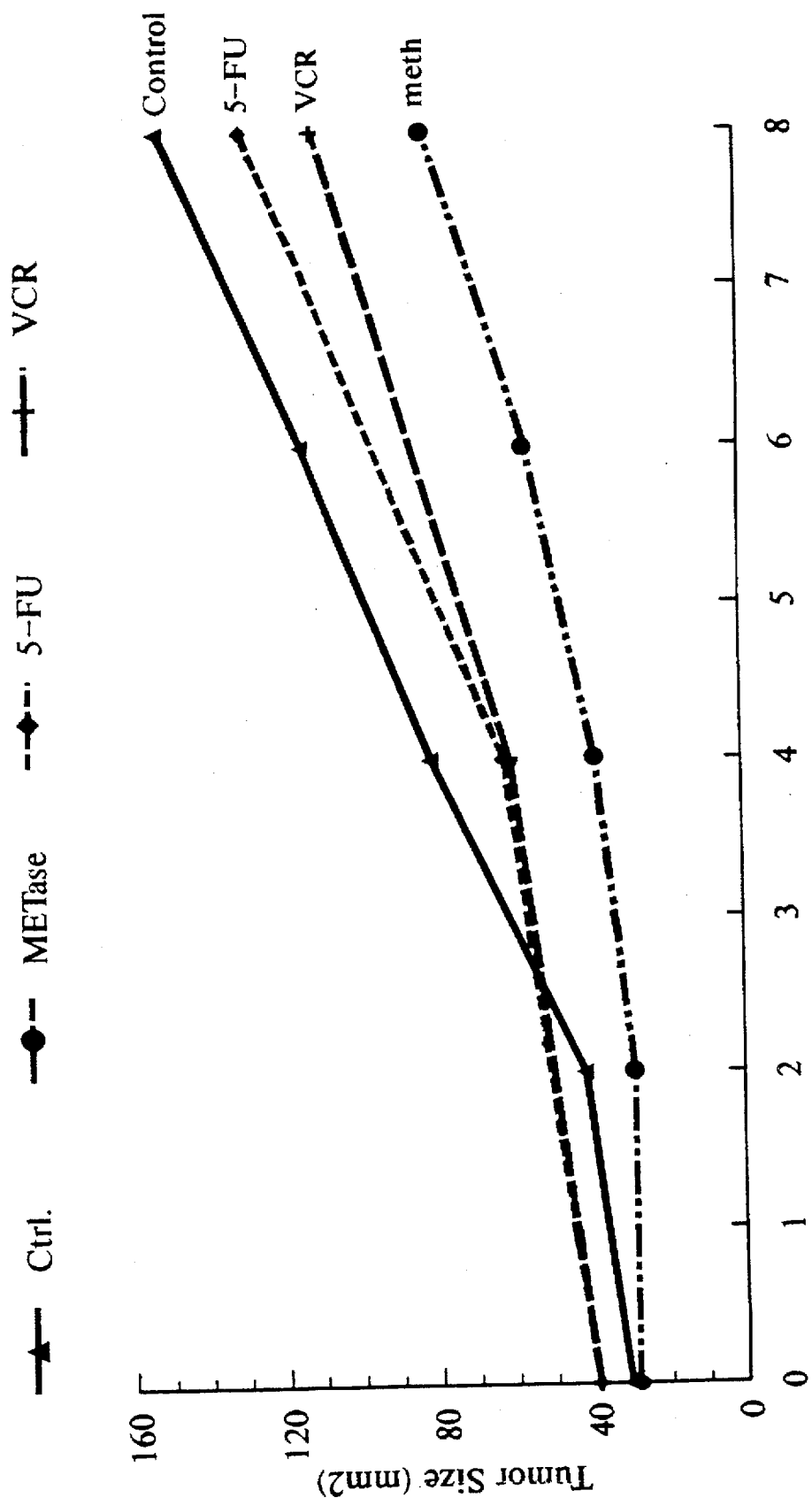
FIG. 6 is a graph that illustrates the efficacy of methioninase for reducing the level of human lung tumor (H460) growth in mouse xenografts. The results of 5-FU and vincristine treatment are also illustrated.
Figure 7:
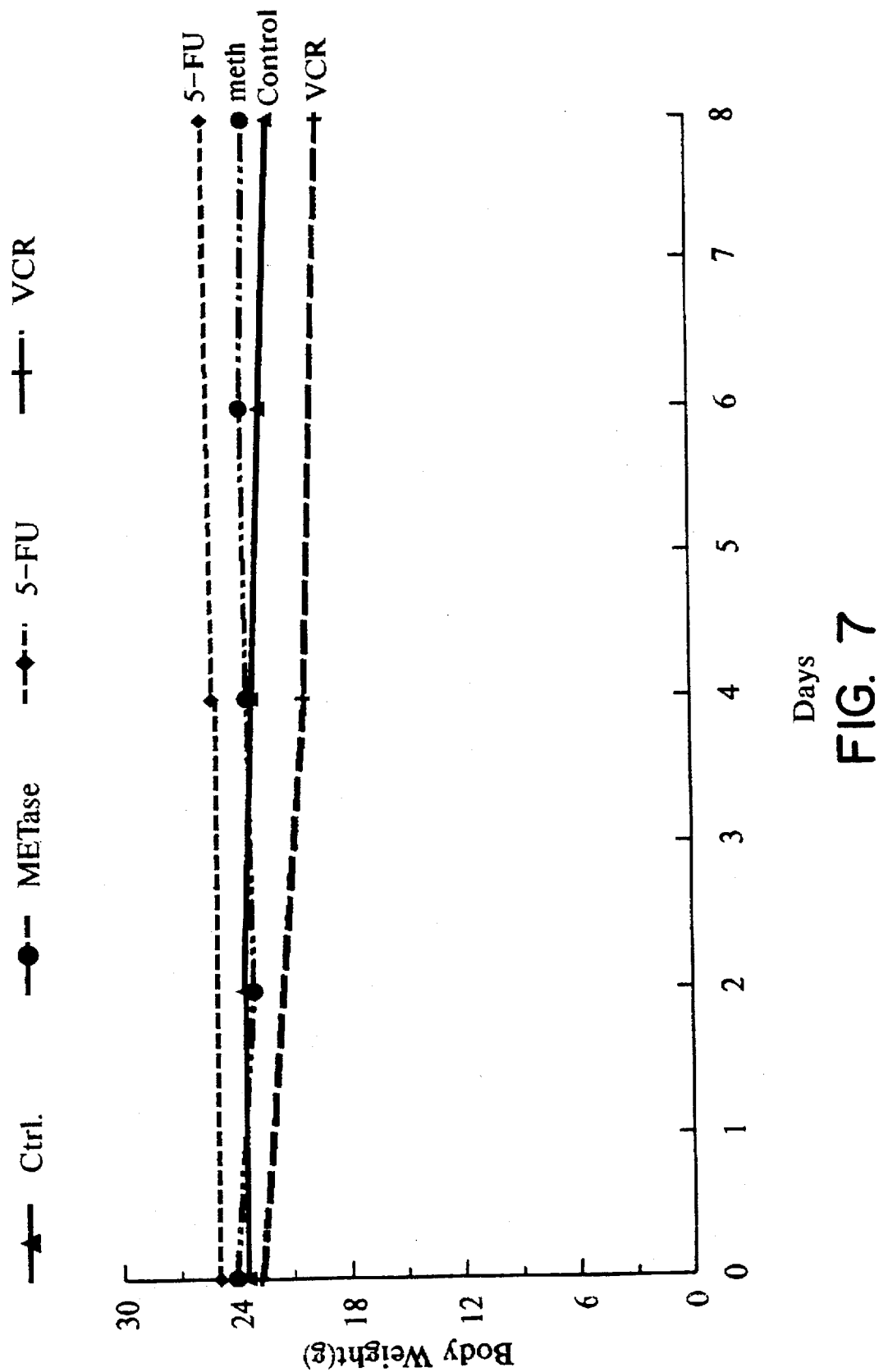
FIG. 7 is a graph that illustrates the effect of methioninase, 5-FU, and vincristine on the body weight of mice implanted with a human lung tumor.
Figure 8:
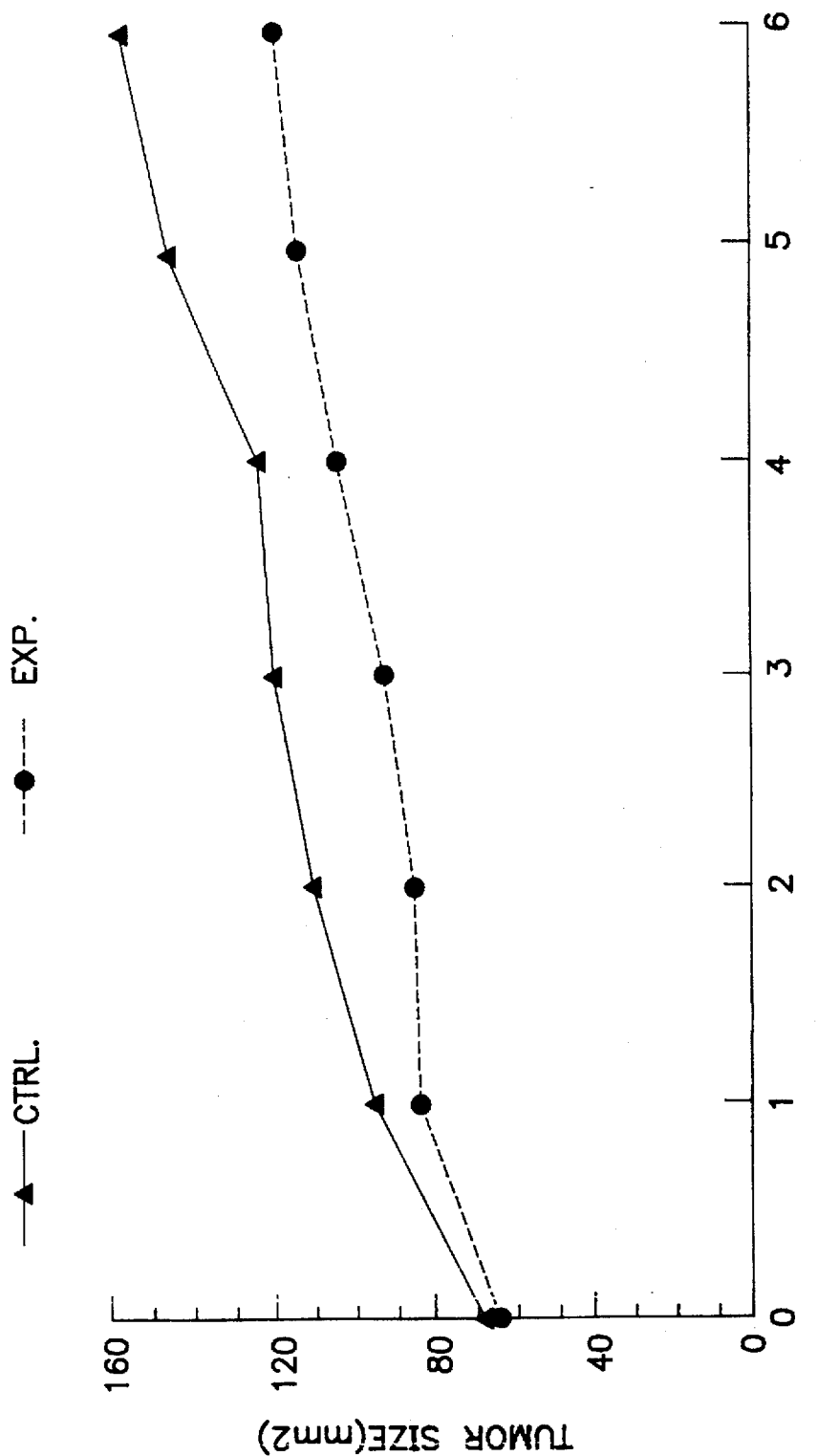
FIG. 8 is a graph that illustrates the efficacy of methioninase for reducing the growth of an HT29 human colon cancer xenograft in mice.

To test the efficacy of methioninase on the reduction of tumor growth, a mouse xenograft model was used. A human lung cancer tumor (H460) was transplanted in the subcutis of nude mice. The mice were divided into four groups of four mice each. Four days after the transplantation, group A was administered 0.4 ml buffer (0.12M sodium chloride, 10 mM sodium phosphate pH 7.1) by intraperitoneal injection every 4 hours; group B was administered methioninase (1 unit/g) by intraperitoneal injection every 4 hours; group C was administered 5-FU (60mg/kg) by intraperitoneal injection every 4 days; and group D was administered with vincristine (VCR) (0.9 mg/kg) by intraperitoneal injection every 4 days. Tumor size and body weight were measured every two days. The results are shown in FIGS. 6 and 7. The results indicate that treatment with methioninase greatly slowed the growth of the H460 human non-small-cell-lung cancer in nude mice. In these experiments, the mice were fed normal, not methionine-depleted, diets. The efficacy of methioninase against H460 was in stark contrast to 5-fluorouracil and vincristine treatment, which were inactive against this tumor. The activity of the administered methioninase did not cause weight loss for up to 10 days treatment at 40–120 units/day indicating the possibility of low toxicity. In contrast, vincristine caused weight loss, indicating toxicity. Thus, methioninase is a highly effective antitumor agent with a new tumor-selective mode of action with minimal toxicity, demonstrating potential clinical effectiveness against human solid tumors. The methioninase also inhibited the growth of the HT 29 human colon cancer in nude mice as shown in FIG. 8.

9. Antigenicity of Methioninase

The methioninase composition prepared by Extraction Method 3 was tested for its antigenicity in mice. Table 7 shows the results of an experiment where BALB/c mice were given intraperitoneal injections of varying amounts of methioninase, in the presence or absence of Freund's Complete Adjuvant (FCA). Five groups of five mice each were tested. The injections were given on day 1 and day 28. Seven days after the last injection, the level of IgE specific for methioninase was measured using solid ELISA. The solid ELISA assay was performed by standard methods, as described in Paul, *Fundamental Immunology*, 438–440, (3d Ed. 1993), and in the references cited therein. The results of each tested group were averaged for the table. The results demonstrate that methioninase injection does not result in a significant level of IgE production in mice. The antigenic reaction only occured in the presence of the adjuvant.

TABLE 7

DEVELOPMENT OF IgE ANTIBODIES TO METHIONINASE

| Methioninase | | | Injection Schedule | | | IgE | |
|---|---|---|---|---|---|---|---|
| | µg | route | FCA | 1st | 2nd | Days after injection | Relative Units |
| I | 50 | i.p. | + | 1 | 28 | 7 | 5 |
| II | 50 | i.p. | – | 1 | 28 | 7 | 1.4 |
| III | 10 | i.p. | – | 1 | 28 | 7 | 1.2 |
| IV | 2 | i.p. | + | 1 | 28 | 7 | 4 |
| V | 2 | i.p. | – | 1 | 28 | 7 | 1.1 | a. Relative Units = $\frac{OD_{405} \text{ of exp mice sera}}{OD_{405} \text{ of exp. control mice sera}}$
b. Results from Solid ELISA (ratio 1:2)
c. Each group n = 5

As shown in Table 8, methioninase also did not appreciably affect the level of IgM or IgG in BALB/c mice. Two groups of 5 mice were administered 50 µg of methioninase by intraperitoneal injection in the presence or absence of adjuvant. Levels of igG and IgM specific for methioninase were measured 21 days after injection by solid ELISA.

Two groups of 5 mice each were tested, and the results were averaged.

Table 8 demonstrates that the antigenic response was only appreciably present in the presence of adjuvant.

TABLE 8

Development of IgM & IgG Antibodies to Methioninase

| Methioninase | Days after | Antibodies (relative units) | |
|---|---|---|---|
| µg FCA route | Injection | IgM | IgG |
| A 50 + IP | 21 | 1.7 | 7.1 |
| B 50 – IP | 21 | 1.07 | 0.67 |

Note:
1. Relative units (antibody titers) = $\frac{OD_{405} \text{ obtained with exp. mice}}{OD_{405} \text{ obtained with normal mice}}$
2. The antibodies were measured by Solid ELISA. The dilution of sera was 1:32.

Methioninase was then tested in a delayed type hypersensitivity assay. BALB/c mice were injected in the footpad with methioninase on day 21, subsequent to two intraperitoneal injections of methioninase on day 0 and 7. The thickness of the footpad was then measured. Two groups of 5 mice each were tested and the results were averaged and presented in Table 9. Table 9 demonstrates that methioninase injection did not appreciably result in a delayed type hypersensitivity reaction.

TABLE 9

Delayed Type Hypersensitivity Reactions to Methioninase

| Treatment | | | | Footpad Reaction | | | |
|---|---|---|---|---|---|---|---|
| Date | 1st | 2nd | METase FCA Route (µg) | Date | Footpad Injection Left | Right | Thickness Ratio L/R |
| EXP | 0 | 7 | 50 + IP | 21 | 10 µg METase | NS | 1.08 |
| CNTL | 0 | 7 | 50 – IP | 21 | 10 µg METase | NS | 1.02 |

Note:
1. The thickness of the left and right footpad was measured 24 hours after footpad injection and the ratio was calculated.
2. Each group n = 5.

Thus, the results of these experiments demonstrate the low level of antigenicity caused by methioninase in mice. Other evidence of this low antigenicity is the observation that multiple injections of methioninase in mice does not decrease the serum half-life of methioninase.

10. Preparation of PEG-methioninase

Methoxy polyethylene glycol succinimidyl carbonate, (M-SC 5000 PEG), molecular weight 5000, was dissolved in 20 mM sodium phosphate buffer (pH 8.3) at a concentration between 2 mM and 20 mM. The molar ratios of M-SC 5000 PEG to methioninase were varied from 6:1 to 240:1. The PEGylation reactions were carried out in reaction buffer (25 mM sodium phosphate buffer, pH 8.3), at 4° C. or 20° C. from 30 minutes to 60 minutes. The reactions were stopped with stop buffer (0.14M sodium phosphate buffer, pH 6.5) at 0° C. Unreacted M-SC 5000 PEG was then removed by gel filtration chromatograpy as described herein. The resulting PEG-methioninase was formulated in 0.12M sodium chloride and 10 mM sodium phosphate (pH 7.2) with the use of 30k Amicon Centriprep concentrators. The PEG-methioninase was then sterilized by filtration with a 0.2 µM micron membrane filter. The PEG-methioninase may be stored at −70° C. for up to 6 months without loss of activity.

Methioninase activity was measured as described in Example 4. The activity of PEG-methioninase was maintained to at least 60% of the activity of nonPEGylated methioninase. PEG-methioninase was analyzed by both native and SDS polyacrylamide gel electrophoresis as described by Laemmli and by Sambrook (Laemmli, *Nature* 227–680, 1970; Sambrook et al., *Molecular Cloning: a laboratory manual* 18.47–18.59, 1989) and modified as follows: Electrophoresis of PEG-methioninase was carried out in 7.5% polyacrylamide-precasted gels in 0.2M Tris-glycine buffer (pH 8.3), with or without SDS. The gels were stained with Coomassie blue and destained with 40% methanol 10% acetic acid. No unmodified methioninase band was seen when PEG-methioninase was applied to native gels, although a very small band could be seen in SDS gels.

PEG-methioninase was then analyzed by an HPLC gel filtration column as follows: PEG-methioninase (20 µl at 1–2 mg/ml) was applied using a 20µ loop to a Progel-TSK G3000 SW (Supelco) column in 0.2M sodium phosphate buffer (pH 7.2) and eluted with 0.2M sodium phosphate buffer (pH 7.2) at a flow rate of 1.0 ml/mn. Only one peak of protein was detected, the PEG-methioninase peack, which was free of unreacted PEG; no non-PEGylated methioninase peak could be detected. The purity of PEG-methioninase was approximately 100%.

a) Time Course Studies of the PEGylation Reaction

The time course of the conjugation of polyethylene glycol to methioninase was measured as follows: 0.07 mM of methioninase was reacted with 0.4 mM of M-SC 5000 PEG in 0.2M sodium phosphate buffer (pH 8.3) for various time periods up to 2 hours at 4° C. The reactions are stopped at various time points with 0.2M sodium phosphate pH 6.5). Non-reacted PEG was removed with a 30k Amicon centriprep concentrator. The results are shown in Table 10 and FIG. 9.

Figure 9:
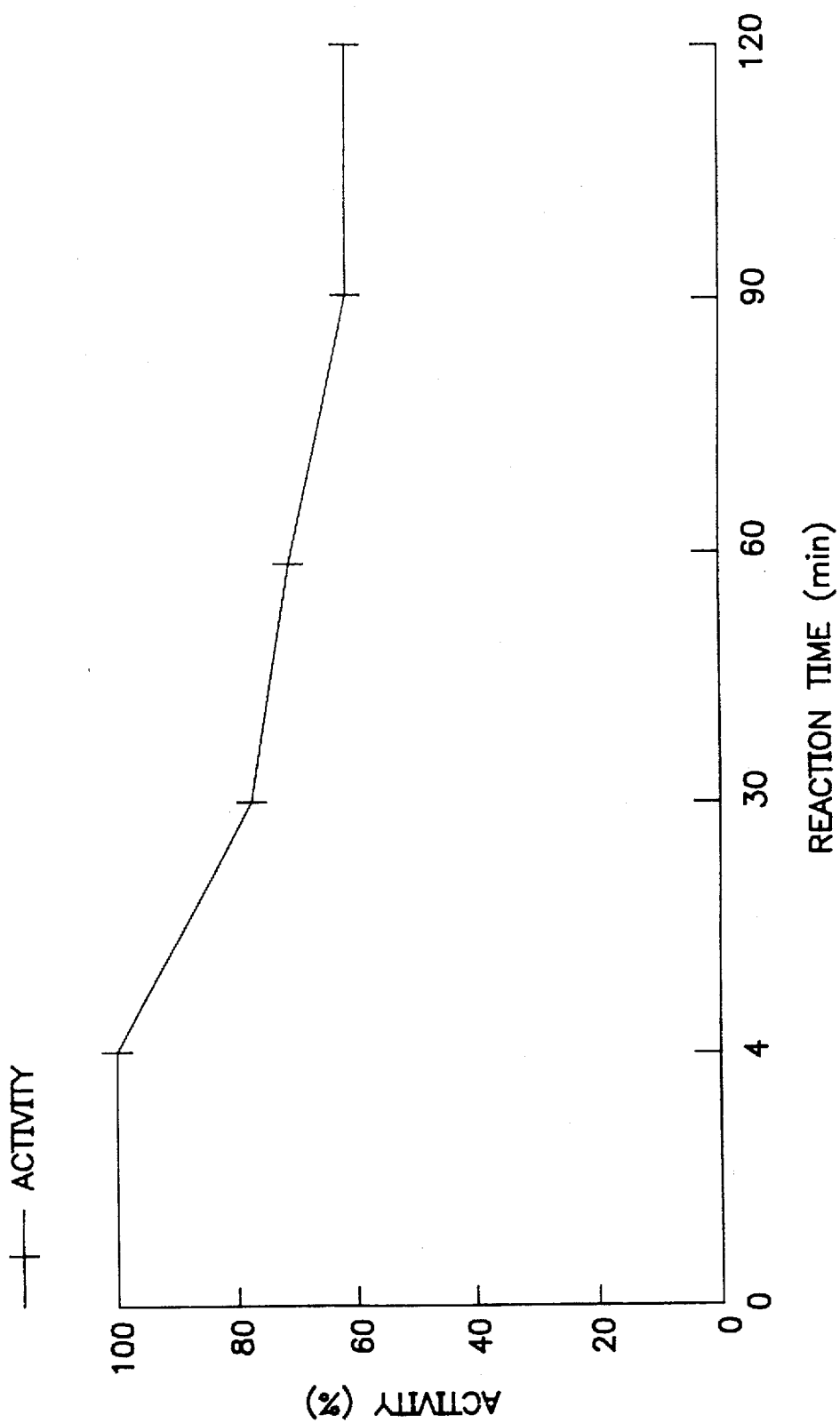
FIG. 9 is a graph that illustrates the time course of methioninase PEGylation. The percentage of methioninase activity present in PEGylated methioninase is graphed as a function of the reaction time of the PEGylation reaction. Methioninase activity is expressed as a percentage of the activity of non-PEGylated methioninase.

PEG-methioninase was analyzed on native and SDS-PAGE gels as described herein. The appearance of a higher molecular weight band was measured and is indicated with −, ±, +, or ++ symbol in Table 10, with − indicating the lack of PEG-methioninase, ± indicating small amounts of PEG-methioninase, and ++ indicating large amounts of PEG-methioninase. Table 10 also indicates the activity of the PEG-methioninase. The activity level from the same experiment is also illustrated in FIG. 9.

TABLE 10

TIME COURSE OF METHIONINASE PEGYLATION

| | Molar Ratio | Condition | | Time Course (Min) | | | | | |
|---|---|---|---|---|---|---|---|---|---|
| | (M*:P**) | °C. | pH | 0 | 4 | 30 | 60 | 90 | 120 |
| Activity (%) | 1:6 | 4 | 8.3 | 100 | 99 | 77 | 70 | 60 | 58 |
| Native Page | Methioninase | | | ++ | + | +− | − | − | − |
| | PEG-methioninase | | | − | + | + | ++ | ++ | ++ |
| SDS PAGE | Methioninase | | | ++ | ++ | ++ | + | + | +− |
| | PEG-methioninase | | | − | +− | + | + | ++ | ++ |

Figure 10:
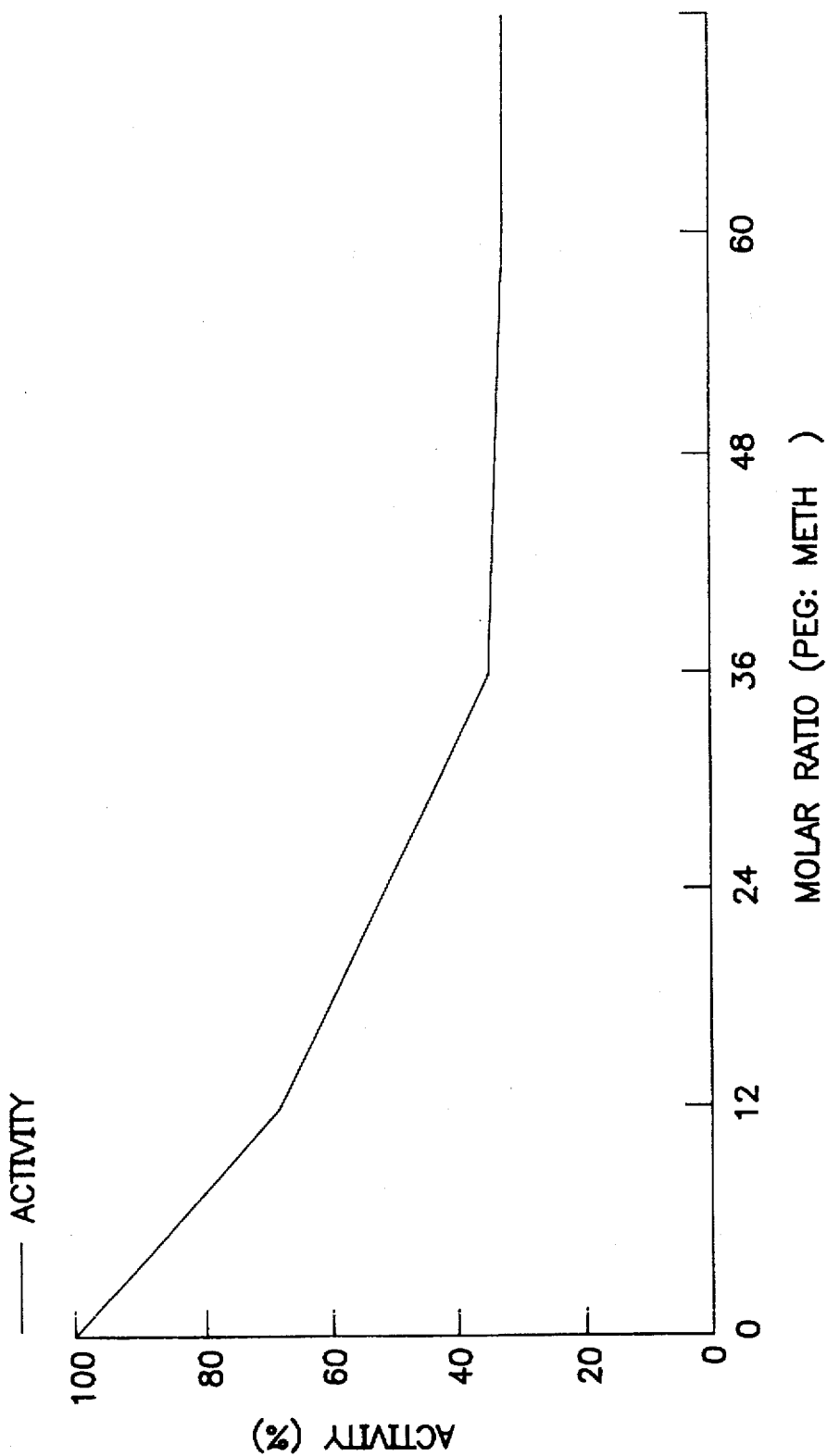
FIG. 10 is a graph that illustrates the concentration dependence of the methioninase PEGylation reaction using M-SC 5000 PEG. The methioninase activity of methioninase subjected to the PEGylation reaction using various molar ratios of polyethylene glycol to methioninase is expressed as a percentage of the activity of non-PEGylated methioninase.

*M: methioninase
**P:M-SC 5000-PEG.

b) Concentration dependence of Methioninase PEGylation with the M-SC 5000 PEG 0.07 mM of methioninase was reacted with various concentrations (0.4 mM to 4.0 mM) of M-SC 5000 PEG in 0.2M sodium phosphate buffer (pH 8.3). The molar ratios were 1:6–1:60. The reactions were carried out at the same conditions as in Example a for 60 minutes at 4° C. The results are shown in Table 11 and FIG. 10.

TABLE 11

CONCENTRATION DEPENDENCE OF METHIONINASE PEGYLATION

| | Condition | | Molar Ratio (P**:M*) | | | | | |
|---|---|---|---|---|---|---|---|---|
| | °C. | min | 0 | 6 | 12 | 24 | 48 | 60 |
| Activity (%) | | 60 | 100 | 79 | 69 | 48 | 33 | 31 |
| Native PAGE | M* | | ++ | − | − | − | − | − |
| | P-M*** | | − | ++ | ++ | ++ | ++ | +++ |
| SDS PAGE | M* | | ++ | + | + | +− | +− | +− |
| | P-M*** | | − | + | ++ | ++ | ++ | +++ |

Figure 11:
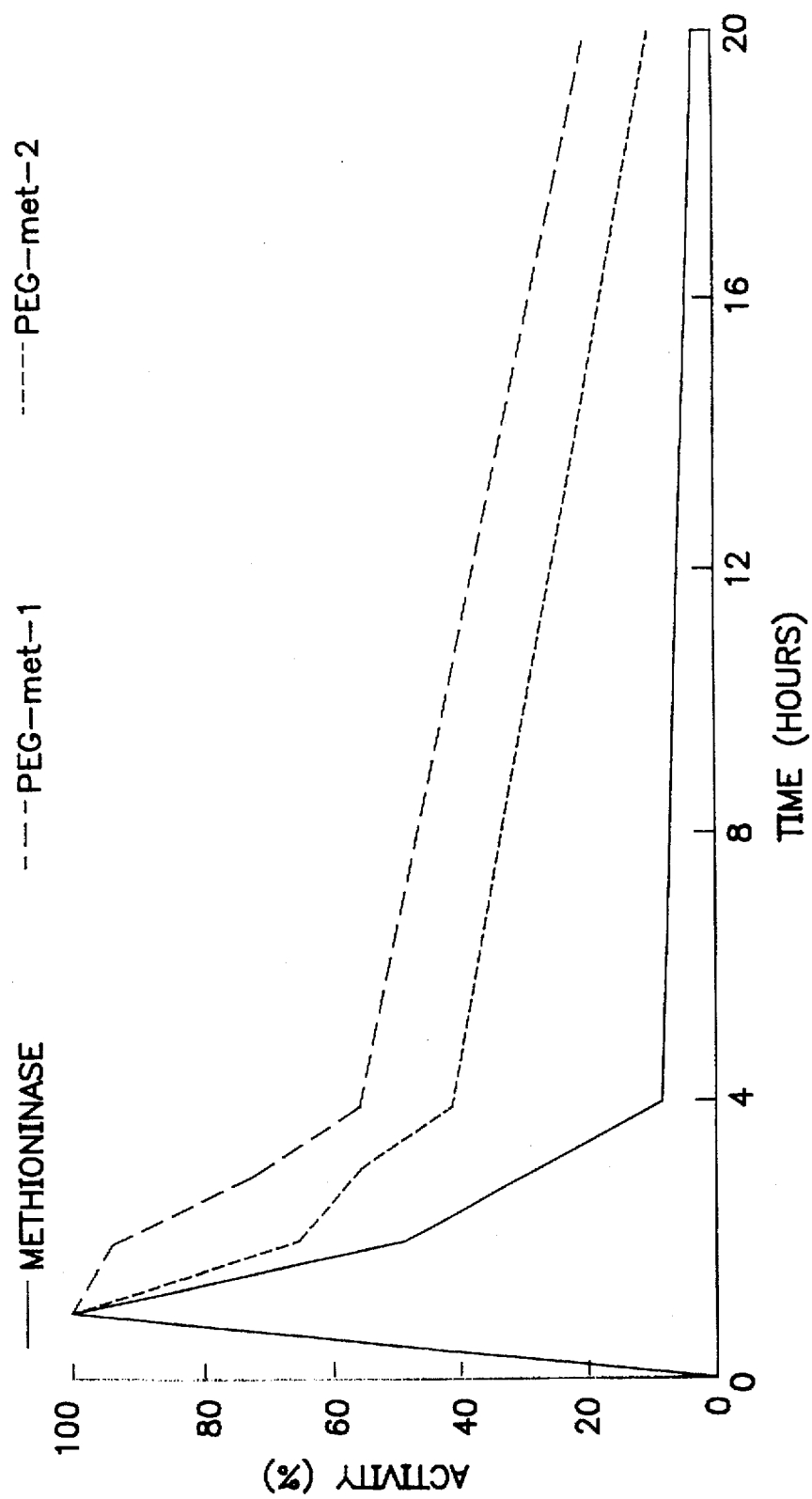
FIG. 11 is a graph that illustrates the pharmokineticas of PEG-methioninase in mice. Methioninase activity is expressed as a percentage of the methioninase activity before injection of methioninase or PEG-methioninase into mice.

*M: methioninase.
**P: PEG.
***P-M: PEG-methioninase c) Pharmokinetics of PEG-Methioninase Molar ratios of PEGylation of methioninase with M-SC 5000 PEG were 1:6 (P1) and 1:12 (P2) respectively. The reactions were carried out at the same conditions as in Example b. The purified P1 and P2 as well as unmodified methioninase were injected into the tail vein of three different groups of mice, respectively. The blood samples were collected at 0, 1, 2, 3, 4 and 20 hours. The activity assay of methioninase and PEG-methioninase and the level of depletion of methionine were measured. The results were shown in Table 12 and FIG. 11.

TABLE 12

PHARMACOKINETICS OF PEG-METHIONINASE

| Mouse Group | Treatment Agent Condition Dose Route | Methioninase Activity in Sera (Relative %. hours) | | | | | | Half-life (hours) |
|---|---|---|---|---|---|---|---|---|
| | | 0 | 1 | 2 | 3 | 4 | 20 | |
| I | M* Buffer 8 units i.v. | 0 | 100 | 49 | 32 | 8 | 2 | 2 |
| II | P1** M:P = 1:6 8 units i.v. | 0 | 100 | 66 | 56 | 41 | 8 | 3.3 |
| III | P2** M:P = 1:12 8 units i.v. | 0 | 100 | 94 | 72 | 56 | 18 | 4.6 |

*M: methioninase.
**P, P1, P2: PEG-methioninase

11: Antigenicity experiment using PEG-methioninase in Guinea Pigs:

Methioninase was reacted with M-SC 5000 PEG at molar ratios of 1:60, 1:120 and 1:240, respectively, at 20° C. for 30 minutes. The other conditions are the same as in Example a. PEG-methioninase was analyzed by the methioninase activity assay, electrophoresis and HPLC. No band or peak of unmodified methioninase was detectable. Thus, PEG-methioninase was the only source of enzyme.

2 mg of methioninase or PEG-methioninase was administered intraperitoneally to guinea pigs every two days for three times total. Two weeks later, 4 mg of methioninase or PEG-methioninase was administered intravenously. 0.2 sodium phosphate buffer and BSA were used as negative and positive controls, respectively, in this experiment. The results are evaluated according to the criteria in Table 13. The results are shown in Table 14. PEGylation of methioninase results in a composition of extremely low antigenicity as tested in guinea pigs. Guinea pigs are known to be more sensitive than humans to antigens.

TABLE 13

EVALUATION CRITERIA OF PEG-METHIONINASE ANTIGENICITY STUDY IN GUINEA PIGS

| | |
|---|---|
| 0. Normal | 1. Restlessness |
| 2. Piloerection | 3. Trembling |
| 4. Running Nose | 5. Sneezing |
| 6. Coughing | 7. Hyperpnea |
| 8. Urination | 9. Evacuation |
| 10. Lacrimation | 11. Dyspnea |
| 12. Rhonchus | 13. Cyanosis |
| 14. Staggering gait | 15. Jumping |
| 16. Gasping & writhing | 17. Convulsion |
| 18. Side position | 19. Cheyne-stokes respiraiton |
| 20. Death | |

EVALUATION CRITERIA

| | | |
|---|---|---|
| (−) | negative: | no change |
| (+) | slight: | 1–4 |
| (++) | moderate: | 1–10 |
| (+++) | severe: | 1–19 |
| (++++) | death: | 20 |

TABLE 14

ANTIGENICITY OF PEG-ONCASE IN GUINEA PIGS

| Sensitization (Inject every two days, 3 times) | | Induction (Two weeks later) | | Evaluation WHO |
|---|---|---|---|---|
| Antigen | Dose | Antigen | Dose | Criteria |
| A Buffer | 0.2 ml, ip | Buffer | 0.2 ml, ip | − |
| B BSA | 1.2 ml, ip | BSA | 10 mg, iv | ++++ |
| C Methioninase | 2.0 mg, ip | Methioninase | 4.0 mg, iv | ++++ |
| D PEG-Methioninase | 2.0 mg, ip | PEG-Methioninase | 4.0 mg, iv | + |

The results showed that PEG-methioninase, in contrast to Bovine Serum Albumin (B.S.A.) and methioninase, has only very slight or no antigenicity in guinea pigs, which suggests that PEG-methioninase is non-immunogeneic when administered to a mammal.

12: Administration of Methioninase for Human Cancer Therapy

A Phase I dose-escalating study of methioninase has been started to determine methioninase toxicity, pharmacokinetics and maximum tolerated dose. A 2-hour infusion of 5,000 units (0.5 g) and 10,000 units (1.0 g) of methioninase has been administered by iv infusion for 2 hours into 2 patients with advanced breast cancer. Blood and urine samples were obtained at frequent intervals from 0 to 24 hours. The toxicity evaluations were carried out according to the WHO grading system. Pharmacokinetic data were obtained for both methioninase and methionine levels in the serum.

Figure 12:
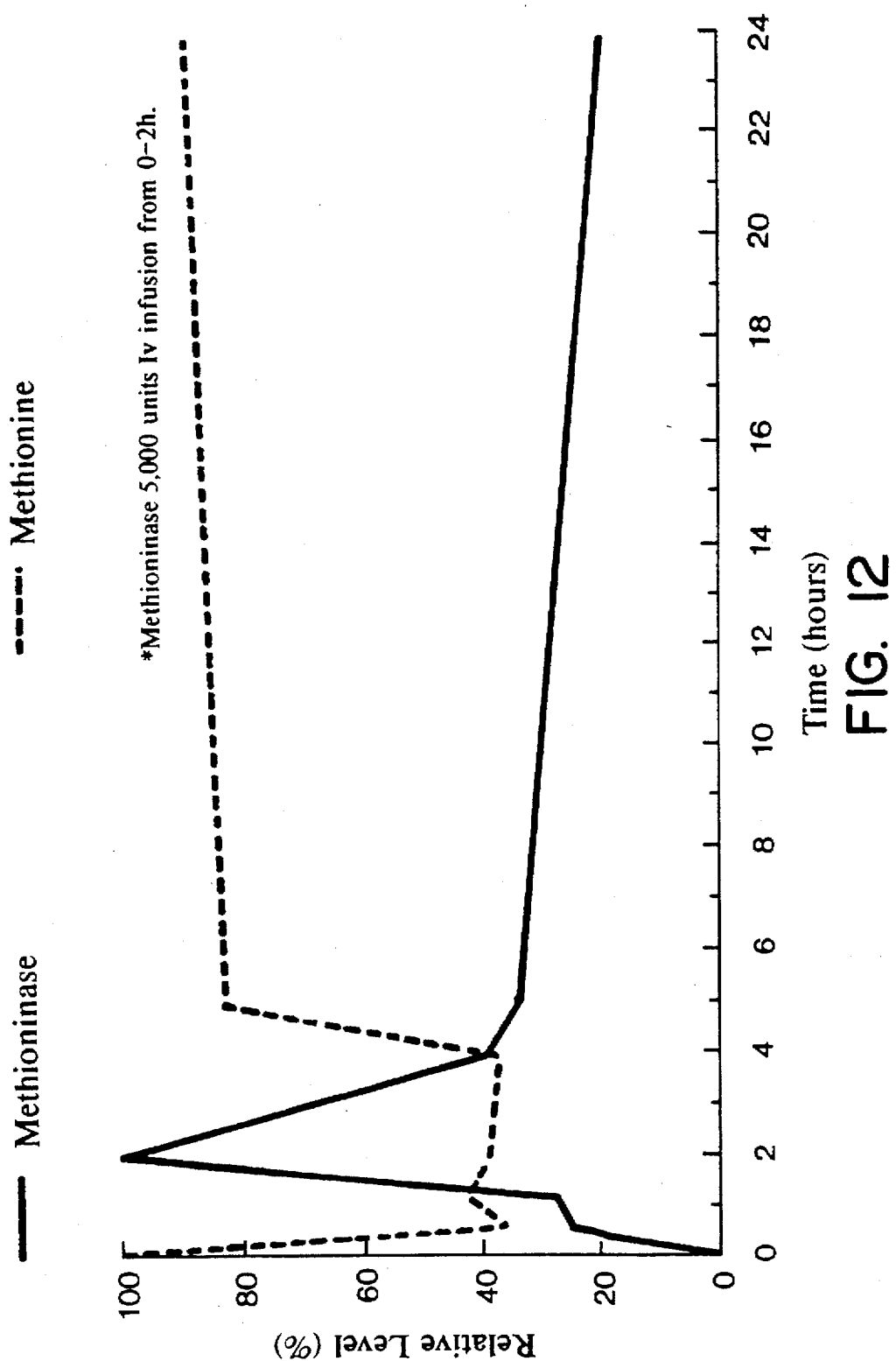
FIGS. 12 and 13 are graphs of the pharmacokinetics of methioninase and methionine after administration of methioninase to two human patients. The percentage of methioninase activity is measured as a relative percentage of activity of the starting preparation of methioninase. The percentage of methionine is measured as a relative percentage of the methionine concentration before administration of methioninase.
Figure 13:
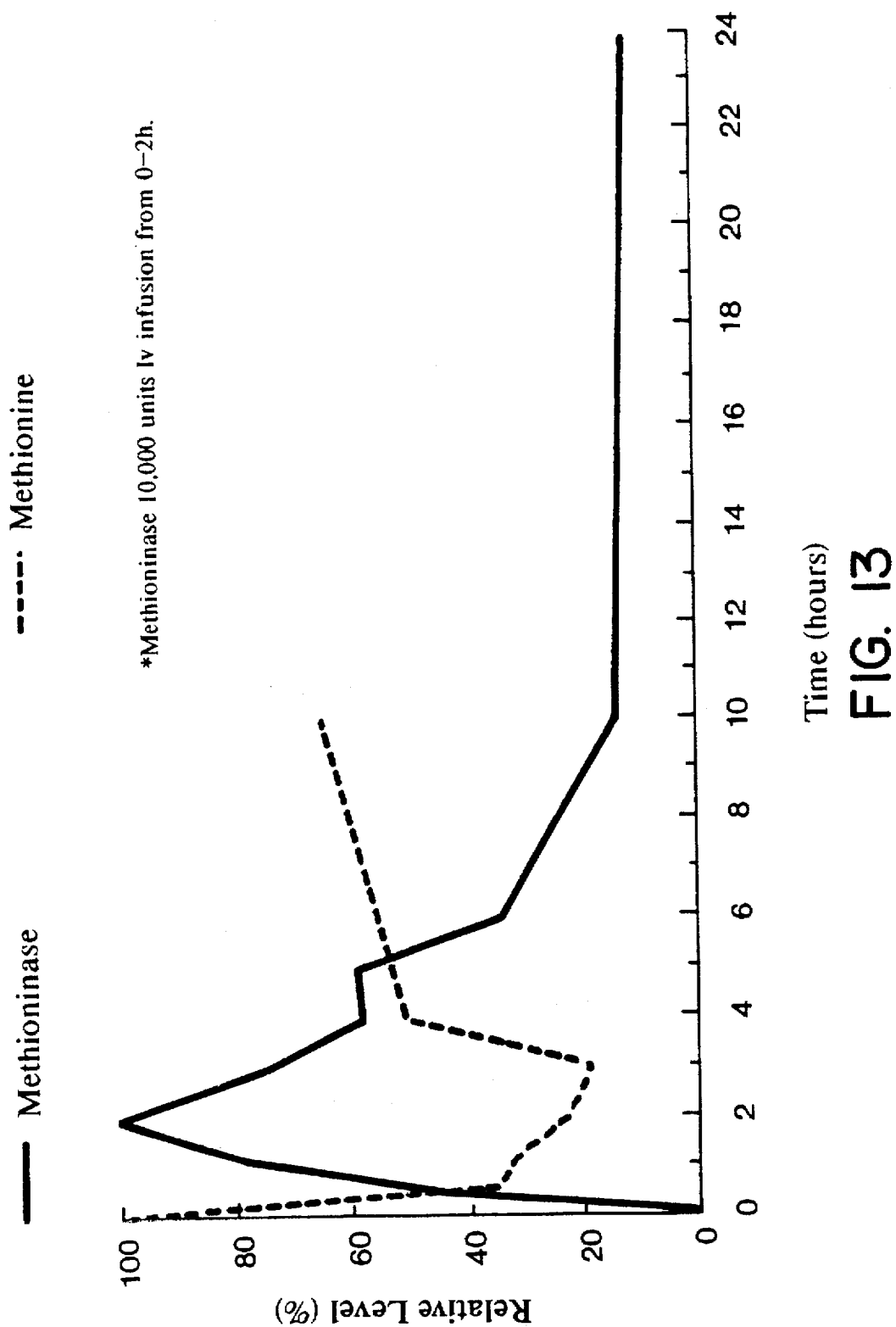

No acute clinical toxicity was observed whatsoever with all the toxicity criteria measured having a minimum grade of 0. The half-life of methioninase was 2 hours and 3.2 h, respectively, in patient 1 and patient 2. The depletion of serum methionine started within 30 minutes of the infusion, and was maintained for 4 hours after the infusion was completed. The lowest serum methionine levels were 35% and 19% of the pretreatment level, respectively, in patient 1 and patient 2. The results are shown in Tables 15–18 and FIGS. 12–13. The patients were treated as follows:

Patient 1: Date: Dec. 14, 1994. Diagnosis: Breast cancer with axillary lymph node and lung metastasis. Female, 46 years old. 5,000 units (0.5 g) of methioninase purified according to extraction method 3 was administered in a 200 ml intravenous infusion in 2 hours.

Patient 2: Date: Feb. 2, 1995. Diagnosis: Breast cancer with axillary lymph node metastasis. Female, 54 years old. 10,000 units (1.0 g) of methioninase purified according to Extraction Method 3 was administered in a 400 ml intravenous infusion in 2 hours.

Toxicity evaluation was performed according to WHO toxicity criteria in four areas: a. History and diagnosis data; b. Physical examination; c. Laboratory evaluation; and d. Pharmacokinetics evaluation (methioninase and methionine levels in serum). The results, shown in Tables 15–18, and FIGS. 12–13, demonstrate that the methioninase of the present invention is not toxic and may be used to decrease methionine levels in humans.

TABLE 15

PATIENT - 1 Physical Examination

| Toxicity | Grade |
|---|---|
| Hemorrhage | 0 |
| Infection | 0 |
| Nausea | 0 |
| Vomiting | 0 |
| Diarrhea | 0 |
| Stomatitis | 0 |
| Alopecia | 0 |
| Pulmonary | 0 |
| Cardiac dysrythmias | 0 |
| Cardiac function | 0 |
| Cardiac-ischemia | 0 |
| Cardiac-pericardial | 0 |
| Hypertension | 0 |
| Hypotension | 0 |
| Neuro-sensory | 0 |
| Neuro-motor | 0 |
| Neuro-cortical | 0 |
| Neuro-cerebellar | 0 |
| Neuro-mood | 0 |
| Neuro-headache | 0 |
| Neuro-constipation | 0 |
| Neuro-hearing | 0 |
| Neuro-vision | 0 |
| Skin | 0 |
| Allergy | 0 |
| Fever in absence of infection | 0 |
| Local | 0 |
| Liver | 0 |
| Weight gain/loss | 0 |

TABLE 16

PATIENT - 2 Laboratory Evaluations

| ELEVATED PARAMETER | GRADE OF TOXICITY - WHO SCALE |
|---|---|
| WBC | 0 |
| PLT | 0 |
| Hgb | 0 |
| Granulocytes/bands | 0 |
| Lymphocytes | 0 |
| Bilirubin | 0 |
| Transaminase (SGOT, SGPT) | 0 |
| Alkaline phosphatase | 0 |
| Creatinine | 0 |
| Proteinuria | 0 |
| Hematuria | 0 |
| Hypercalcemia | 0 |
| Hypocalcemia | 0 |
| Prothrombin time | 0 |
| Partial thromboplastin time | 0 |

TABLE 17

PATIENT - 2 Physical Examination

| Toxicity | Grade |
|---|---|
| Hemorrhage | 0 |
| Infection | 0 |
| Nausea | 0 |
| Vomiting | 0 |
| Diarrhea | 0 |
| Stomatitis | 0 |
| Alopecia | 0 |
| Pulmonary | 0 |
| Cardiac dysrythmias | 0 |
| Cardiac function | 0 |
| Cardiac-ischemia | 0 |
| Cardiac-pericardial | 0 |
| Hypertension | 0 |
| Hypotension | 0 |
| Neuro-sensory | 0 |
| Neuro-motor | 0 |
| Neuro-cortical | 0 |
| Neuro-cerebellar | 0 |
| Neuro-mood | 0 |
| Neuro-headache | 0 |
| Neuro-constipation | 0 |
| Neuro-hearing | 0 |
| Neuro-vision | 0 |
| Skin | 0 |
| Allergy | 0 |
| Fever in absence of infection | 0 |
| Local | 0 |
| Liver | 0 |
| Weight gain/loss | 0 |

TABLE 18

PATIENT - 2 Laboratory Evaluations

| ELEVATED PARAMETER | GRADE OF TOXICITY - WHO SCALE |
|---|---|
| WBC | 0 |
| PLT | 0 |
| Hgb | 0 |
| Granulocytes/bands | 0 |
| Lymphocytes | 0 |
| Bilirubin | 0 |
| Transaminase (SGOT, SGPT) | 0 |
| Alkaline phosphatase | 0 |
| Creatinine | 0 |
| Proteinuria | 0 |
| Hematuria | 0 |
| Hypercalcemia | 0 |
| Hypocalcemia | 0 |
| Prothrombin time | 0 |
| Partial thromboplastin time | 0 |

13: In vivo Depletion of Homocysteine

The in vivo effectiveness of methioninase for use in depleting homocysteine according to the present invention was demonstrated by administration of the enzyme to mice as described in Example 5 with the following modifications: 4 units of methioninase purified according to Extraction Method 3 was injected intraperitoneally in mice. About one hour after the injection, the blood concentrations of methionine, homocysteine, and cysteine were assayed by subjecting 50 μl of mouse serum after derivitization with PITC, to analysis by reverse phase FPLC. The chromatographic profile was compared to that of PITC derivatized internal methionine, homocysteine, and cysteine standards. The sensitivity of the assay was about 0.5 μM methionine.

As shown in Table 19, compared to the levels of homocysteine and cysteine in control, untreated mice, methioninase had significant in vivo homocysteine depletion activity without any significant depletion of in vivo levels of cysteine.

TABLE 19

IN VIVO REDUCTION OF METHIONINE AND EFFECTS ON OTHER AMINO ACIDS BY METHIONINASE

| Sample | Methionine (μM) | Homocysteine (μM) | Cysteine (μM) |
|---|---|---|---|
| Control | 131.8 | 2.7 | 74 |
| Methioninase | 6.6 | 0.5 | 71 |

14: Use of Methioninase for Tumor Imaging

[$^{12}$C] methionine is depleted in a patient by the administration of purified methioninase as described herein. Preferably the methioninase is free of endotoxin. Methioninase (10,000–20,000 units) is administered by intravenous infusion over 4–8 hours. Approximately 5–50 mCi of [$^{11}$C] methioninase is then administered. Positron emission tomography (PET) imaging is then used to detect the uptake of the [$^{11}$C] tracer by the patient's cells. Tracer uptake is quantitated by calculating both the standardized uptake value (S.U.V.) and the kinetic influx constant (Ki) value by means known to those of ordinary skill in the art. Elevated levels of [$^{11}$C] methionine in cells indicates that such cells are likely to be tumor cells. The preferential [$^{11}$C] methionine uptake by the tumor cells provides a means of selectively detecting tumor cells among normal cells.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for lowering homocysteine levels in a patient comprising the step of administering to said patient a therapeutically effective amount of a methioninase composition wherein said methioninase composition contains less than 10 ng endotoxin per mg methioninase.

2. The method of claim 1 wherein said lowering of said homocysteine levels is used to treat cardiovascular disease.

3. The method of claim 2 wherein said cardiovascular disease is arteriosclerosis.

4. The method of claim 3 wherein said methioninase is conjugated to a polymer.

5. The method of claim 4 wherein said polymer is polyethylene glycol.

6. The method of claim 2 wherein said methioninase is conjugated to a polymer.

7. The method of claim 6 wherein said polymer is polyethylene glycol.

8. The method of claim 1 wherein said lowering of said homocysteine levels is used to reduce the potential of cardiovascular disease.

9. The method of claim 8 wherein said cardiovascular disease is arteriosclerosis.

10. The method of claim 8 wherein said methioninase is conjugated to a polymer.

11. The method of claim 10 wherein said polymer is polyethylene glycol.

12. The method of claim 1 wherein said methioninase is conjugated to a polymer.

13. The method of claim 12 wherein said polymer is polyethylene glycol.

* * * * *